(12) United States Patent
Davidson et al.

(10) Patent No.: US 7,815,675 B2
(45) Date of Patent: Oct. 19, 2010

(54) STENT WITH PROTRUDING BRANCH PORTION FOR BIFURCATED VESSELS

(75) Inventors: Charles J. Davidson, Winnetka, IL (US); Gil M. Vardi, Town and Country, MO (US); Eric Williams, Fairfield, CA (US); Amnon Yadin, Kfar Vitkin (IL); Yossi Morik, Chicago, IL (US); Eitan Konstantino, Orinda, CA (US); Tanhum Feld, Moshav Merhavia (IL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 38 days.

(21) Appl. No.: 12/045,537

(22) Filed: Mar. 10, 2008

(65) Prior Publication Data

US 2009/0076592 A1 Mar. 19, 2009

Related U.S. Application Data

(60) Division of application No. 10/802,036, filed on Mar. 17, 2004, now Pat. No. 7,341,598, which is a continuation-in-part of application No. 10/705,247, filed on Nov. 12, 2003, now abandoned, which is a continua-

(60) Provisional application No. 60/404,756, filed on Aug. 21, 2002, provisional application No. 60/487,226, filed on Jul. 16, 2003, provisional application No. 60/488,006, filed on Jul. 18, 2003.

(51) Int. Cl.
*A61F 2/06* (2006.01)

(52) U.S. Cl. .................................... 623/1.35; 623/1.15

(58) Field of Classification Search ................ 623/1.15, 623/1.16, 1.35; 606/108, 191, 192, 194, 606/198

See application file for complete search history.

(56) References Cited

U.S. PATENT DOCUMENTS 4,309,994 A 1/1982 Grunwald (Continued)

FOREIGN PATENT DOCUMENTS

CA 2220864 7/1999

(Continued)

OTHER PUBLICATIONS

U.S. Appl. No. 60/844,011, filed Sep. 12, 2006; Inventor: Broome et al.

(Continued)

*Primary Examiner*—Brian E. Pellegrino
(74) *Attorney, Agent, or Firm*—Vidas, Arrett & Steinraus, P.A.

(57) ABSTRACT

A stent for use in a bifurcated body lumen having a main branch and a side branch. The stent comprises a radially expandable generally tubular stent body having proximal and distal opposing ends with a body wall having a surface extending therebetween. The surface has a geometrical configuration defining a first pattern, and the first pattern has first pattern struts and connectors arranged in a predetermined configuration. The stent also comprises a branch portion comprised of a second pattern, wherein the branch portion is outwardly expandable from the stent body.

20 Claims, 38 Drawing Sheets

Related U.S. Application Data

(60) tion-in-part of application No. 10/644,550, filed on Aug. 21, 2003, now Pat. No. 7,220,275, said application No. 10/802,036 is a continuation-in-part of application No. 09/668,687, filed on Sep. 22, 2000, now abandoned, which is a continuation-in-part of application No. 09/326,445, filed on Jun. 4, 1999, now Pat. No. 6,325,826, said application No. 10/802,036 is a continuation-in-part of application No. 10/440,401, filed on May 19, 2003, which is a continuation of application No. 09/750,372, filed on Dec. 27, 2000, now Pat. No. 6,599,316, said application No. 10/802,036 is a continuation-in-part of application No. 09/963,114, filed on Sep. 24, 2001, now Pat. No. 6,706,062, which is a continuation of application No. 09/326,445, filed on Jun. 4, 1999, now Pat. No. 6,325,826, which is a continuation-in-part of application No. PCT/US99/00835, filed on Jan. 13, 1999, which is a continuation-in-part of application No. 09/007,265, filed on Jan. 14, 1998, now Pat. No. 6,210,429, which is a continuation-in-part of application No. 08/744,002, filed on Nov. 4, 1996, now abandoned.

(56) References Cited

U.S. PATENT DOCUMENTS

| | | |
|---|---|---|
| 4,769,005 A | 9/1988 | Ginsburg et al. |
| 4,774,949 A | 10/1988 | Fogarty |
| 4,896,670 A | 1/1990 | Crittenden |
| 4,905,667 A | 3/1990 | Foerster et al. |
| 4,906,244 A | 3/1990 | Pinchuk et al. |
| 4,935,190 A | 6/1990 | Tennerstedt |
| 4,994,071 A | 2/1991 | MacGregor |
| 5,037,392 A | 8/1991 | Hillstead |
| 5,053,007 A | 10/1991 | Euteneuer |
| 5,087,246 A | 2/1992 | Smith |
| 5,112,900 A | 5/1992 | Buddenhagen et al. |
| 5,147,302 A | 9/1992 | Euteneuer et al. |
| 5,163,989 A | 11/1992 | Campbell et al. |
| 5,209,799 A | 5/1993 | Vigil |
| 5,226,887 A | 7/1993 | Farr et al. |
| 5,306,246 A | 4/1994 | Sahatijian et al. |
| 5,318,587 A | 6/1994 | Davey |
| 5,342,307 A | 8/1994 | Euteneuer et al. |
| 5,342,387 A | 8/1994 | Summers |
| 5,348,538 A | 9/1994 | Wang et al. |
| 5,350,361 A | 9/1994 | Tsukashima et al. |
| 5,358,475 A | 10/1994 | Mares et al. |
| 5,387,235 A | 2/1995 | Chuter |
| 5,403,340 A | 4/1995 | Wang et al. |
| 5,447,497 A | 9/1995 | Sogard et al. |
| 5,456,666 A | 10/1995 | Campbell et al. |
| 5,456,712 A | 10/1995 | Maginot |
| 5,458,572 A | 10/1995 | Campbell et al. |
| 5,476,471 A | 12/1995 | Shifrin et al. |
| 5,478,319 A | 12/1995 | Campbell et al. |
| 5,487,730 A | 1/1996 | Marcadis et al. |
| 5,523,092 A | 6/1996 | Hanson et al. |
| 5,549,552 A | 8/1996 | Peters et al. |
| 5,550,180 A | 8/1996 | Elsik et al. |
| 5,556,383 A | 9/1996 | Wang et al. |
| 5,591,228 A | 1/1997 | Edoga |
| 5,607,444 A | 3/1997 | Lam |
| 5,609,605 A | 3/1997 | Marshall et al. |
| 5,609,627 A | 3/1997 | Goicoechea et al. |
| 5,613,980 A | 3/1997 | Chauhan |
| 5,617,878 A | 4/1997 | Taheri |
| 5,632,762 A | 5/1997 | Myler |
| 5,632,763 A | 5/1997 | Glastra |
| 5,632,772 A | 5/1997 | Alcime et al. |
| 5,636,641 A | 6/1997 | Fariabi |
| 5,669,924 A | 9/1997 | Shaknovich |
| 5,669,932 A | 9/1997 | Fischell et al. |
| 5,676,697 A | 10/1997 | McDonald |
| 5,683,450 A | 11/1997 | Goicoechea et al. |
| 5,697,971 A | 12/1997 | Fischell et al. |
| 5,707,348 A | 1/1998 | Krogh |
| 5,709,713 A | 1/1998 | Evans et al. |
| 5,718,684 A | 2/1998 | Gupta |
| 5,718,724 A | 2/1998 | Goicechea et al. |
| 5,720,735 A | 2/1998 | Dorros |
| 5,746,745 A | 5/1998 | Abele et al. |
| 5,749,825 A | 5/1998 | Fischell et al. |
| 5,749,890 A | 5/1998 | Shaknovich |
| 5,755,734 A | 5/1998 | Richter et al. |
| 5,755,735 A | 5/1998 | Richter et al. |
| 5,755,771 A | 5/1998 | Penn et al. |
| 5,755,773 A | 5/1998 | Evans et al. |
| 5,755,778 A | 5/1998 | Kleshinski |
| 5,782,906 A | 7/1998 | Marshall et al. |
| 5,800,520 A | 9/1998 | Fogarty et al. |
| 5,810,767 A | 9/1998 | Klein |
| 5,824,036 A | 10/1998 | Lauterjung |
| 5,824,040 A | 10/1998 | Cox et al. |
| 5,827,320 A | 10/1998 | Richter et al. |
| 5,830,182 A | 11/1998 | Wang et al. |
| 5,833,657 A | 11/1998 | Reinhardt et al. |
| 5,843,172 A | 12/1998 | Yan |
| 5,851,464 A | 12/1998 | Davila et al. |
| 5,868,777 A | 2/1999 | Lam |
| 5,882,334 A | 3/1999 | Sepetka et al. |
| 5,891,108 A | 4/1999 | Leone et al. |
| 5,893,887 A | 4/1999 | Jayaraman |
| 5,906,640 A | 5/1999 | Penn et al. |
| 5,922,020 A | 7/1999 | Klein et al. |
| 5,922,021 A | 7/1999 | Jang |
| 5,951,941 A | 9/1999 | Wang et al. |
| 5,961,548 A | 10/1999 | Shmulewitz |
| 5,972,017 A | 10/1999 | Berg et al. |
| 5,972,027 A | 10/1999 | Johnson |
| 6,013,054 A | 1/2000 | Jiun Yan |
| 6,013,055 A | 1/2000 | Bampos et al. |
| 6,013,091 A | 1/2000 | Ley et al. |
| 6,017,324 A | 1/2000 | Tu et al. |
| 6,017,363 A | 1/2000 | Hojeibane |
| 6,030,414 A | 2/2000 | Taheri |
| 6,033,380 A | 3/2000 | Butaric et al. |
| 6,033,434 A | 3/2000 | Borghi |
| 6,033,435 A | 3/2000 | Penn et al. |
| 6,048,361 A | 4/2000 | Von Oepen |
| 6,056,775 A | 5/2000 | Borghi et al. |
| 6,059,824 A | 5/2000 | Taheri |
| 6,068,655 A | 5/2000 | Seguin et al. |
| 6,071,285 A | 6/2000 | Lashinski et al. |
| 6,071,305 A | 6/2000 | Brown et al. |
| 6,086,611 A | 7/2000 | Duffy et al. |
| 6,093,203 A | 7/2000 | Uflacker |
| 6,096,070 A | 8/2000 | Ragheb et al. |
| 6,096,073 A | 8/2000 | Webster et al. |
| 6,099,497 A | 8/2000 | Adams et al. |
| 6,113,579 A | 9/2000 | Eidenschink et al. |
| 6,117,117 A | 9/2000 | Mauch |
| 6,117,156 A | 9/2000 | Richter et al. |
| 6,123,721 A | 9/2000 | Jang |
| 6,126,652 A | 10/2000 | McLeod et al. |
| 6,129,738 A | 10/2000 | Lashinski et al. |
| 6,129,754 A | 10/2000 | Kanesaka et al. |
| 6,135,982 A | 10/2000 | Campbell |
| 6,142,973 A | 11/2000 | Carleton et al. |
| 6,143,002 A | 11/2000 | Vietmeier |
| 6,146,356 A | 11/2000 | Wang et al. |
| 6,159,238 A | 12/2000 | Killion et al. |

| | | | | | | |
|---|---|---|---|---|---|---|
| 6,165,195 | A | 12/2000 | Wilson et al. | 6,645,242 | B1 | 11/2003 | Quinn |
| 6,168,621 | B1 | 1/2001 | Vrba | 6,656,162 | B2 | 12/2003 | Santini, Jr. et al. |
| 6,171,278 | B1 | 1/2001 | Wang et al. | 6,669,683 | B2 | 12/2003 | Santini, Jr. et al. |
| 6,183,509 | B1 | 2/2001 | Dibie | 6,689,156 | B1 | 2/2004 | Davidson et al. |
| 6,190,404 | B1 | 2/2001 | Palmaz et al. | 6,692,483 | B2 | 2/2004 | Vardi et al. |
| 6,200,334 | B1 * | 3/2001 | Jang .......................... 623/1.15 | 6,695,877 | B2 | 2/2004 | Brucker et al. |
| 6,203,568 | B1 | 3/2001 | Lombardi et al. | 6,706,062 | B2 | 3/2004 | Vardi et al. |
| 6,206,915 | B1 | 3/2001 | Fagan et al. | 6,709,379 | B1 | 3/2004 | Brandau et al. |
| 6,206,916 | B1 | 3/2001 | Furst | 6,713,119 | B2 | 3/2004 | Hossainy et al. |
| 6,210,380 | B1 | 4/2001 | Mauch | 6,730,064 | B2 | 5/2004 | Ragheb et al. |
| 6,210,429 | B1 | 4/2001 | Vardi et al. | 6,749,628 | B1 | 6/2004 | Cho et al. |
| 6,210,433 | B1 | 4/2001 | Larre | 6,758,859 | B1 | 7/2004 | Dang et al. |
| 6,210,436 | B1 | 4/2001 | Weadock | 6,764,507 | B2 | 7/2004 | Shanley et al. |
| 6,231,598 | B1 | 5/2001 | Berry et al. | 6,773,429 | B2 | 8/2004 | Sheppard, Jr. et al. |
| 6,240,616 | B1 | 6/2001 | Yan | 6,776,793 | B2 | 8/2004 | Brown et al. |
| 6,241,762 | B1 | 6/2001 | Shanley | 6,783,543 | B2 | 8/2004 | Jang |
| 6,253,443 | B1 | 7/2001 | Johnson | 6,790,228 | B2 | 9/2004 | Hossainy et al. |
| 6,254,593 | B1 | 7/2001 | Wilson | 6,811,566 | B1 | 11/2004 | Penn et al. |
| 6,254,632 | B1 | 7/2001 | Wu et al. | 6,827,250 | B2 | 12/2004 | Uhland et al. |
| 6,258,115 | B1 | 7/2001 | Dubrul | 6,835,203 | B1 | 12/2004 | Vardi et al. |
| 6,258,116 | B1 | 7/2001 | Hojeibane | 6,858,038 | B2 | 2/2005 | Heuser |
| 6,258,121 | B1 | 7/2001 | Yang et al. | 6,884,258 | B2 | 4/2005 | Vardi et al. |
| 6,261,305 | B1 | 7/2001 | Marotta et al. | 6,896,699 | B2 | 5/2005 | Wilson et al. |
| 6,261,316 | B1 | 7/2001 | Shaolian et al. | 6,904,658 | B2 | 6/2005 | Hines |
| 6,261,320 | B1 | 7/2001 | Tam et al. | 6,932,837 | B2 | 8/2005 | Amplatz et al. |
| 6,264,662 | B1 | 7/2001 | Lauterjung | 6,946,092 | B1 | 9/2005 | Bertolino et al. |
| 6,264,686 | B1 | 7/2001 | Rieu et al. | 6,955,687 | B2 | 10/2005 | Richter et al. |
| 6,273,908 | B1 | 8/2001 | Ndondo-Lay | 6,955,688 | B2 | 10/2005 | Wilson et al. |
| 6,273,913 | B1 | 8/2001 | Wright et al. | 6,962,602 | B2 | 11/2005 | Vardi et al. |
| 6,280,413 | B1 | 8/2001 | Clark et al. | 6,989,071 | B2 | 1/2006 | Kocur et al. |
| 6,287,628 | B1 | 9/2001 | Hossainy et al. | 7,018,400 | B2 | 3/2006 | Lashinski et al. |
| 6,290,673 | B1 | 9/2001 | Shanley | 7,041,130 | B2 | 5/2006 | Santini, Jr. et al. |
| 6,293,967 | B1 | 9/2001 | Shanley | 7,052,488 | B2 | 5/2006 | Uhland |
| 6,293,968 | B1 | 9/2001 | Taheri | 7,056,323 | B2 | 6/2006 | Mareiro et al. |
| 6,325,822 | B1 | 12/2001 | Chouinard et al. | 7,056,338 | B2 | 6/2006 | Shanley et al. |
| 6,325,826 | B1 | 12/2001 | Vardi et al. | 7,060,091 | B2 | 6/2006 | Killion et al. |
| 6,328,925 | B1 | 12/2001 | Wang et al. | 7,070,616 | B2 | 7/2006 | Majercak et al. |
| 6,334,864 | B1 | 1/2002 | Amplatz et al. | 7,160,321 | B2 | 1/2007 | Shanley et al. |
| 6,334,870 | B1 | 1/2002 | Ehr et al. | 7,169,175 | B2 | 1/2007 | Cottone, Jr. et al. |
| 6,346,089 | B1 | 2/2002 | Dibie | 7,169,179 | B2 | 1/2007 | Shanley et al. |
| 6,348,065 | B1 | 2/2002 | Brown et al. | 7,179,288 | B2 | 2/2007 | Shanley |
| 6,355,060 | B1 | 3/2002 | Lenker et al. | 7,179,289 | B2 | 2/2007 | Shanley |
| 6,358,552 | B1 | 3/2002 | Mandralis et al. | 7,208,010 | B2 | 4/2007 | Shanley et al. |
| 6,361,544 | B1 | 3/2002 | Wilson et al. | 7,208,011 | B2 | 4/2007 | Shanley et al. |
| 6,361,555 | B1 | 3/2002 | Wilson | 7,220,275 | B2 | 5/2007 | Davidson et al. |
| 6,379,381 | B1 | 4/2002 | Hossainy et al. | 2001/0003161 | A1 | 6/2001 | Vardi et al. |
| 6,383,213 | B2 | 5/2002 | Wilson et al. | 2001/0004706 | A1 | 6/2001 | Hojeibane |
| 6,395,018 | B1 | 5/2002 | Castaneda | 2001/0004707 | A1 | 6/2001 | Dereume et al. |
| 6,395,326 | B1 | 5/2002 | Castro et al. | 2001/0012927 | A1 | 8/2001 | Mauch |
| 6,406,457 | B1 | 6/2002 | Wang et al. | 2001/0016766 | A1 | 8/2001 | Vardi et al. |
| 6,423,091 | B1 | 7/2002 | Hojeibane | 2001/0016767 | A1 | 8/2001 | Wilson et al. |
| 6,436,104 | B2 | 8/2002 | Hojeibane | 2001/0016768 | A1 | 8/2001 | Wilson et al. |
| 6,436,134 | B2 | 8/2002 | Richter et al. | 2001/0025195 | A1 | 9/2001 | Shaolian et al. |
| 6,478,816 | B1 | 11/2002 | Kveen et al. | 2001/0027291 | A1 | 10/2001 | Shanley |
| 6,491,666 | B1 | 12/2002 | Santini, Jr. et al. | 2001/0027338 | A1 | 10/2001 | Greenberg |
| 6,506,437 | B1 | 1/2003 | Harish et al. | 2001/0029396 | A1 | 10/2001 | Wilson et al. |
| 6,508,836 | B2 | 1/2003 | Wilson et al. | 2001/0037116 | A1 | 11/2001 | Wilson et al. |
| 6,517,558 | B2 | 2/2003 | Gittings et al. | 2001/0037138 | A1 | 11/2001 | Wilson et al. |
| 6,520,988 | B1 | 2/2003 | Colombo et al. | 2001/0039448 | A1 | 11/2001 | Dibie |
| 6,527,762 | B1 | 3/2003 | Santini, Jr. et al. | 2001/0049552 | A1 | 12/2001 | Richter et al. |
| 6,527,799 | B2 | 3/2003 | Shanley | 2001/0056297 | A1 | 12/2001 | Hojeibane |
| 6,537,256 | B2 | 3/2003 | Santini, Jr. et al. | 2002/0013618 | A1 | 1/2002 | Marotta et al. |
| 6,540,779 | B2 | 4/2003 | Richter et al. | 2002/0013619 | A1 | 1/2002 | Shanley |
| 6,551,351 | B2 | 4/2003 | Smith et al. | 2002/0022874 | A1 | 2/2002 | Wilson |
| 6,551,838 | B2 | 4/2003 | Santini, Jr. et al. | 2002/0026232 | A1 | 2/2002 | Marotta et al. |
| 6,558,422 | B1 | 5/2003 | Baker et al. | 2002/0035392 | A1 | 3/2002 | Wilson |
| 6,562,065 | B1 | 5/2003 | Shanley | 2002/0038146 | A1 | 3/2002 | Harry |
| 6,579,309 | B1 | 6/2003 | Loos et al. | 2002/0042650 | A1 | 4/2002 | Vardi et al. |
| 6,579,312 | B2 | 6/2003 | Wilson et al. | 2002/0052648 | A1 | 5/2002 | McGuckin, Jr. et al. |
| 6,582,394 | B1 | 6/2003 | Reiss et al. | 2002/0072790 | A1 | 6/2002 | McGuckin, Jr. et al. |
| 6,596,020 | B2 | 7/2003 | Vardi et al. | 2002/0095208 | A1 | 7/2002 | Gregorich et al. |
| 6,599,316 | B2 | 7/2003 | Vardi et al. | 2002/0111675 | A1 | 8/2002 | Wilson |
| 6,638,302 | B1 | 10/2003 | Curcio et al. | 2002/0156516 | A1 | 10/2002 | Vardi et al. |

| Publication | Date | Inventor |
|---|---|---|
| 2002/0156517 A1 | 10/2002 | Perouse |
| 2002/0163104 A1 | 11/2002 | Motsenbocker et al. |
| 2002/0165604 A1 | 11/2002 | Shanley |
| 2002/0173835 A1 | 11/2002 | Bourang et al. |
| 2002/0173840 A1 | 11/2002 | Brucker et al. |
| 2002/0183763 A1 | 12/2002 | Callol et al. |
| 2002/0193872 A1 | 12/2002 | Trout, III et al. |
| 2002/0193873 A1 | 12/2002 | Brucker et al. |
| 2003/0009209 A1 | 1/2003 | Hojeibane |
| 2003/0028233 A1 | 2/2003 | Vardi et al. |
| 2003/0050688 A1 | 3/2003 | Fischell et al. |
| 2003/0055378 A1 | 3/2003 | Wang et al. |
| 2003/0055483 A1 | 3/2003 | Gumm |
| 2003/0074047 A1 | 4/2003 | Richter |
| 2003/0083687 A1 | 5/2003 | Pallazza |
| 2003/0093109 A1 | 5/2003 | Mauch |
| 2003/0097169 A1 | 5/2003 | Brucker |
| 2003/0105511 A1 | 6/2003 | Welsh et al. |
| 2003/0114912 A1 | 6/2003 | Sequin et al. |
| 2003/0125791 A1 | 7/2003 | Sequin et al. |
| 2003/0125802 A1 | 7/2003 | Callol et al. |
| 2003/0135259 A1 | 7/2003 | Simso |
| 2003/0163157 A1 | 8/2003 | McMorrow et al. |
| 2003/0167085 A1 | 9/2003 | Shanley |
| 2003/0181923 A1 | 9/2003 | Vardi |
| 2003/0195606 A1 | 10/2003 | Davidson et al. |
| 2003/0199970 A1 | 10/2003 | Shanley |
| 2004/0006381 A1 | 1/2004 | Sequin et al. |
| 2004/0015227 A1 | 1/2004 | Vardi et al. |
| 2004/0044396 A1 | 3/2004 | Clerc et al. |
| 2004/0059406 A1 | 3/2004 | Cully et al. |
| 2004/0068161 A1 | 4/2004 | Couvillon, Jr. |
| 2004/0073294 A1 | 4/2004 | Diaz et al. |
| 2004/0088007 A1 | 5/2004 | Eidenschink |
| 2004/0093071 A1 | 5/2004 | Jang |
| 2004/0117003 A1 | 6/2004 | Ouriel et al. |
| 2004/0122505 A1 | 6/2004 | Shanley |
| 2004/0122506 A1 | 6/2004 | Shanley et al. |
| 2004/0127976 A1 | 7/2004 | Diaz |
| 2004/0127977 A1 | 7/2004 | Shanley |
| 2004/0133268 A1 | 7/2004 | Davidson et al. |
| 2004/0138732 A1 | 7/2004 | Suhr et al. |
| 2004/0138737 A1 | 7/2004 | Davidson et al. |
| 2004/0142014 A1 | 7/2004 | Livack et al. |
| 2004/0143321 A1 | 7/2004 | Livack et al. |
| 2004/0143322 A1 | 7/2004 | Livack et al. |
| 2004/0148006 A1 | 7/2004 | Davidson et al. |
| 2004/0148012 A9 | 7/2004 | Jang |
| 2004/0172121 A1 | 9/2004 | Eidenschink et al. |
| 2004/0186560 A1 | 9/2004 | Alt |
| 2004/0202692 A1 | 10/2004 | Shanley et al. |
| 2004/0204750 A1 | 10/2004 | Dinh |
| 2004/0215227 A1 | 10/2004 | McMorrow et al. |
| 2004/0220661 A1 | 11/2004 | Shanley et al. |
| 2004/0225345 A1 | 11/2004 | Fischell et al. |
| 2004/0236408 A1 | 11/2004 | Shanley |
| 2004/0249449 A1 | 12/2004 | Shanley et al. |
| 2004/0267352 A1 | 12/2004 | Davidson et al. |
| 2005/0004656 A1 | 1/2005 | Das |
| 2005/0010278 A1 | 1/2005 | Vardi et al. |
| 2005/0015108 A1 | 1/2005 | Williams et al. |
| 2005/0015135 A1 | 1/2005 | Shanley |
| 2005/0043816 A1 | 2/2005 | Datta et al. |
| 2005/0060027 A1 | 3/2005 | Khenansho et al. |
| 2005/0096726 A1 | 5/2005 | Sequin et al. |
| 2005/0102017 A1 | 5/2005 | Mattison |
| 2005/0102021 A1 | 5/2005 | Osborne |
| 2005/0102023 A1 | 5/2005 | Yadin et al. |
| 2005/0119731 A1 | 6/2005 | Brucker et al. |
| 2005/0125076 A1 | 6/2005 | Ginn |
| 2005/0131526 A1 | 6/2005 | Wong |
| 2005/0149161 A1 | 7/2005 | Eidenschink et al. |
| 2005/0154442 A1 | 7/2005 | Eidenschink et al. |
| 2005/0154444 A1 | 7/2005 | Quadri |
| 2005/0183259 A1 | 8/2005 | Eidenschink et al. |
| 2005/0187602 A1 | 8/2005 | Eidenschink |
| 2005/0187611 A1 | 8/2005 | Ding et al. |
| 2005/0192657 A1 | 9/2005 | Colen et al. |
| 2005/0209673 A1 | 9/2005 | Shaked |
| 2005/0222668 A1 | 10/2005 | Schaeffer et al. |
| 2005/0228483 A1 | 10/2005 | Kaplan et al. |
| 2005/0273149 A1 | 12/2005 | Tran et al. |
| 2006/0015134 A1 | 1/2006 | Trinidad |
| 2006/0034884 A1 | 2/2006 | Stenzel |
| 2006/0036315 A1 | 2/2006 | Yadin et al. |
| 2006/0041303 A1 | 2/2006 | Israel |
| 2006/0045901 A1 | 3/2006 | Weber |
| 2006/0079956 A1 | 4/2006 | Eigler et al. |
| 2006/0088654 A1 | 4/2006 | Ding et al. |
| 2006/0093643 A1 | 5/2006 | Stenzel |
| 2006/0100686 A1 | 5/2006 | Bolduc et al. |
| 2006/0122698 A1 | 6/2006 | Spencer et al. |
| 2006/0173528 A1 | 8/2006 | Feld et al. |
| 2006/0235333 A1 | 10/2006 | Couvillon, Jr. |
| 2006/0287712 A1 | 12/2006 | Eidenschink |
| 2007/0005126 A1 | 1/2007 | Tischler |
| 2007/0050016 A1 | 3/2007 | Gregorich et al. |
| 2007/0073376 A1 | 3/2007 | Krolik et al. |
| 2007/0073384 A1 | 3/2007 | Brown et al. |
| 2007/0100434 A1 | 5/2007 | Gregorich et al. |
| 2007/0173787 A1 | 7/2007 | Huang et al. |
| 2007/0173923 A1 | 7/2007 | Savage et al. |

FOREIGN PATENT DOCUMENTS

| | | |
|---|---|---|
| DE | 9014845 | 2/1991 |
| DE | 29701758 | 3/1997 |
| DE | 29701883 | 5/1997 |
| DE | 19921788 | 11/2000 |
| EP | 0479730 | 10/1991 |
| EP | 0565796 | 10/1993 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0950386 | 10/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 94/23787 | 10/1994 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |

| | | |
|---|---|---|
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/23228 | 6/1998 |
| WO | 98/36709 | 8/1998 |
| WO | 98/36784 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15108 | 4/1999 |
| WO | 99/15109 | 4/1999 |
| WO | 99/23977 | 5/1999 |
| WO | 99/24104 | 5/1999 |
| WO | 99/29262 | 6/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 02/16719 | 3/2000 |
| WO | 00/27307 | 5/2000 |
| WO | 00/27463 | 5/2000 |
| WO | 00/28922 | 5/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | 00/74595 | 12/2000 |
| WO | 01/17577 | 3/2001 |
| WO | 01/21095 | 3/2001 |
| WO | 01/21109 | 3/2001 |
| WO | 01/21244 | 3/2001 |
| WO | 01/26584 | 4/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45594 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/66036 | 9/2001 |
| WO | 01/70294 | 9/2001 |
| WO | 01/70299 | 9/2001 |
| WO | 01/74273 | 10/2001 |
| WO | 01/89409 | 11/2001 |
| WO | 01/91918 | 12/2001 |
| WO | 01/93781 | 12/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2005/041810 | 5/2005 |
| WO | 2005/122959 | 12/2005 |
| WO | 2006/028925 | 3/2006 |
| WO | 2006/074476 | 7/2006 |
| WO | 2006/127127 | 11/2006 |

OTHER PUBLICATIONS

U.S. Appl. No. 09/663,111, filed Sep. 15, 2000; Inventor: Davidson et al.
U.S. Appl. No. 09/614,472, filed Jul. 11, 2000; Inventor: Davidson et al.
U.S. Appl. No. 09/325,996, filed Jun. 4, 1999; Inventor: Vardi et al.
Chevalier, M.D., Bernard, "Placement of Coronary Stents in Bifurcation Lesions by the "Culotte" Technique," The American Journal of Cardiology, vol. 82, pp. 943-949 (Oct. 15, 1998).
Nakamura M.D., Shigeru, "Techniques for Palmaz-Schatz Stent Deployment in Lesions with a Large Side Branch," Catheterization and Cardivascular Diagnosis, vol. 34, pp. 353-361 (1995).
Caputo, Ronald P., "Stent Jail: A Minimum-Security Prison," The American Journal of Cardiology, vol. 77, pp. 1226-1230 (Jun. 1, 1996).
Colombo, M.D., Antonio, ""Kissing" Stent for Bifurcational Coronary Lesions," Catheterization and Cardiovascular Diagnosis, vol. 30, pp. 327-330 (Dec. 1993).
Carrie, M.D., Didier, ""T"-Shaped Stent Placement: A Technique for the Treatment of Dissected Bifurcation Lesions," Catheterization and Cardiovascular Diagnosis, vol. 37 pp. 311-313 (Mar. 1996).
Katoh, M.D., Osamu, "New Double Wire Technique to Stent Ostial Lesions," Catheterization and Cardiovascular Diagnosis, vol. 40, pp. 400-402 (Apr. 1997).
Lewis, M.D., Bruce E., "Acute procedural results in the treatment of 30 coronary artery bifurcation lesions with a double-wire atherectomy technique for side-branch protection," American Heart Journal, vol. 127:6, pp. 1600-1607.
Yamashita, M.D., PhD., Takehiro, "Bifurcation Lesions: Two Stents Versus One Stent—Immediate and Follow-up Results," Journal of America College of Cardiology, vol. 35:5, pp. 1145-1151 (Apr. 2000).
Satler, M.D., Lowell F., "Bifurcation Disease: To Treat or Not to Treat," Catheterization and Cardiovascular Interventions, vol. 50, pp. 411-412 (2000).

* cited by examiner

STENT WITH PROTRUDING BRANCH PORTION FOR BIFURCATED VESSELS

CROSS-REFERENCE TO RELATED APPLICATIONS

This application is a divisional application of U.S. patent application Ser. No. 10/802,036, filed Mar. 17, 2004, which is a continuation-in-part of U.S. patent application Ser. No. 10/705,247, filed Nov. 12, 2003, which claims the benefit of U.S. patent application Ser. No. 10/644,550, filed Aug. 21, 2003, which claims the benefit of U.S. Provisional Application No. 60/404,756, filed Aug. 21, 2002, U.S. Provisional Application No. 60/487,226, filed Jul. 16, 2003, and U.S. Provisional Application No. 60/488,006, filed Jul. 18, 2003, the entire contents of which are hereby incorporated herein by reference. The parent application, U.S. patent application Ser. No. 10/802,036, is also continuation-in-part of U.S. patent application Ser. No. 09/668,687, filed Sep. 22, 2000, which is a continuation-in-part of U.S. patent application Ser. No. 09/326,445, filed Jun. 4, 1999, which issued as U.S. Pat. No. 6,325,826. The parent application is also a continuation-in-part of U.S. patent application Ser. No. 10/440,401, filed May 19, 2003 which is a continuation of U.S. patent application Ser. No. 09/750,372, filed Dec. 27, 2000, which issued as U.S. Pat. No. 6,599,316. The parent application is also a continuation-in-part of U.S. patent application Ser. No. 09/963,114, filed Sep. 24, 2001, which is a continuation of U.S. patent application Ser. No. 09/326,445. U.S. patent application Ser. No. 09/326,445 is continuation-in-part of PCT Application No. US99/00835, filed Jan. 13, 1999, which claims the benefit of U.S. patent application Ser. No. 09/007,265, filed Jan. 14, 1998, which issued as U.S. Pat. No. 6,210,429, which is a continuation-in-part of U.S. patent application Ser. No. 08/744,002, filed Nov. 4, 1996. The entire contents of all of the above references are incorporated herein by reference.

FIELD OF THE INVENTION

The present invention relates to the field of medical stents and, more particularly, to a stent for the treatment of lesions and other problems in or near a vessel bifurcation.

BACKGROUND OF THE INVENTION

A stent is an endoprosthesis scaffold or other device that typically is intraluminally placed or implanted within a vein, artery, or other tubular body organ for treating an occlusion, stenosis, aneurysm, collapse, dissection, or weakened, diseased, or abnormally dilated vessel or vessel wall, by expanding the vessel or by reinforcing the vessel wall. In particular, stents are quite commonly implanted into the coronary, cardiac, pulmonary, neurovascular, peripheral vascular, renal, gastrointestinal and reproductive systems, and have been successfully implanted in the urinary tract, the bile duct, the esophagus, the tracheo-bronchial tree and the brain, to reinforce these body organs. Two important current widespread applications for stents are for improving angioplasty results by preventing elastic recoil and remodeling of the vessel wall and for treating dissections in blood vessel walls caused by balloon angioplasty of coronary arteries, as well as peripheral arteries, by pressing together the intimal flaps in the lumen at the site of the dissection. Conventional stents have been used for treating more complex vascular problems, such as lesions at or near bifurcation points in the vascular system, where a secondary artery branches out of a larger, main artery, with limited success rates.

Conventional stent technology is relatively well developed. Conventional stent designs typically feature a straight tubular, single type cellular structure, configuration, or pattern that is repetitive through translation along the longitudinal axis. In many stent designs, the repeating structure, configuration, or pattern has strut and connecting members that impede blood flow at bifurcations. Furthermore, the configuration of struts and connecting members may obstruct the use of post-operative devices to treat a branch vessel in the region of a vessel bifurcation. For example, deployment of a first stent in the main lumen may prevent a physician from inserting a branch stent through the ostium of a branch vessel of a vessel bifurcation in cases where treatment of the main vessel is suboptimal because of displaced diseased tissue (for example, due to plaque shifting or "snow plowing"), occlusion, vessel spasm, dissection with or without intimal flaps, thrombosis, embolism, and/or other vascular diseases. As a result, the physician may choose either to insert a stent into the branch in cases in which such additional treatment may otherwise be unnecessary, or alternatively the physician may elect not to treat, or to "sacrifice", such side lumen. Accordingly, the use of regular stents to treat diseased vessels at or near a vessel bifurcation may create a risk of compromising the benefit of stent usage to the patient after the initial procedure and in future procedures on the main vessel, branch vessels, and/or the bifurcation point.

A regular stent is designed in view of conflicting considerations of coverage versus access. For example, to promote coverage, the cell structure size of the stent may be minimized for optimally supporting a vessel wall, thereby preventing or reducing tissue prolapse. To promote access, the cell size may be maximized for providing accessibility of blood flow and of a potentially future implanted branch stent to branch vessels, thereby preventing "stent jailing", and minimizing the amount of implanted material. Regular stent design has typically compromised one consideration for the other in an attempt to address both. Problems the present inventors observed involving side branch jailing, fear of plaque shifting, total occlusion, and difficulty of the procedure are continuing to drive the present inventors' into the development of novel, non-conventional or special stents, which are easier, safer, and more reliable to use for treating the above-indicated variety of vascular disorders.

Although conventional stents are routinely used in clinical procedures, clinical data shows that these stents are not capable of completely preventing in-stent restenosis (ISR) or restenosis caused by intimal hyperplasia. In-stent restenosis is the reoccurrence of the narrowing or blockage of an artery in the area covered by the stent following stent implantation. Patients treated with coronary stents can suffer from in-stent restenosis.

Many pharmacological attempts have been made to reduce the amount of restenosis caused by intimal hyperplasia. Many of these attempts have dealt with the systemic delivery of drugs via oral or intravascular introduction. However, success with the systemic approach has been limited.

Systemic delivery of drugs is inherently limited since it is difficult to achieve constant drug delivery to the inflicted region and since systemically administered drugs often cycle through concentration peaks and valleys, resulting in time periods of toxicity and ineffectiveness. Therefore, to be effective, anti-restenosis drugs should be delivered in a localized manner.

One approach for localized drug delivery utilizes stents as delivery vehicles. For example, stents seeded with transfected endothelial cells expressing bacterial beta-galactosidase or human tissue-type plasminogen activator were utilized as therapeutic protein delivery vehicles. See, e.g., Dichek, D. A. et al., "Seeding of Intravascular Stents With Genetically Engineered Endothelial Cells", Circulation, 80:1347-1353 (1989).

U.S. Pat. No. 5,679,400, International Patent Application WO 91/12779, entitled "Intraluminal Drug Eluting Prosthesis," and International Patent Application WO 90/13332, entitled "Stent With Sustained Drug Delivery" disclose stent devices capable of delivering antiplatelet agents, anticoagulant agents, antimigratory agents, antimetabolic agents, and other anti-restenosis drugs.

U.S. Pat. Nos. 6,273,913, 6,383,215, 6,258,121, 6,231, 600, 5,837,008, 5,824,048, 5,679,400 and 5,609,629 teach stents coated with various pharmaceutical agents such as Rapamycin, 17-beta-estradiol, Taxol and Dexamethasone.

Although prior art references disclose numerous stents configurations coated with one or more distinct anti-restenosis agents, they do not disclose the inventive stent design of the present application. There is, therefore, a need for a stent design that can effectively provide ostial branch support in a vessel bifurcation and effectively act as a delivery vehicle for drugs useful in preventing restenosis. This is particularly true in complicated cases, such as lesions located at a bifurcation.

SUMMARY OF THE INVENTION

The present invention is directed to a stent for use in a bifurcated body lumen having a main branch and a side branch. The stent comprises a radially expandable generally tubular stent body having proximal and distal opposing ends with a body wall having a surface extending therebetween. The surface has a geometrical configuration defining a first pattern, and the first pattern has first pattern struts and connectors arranged in a predetermined configuration. The stent also comprises a branch portion comprised of a second pattern, wherein the branch portion is at least partially detachable from the stent body.

In one embodiment, the second pattern is configured according to the first pattern having at least one absent connector, and in another embodiment, the second pattern has a plurality of absent connectors. The second pattern may have second pattern struts, and the second pattern struts can be more densely packed than the first pattern struts.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the invention may be embodied in practice.

In the drawings.

DESCRIPTION OF THE PREFERRED EMBODIMENTS

Figure 1:
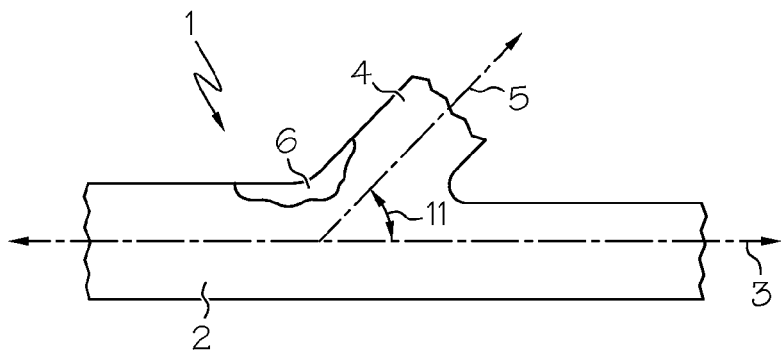
FIG. 1 is an illustration of a blood vessel bifurcation having an obstruction.

The present invention relates to stents for placement at vessel bifurcations and are generally configured to at least partially cover a portion of a branch vessel as well as a main vessel. Referring to FIG. 1, an exemplary blood vessel bifurcation 1 is shown, having a main vessel 2 extending along a main vessel axis 3 and a branch vessel 4 extending along a branch vessel axis 5. Main vessel 2 and branch vessel 4 are disposed at an angle 11 of less than 90 degrees. An obstruction 6 is located within bifurcation 1, spanning or at least partially obstructing main vessel 2 and a proximal portion branch vessel 4.

Figure 2:
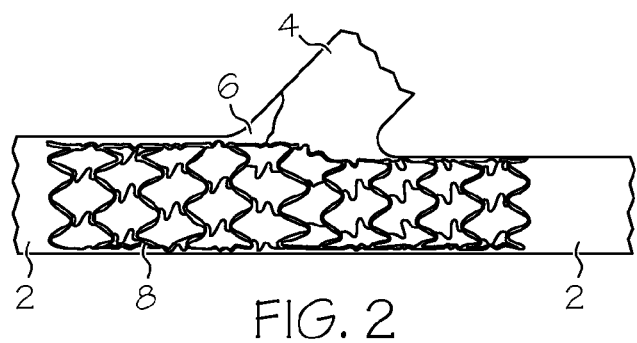
FIGS. 2-4 are illustrations of prior art stents implemented at a blood vessel bifurcation.
Figure 3:
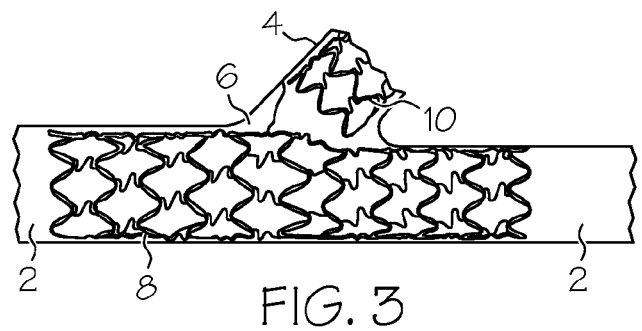
Figure 4:
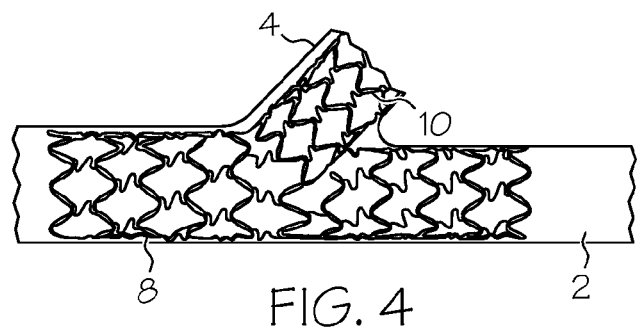

Prior attempts at relieving main vessel 2 and branch vessel 4 from obstruction 6, such as the one depicted in FIG. 1, have been problematic. Referring to FIGS. 2-4, examples of prior methods and structures for stenting an obstructed bifurcation are shown. As shown in FIG. 2, a first stent 8 is introduced into main vessel 2 and an access hole or side opening in the wall of stent 8 is usually created with a balloon to provide access to branch vessel 4 and unobstructed blood flow thereto. Typically, the access hole is created by deforming the struts and connectors of the main stent pattern, which may also deform the area of the stent surrounding the created opening and lead to undesirable results. Also, if stent 8 is used alone, at least a portion of obstruction 6 located within branch vessel 4 is left without stent coverage. Referring to FIGS. 3 and 4, one prior solution has been to introduce a second stent 10 into branch vessel 4, for example via a second catheter inserted through a side opening of first stent 8. As can be seen in FIGS. 3 and 4, such a configuration may introduce additional problems. For example, as shown in FIG. 3, second stent 10 may not provide full coverage of the portion of obstruction 6 in branch vessel 4 due to the angle 11 of the side branch vessel 4 with respect to main vessel 2 and the fact that the ends of the stent typically define a right angle to the longitudinal axis of the lumen. Alternatively, second stent 10 may extend beyond the bifurcation into main vessel 2, as shown in FIG. 4, and cause potential obstruction of blood flow in main vessel 2 and/or cause problems at the overlapping portions of stents 8 and 10.

Figure 5:
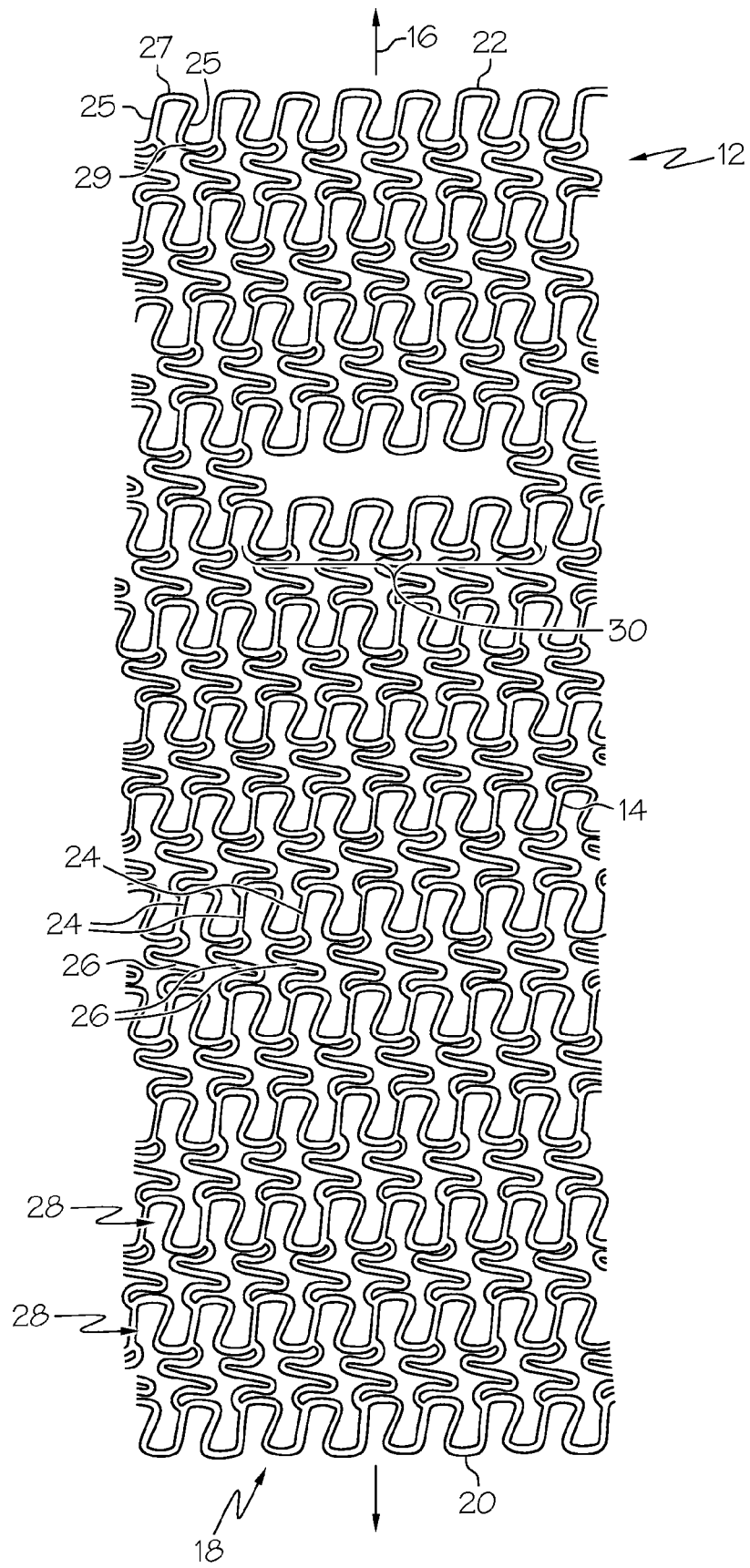
FIG. 5 is a flat view of an embodiment of an unexpanded stent in accordance with the present invention.
Figure 6:
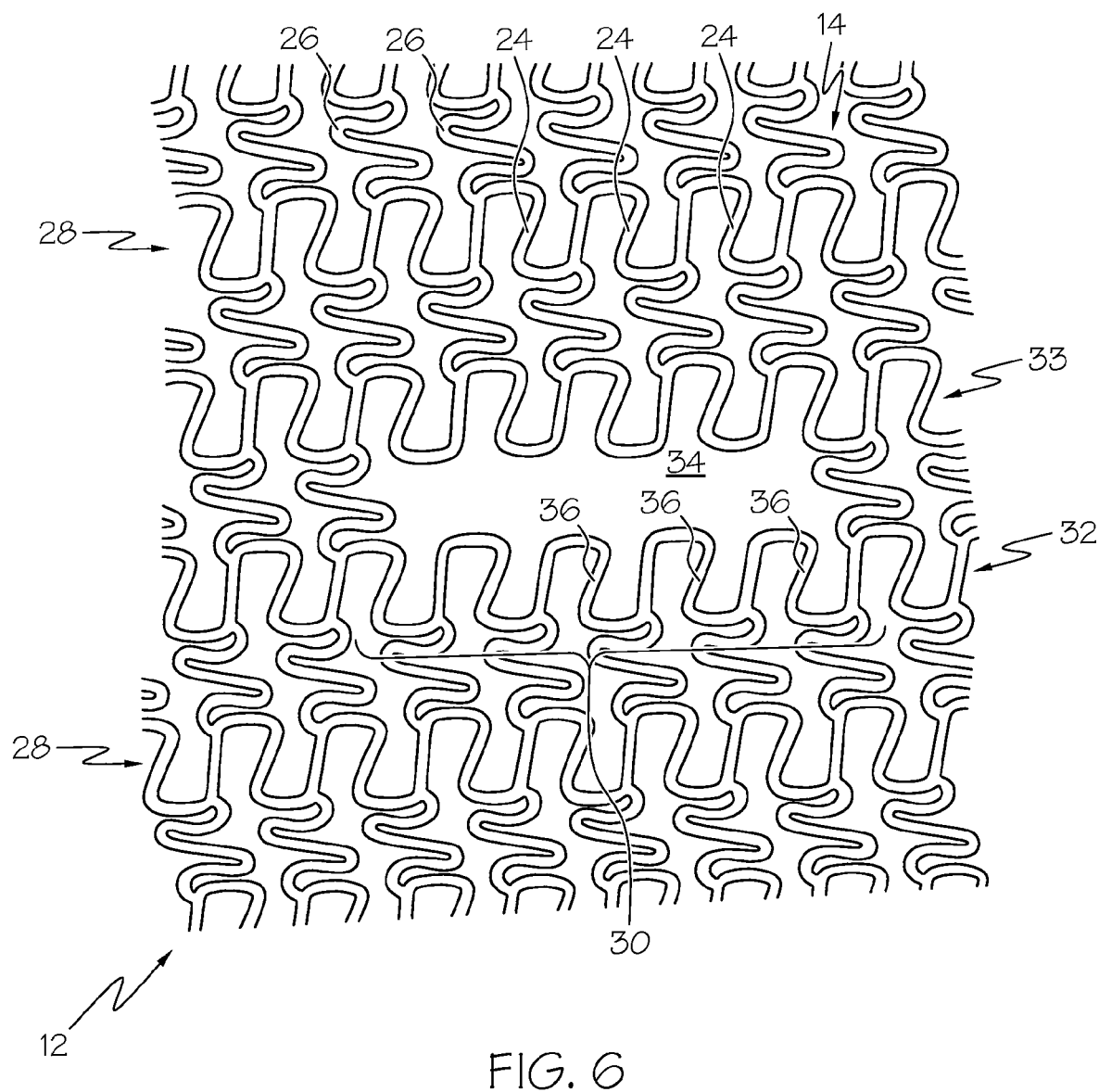
FIG. 6 is an enlarged view of a portion of the unexpanded stent shown in FIG. 5.
Figure 7:
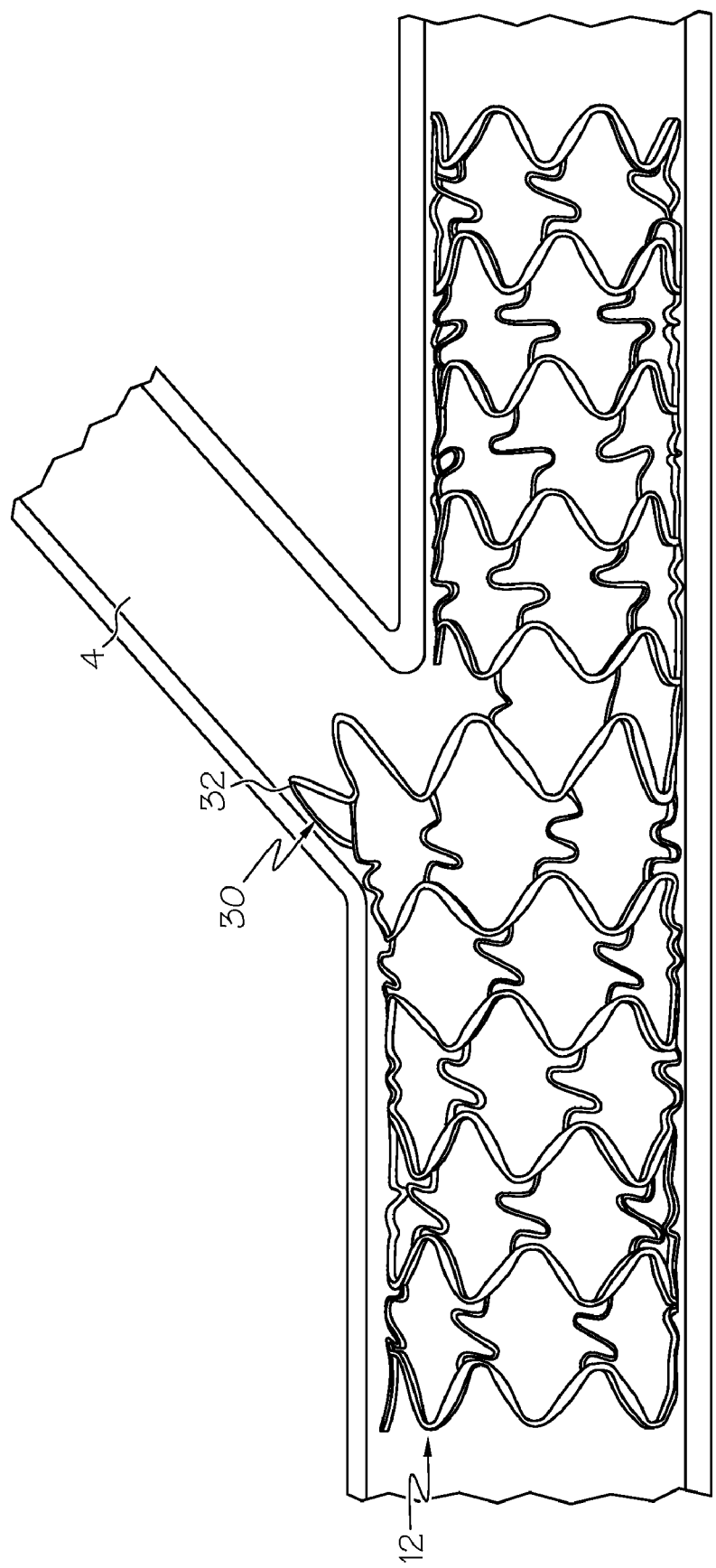
FIG. 7 is a perspective view of the expandable branch portion of the stent of FIG. 5 in the expanded configuration.

Referring now to FIGS. 5-7, a stent 12 according to one embodiment of the present invention comprises stent body or wall 14 extending along a longitudinal axis 16 from a proximal end 20 to a distal end 22 and defining a lumen 18 therein. Stent 12 may have a three-dimensional geometrical configuration having variable dimensions (length, width, height, depth, thickness, etc.). In a preferred embodiment, stent body 14 is a generally tubular structure. As defined herein, "tubular" can include an elongate structure that has varied cross-sections and does not require that the cross-section be circular. For example, the cross-section of stent wall 14 may be generally oval. In an alternate embodiment, stent body 14 is generally cylindrical. Also, the stent body 14 may have varied cross-sectional shapes along the longitudinal axis 16 of the stent. For example, the circumferences in the proximal and distal parts of the stent may be different. This may occur, for example, if during stent delivery the delivery system causes the stent to distend. Lumen 18 represents the inner volumetric space bounded by stent body 14. In a preferred embodiment, stent 12 is radially expandable from an unexpanded state to an expanded state to allow the stent to expand radially and support the main vessel. In the unexpanded state, stent body 14 defines a lumen 18 having a first volume, and in the expanded state, stent body 14 defines a lumen 18 having a second volume larger than the first volume.

FIG. 5 shows stent 12 in an unexpanded state in a flattened elevational view. As shown in FIG. 5, stent body 14 has a generally cellular configuration and comprises a generally repeatable series of struts 24 and connectors 26 configured in a predetermined general, overall, or main pattern along the length of stent 12. Struts 24 comprise a pair of longitudinal strut portions 25 joined by a curved portion 27 at the proximal ends. Struts 24 are interconnected by curved portion 29 at the distal ends and formed into rings 28 that extend about the circumference of stent 12. A series of the circumferential rings 28 are spaced apart from one another longitudinally along the entire length of stent 12, and connectors 26 connect rings 28 to each other longitudinally. Connectors 26 extend generally longitudinally between adjacent circumferential rings 28 and connect to the respective curved portions 27, 29 of longitudinally adjacent struts 24 of adjacent rings 28. In a preferred embodiment, connectors 26 are generally S-shaped or zigzag-shaped, although other patterns may also be used. Details of patterns that may be used for stent 12 are described more fully in co-pending PCT application IL02/00840, filed Oct. 20, 2002, incorporated herein by reference in its entirety. Furthermore, many other strut and connector patterns may be used, and the present pattern is shown for illustration purposes only.

Stent 12 further includes a branch portion 30 located at some point along the length of stent 12. Branch portion 30 comprises a section or portion of stent wall 14 that is configured to extend into a branch vessel in a vessel bifurcation. In general, branch portion 30 is configured to be movable from an unextended position to an extended position. In the unextended position, branch portion 30 is disposed in the volume defined by the unexpanded stent 12, that is, the branch portion 30 does not protrude radially from stent wall 14. In the extended position, the branch portion 30 extends outwardly from stent wall 14 and branch portion 30 is extended into the branch vessel. As best seen in FIG. 6, branch portion 30 comprises a stent wall section of stent body 14 that is initially flush, coplanar, or cocylindrical with the remainder of stent body 14 and may extend outwardly with respect to the remainder of stent body 14. In this regard, branch portion 30 is generally adjacent an opening, slit, space, void, or other incongruity in the overall or main pattern of stent body 14. This configuration allows for access into a branch vessel, and at the same time allows for circumferential alignment of the stent within the vessel prior to deployment. In other embodiments, multiple branch portions can be incorporated into the stent to permit multiple access to one or more vessels. In a preferred embodiment, branch portion 30 may be positioned in the midsection of stent 12. In alternate embodiments, branch portion 30 may be positioned anywhere along the length of stent 12.

As best seen in FIG. 6, in a first embodiment, branch portion 30 comprises a portion of branch ring 32 and is positioned adjacent and proximal to an opening 34. Upon extension of branch portion 30, the portion of branch ring 32 adjacent opening 34 extends into the branch vessel, whereas the circumferential ring 28 adjacent branch ring 32 does not extend into the branch vessel. Opening 34 is formed by an absence of at least one connector 26 adjoining branch ring 32 with a branch opposing ring 33. In some embodiments, four adjacent connectors are absent; however, in alternate embodiments any number of connectors may be absent to create opening 34. In this embodiment, branch ring 32 is substantially similar geometrically to circumferential rings 28 and comprises branch ring struts 36 substantially similar to struts 24; however, a plurality of adjacent struts are free from connectors 26 adjacent opening 34. In this regard, branch ring 32 is at least partially detachable from stent body 14 to facilitate at least a portion of branch ring 32 to extend outwardly with respect to stent body 14. In some embodiments, the geometry of branch ring 32 may vary with respect to circumferential rings 28, and branch ring struts 36 may have different configurations than struts 24.

When stent 12 is expanded, as shown in FIG. 7, branch portion 30 is extended into the branch vessel, causing a portion of branch ring 32 to at least partially cover the inner surface of the branch vessel 4. Thus, in a preferred embodiment, the stent coverage in the branch vessel includes at least partial coverage of the proximal side of the inner branch vessel wall.

Various alternative embodiments provide varying geometries of branch portion 30. For example, branch ring 32 may vary with respect to circumferential rings 28, and branch ring struts 36 may have different configurations than struts 24. In one alternate embodiment, branch ring struts 36 are longer than struts 24. In another embodiment, branch ring struts 36 are more closely packed circumferentially, resulting in a greater number of branch ring struts 36 per area within branch ring 32 as compared to circumferential rings 28. In another embodiment, branch ring struts 36 may be thinner than struts 24. In yet another embodiment, branch ring struts 36 may be made of a different material than struts 24.

Figure 8:
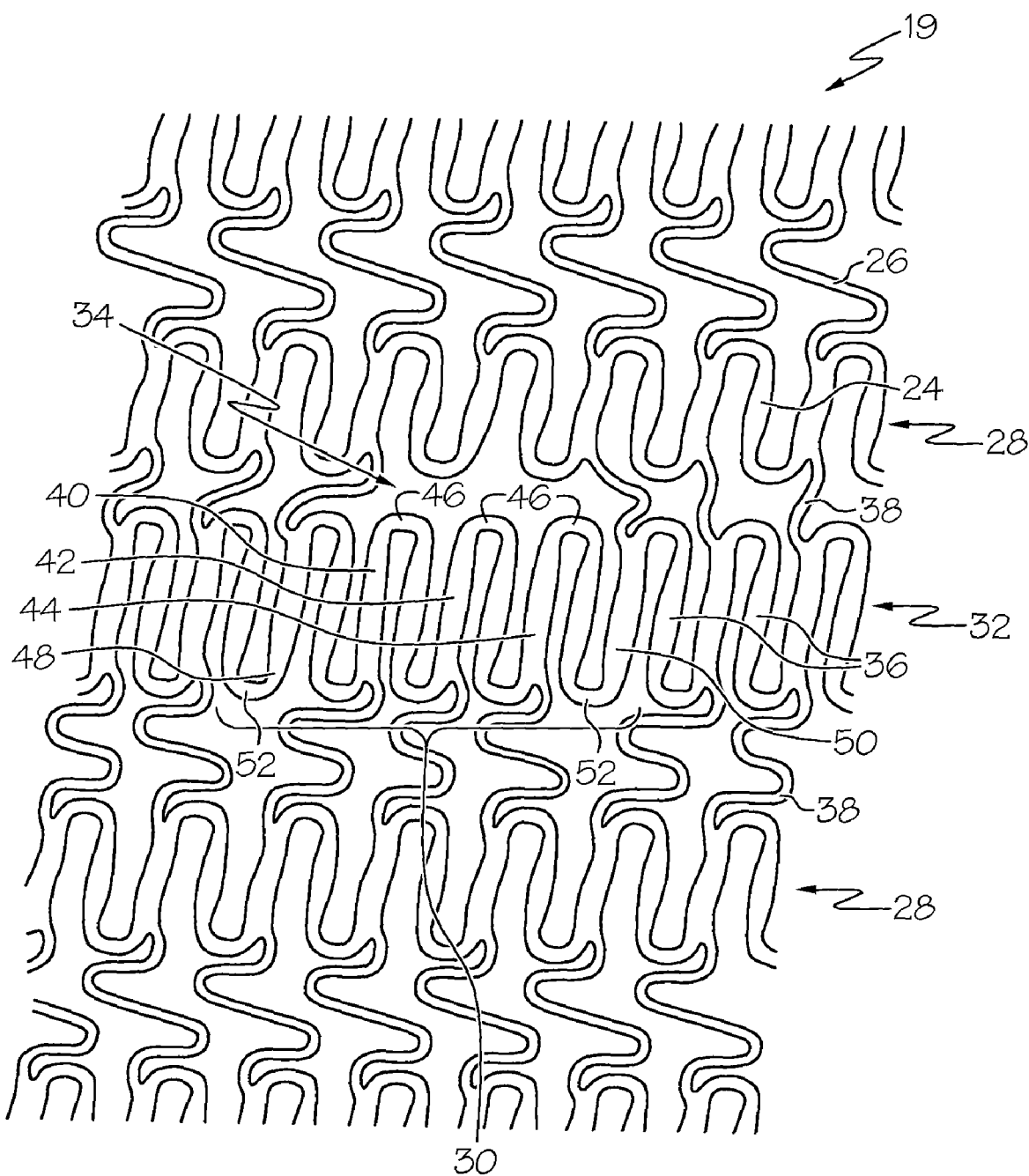
FIG. 8 is an enlarged view of a portion of another embodiment of a stent according to the present invention.

Referring to FIG. 8, another alternate embodiment of stent 19 is shown wherein a branch portion 30 comprises a branch ring 32 having branch ring struts 36 that are longer than struts 24 and a greater number of branch ring struts 36 provided as compared to the number of struts 24 in circumferential rings 28, resulting in a more closely packed branch ring 32. Furthermore, the number of branch ring connectors 38 on both sides of branch ring 32 is lower per branch strut 36 than the number of connectors 26 per strut 24. Opening 34 is adjacent branch ring 32 on a distal side thereof, and the distal ends 46 of at least one, and preferably a plurality, of branch ring struts 40, 42, 44 are free from connectors and detachable from stent body 14. In this embodiment, two branch ring struts 48 and 50 positioned laterally adjacent struts 40, 42, and 44 have proximal ends 52 free from connectors. In this regard, free proximal ends 52 provide less resistance to movement of branch ring 32 during outward expansion with respect to stent body 14. This same procedure can be used to provide one, two, three or more proximal ends in the ring free of connectors. Additionally, the shape and configuration of branch ring connectors 38 is different than those of connectors 26. For example branch ring connectors along the proximal side of branch ring 32 are longer than connectors 26 to facilitate greater expansion of branch portion 30 into a vessel side branch. Also, branch ring connectors along the distal side of branch ring 32 are shaped and oriented differently than connectors 26 to facilitate greater expansion of branch portion 30 into the branch vessel. In alternate embodiments, branch ring connectors 38 may also differ among themselves. Also, the longer branch ring struts 36 are generally more flexible than comparable shorter struts because the added length permits more deflection. Also, the added length permits greater coverage vessel wall coverage due to deeper penetration into the branch vessel during extension. In alternate embodiments, different geometries and orientations of branch ring connectors 38 may be used.

Figure 9:
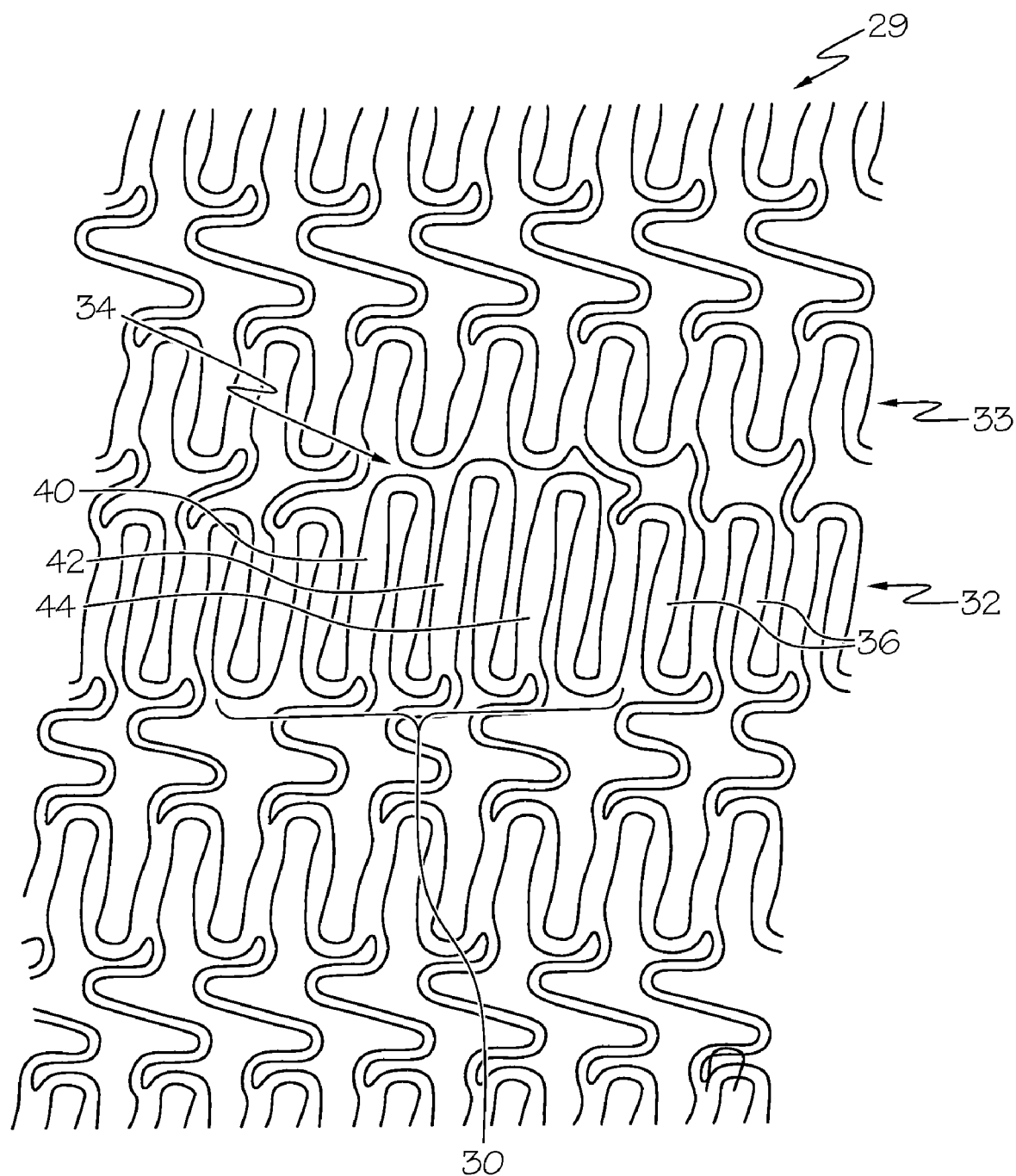
FIG. 9 is an enlarged view of a portion of an alternative embodiment of a stent according to the present invention.

Referring to FIG. 9, another alternate embodiment of stent 29 is shown having a branch portion 30 similar to that of the embodiment of FIG. 8, except branch ring struts 40, 42, and 44 are longer than the other branch ring struts 36, and the distal ends thereof define an arcuate profile to the proximal side of opening 34. Also, central strut 42 is longer than struts 40, 44 adjacent to strut 42. In this regard, when branch portion 30 is extended, struts 40, 42, and 44 extend further into the branch vessel and provide more coverage of the vessel wall than the embodiment depicted in FIG. 8. In this regard, this embodiment may more readily cover an obstruction in a bifurcation vessel such as the one depicted in FIG. 1 and, therefore, may provide better blood flow to a branch vessel. Furthermore, as described in more detail below, this embodiment facilitates the use of a second stent in the branch vessel.

Figure 10:
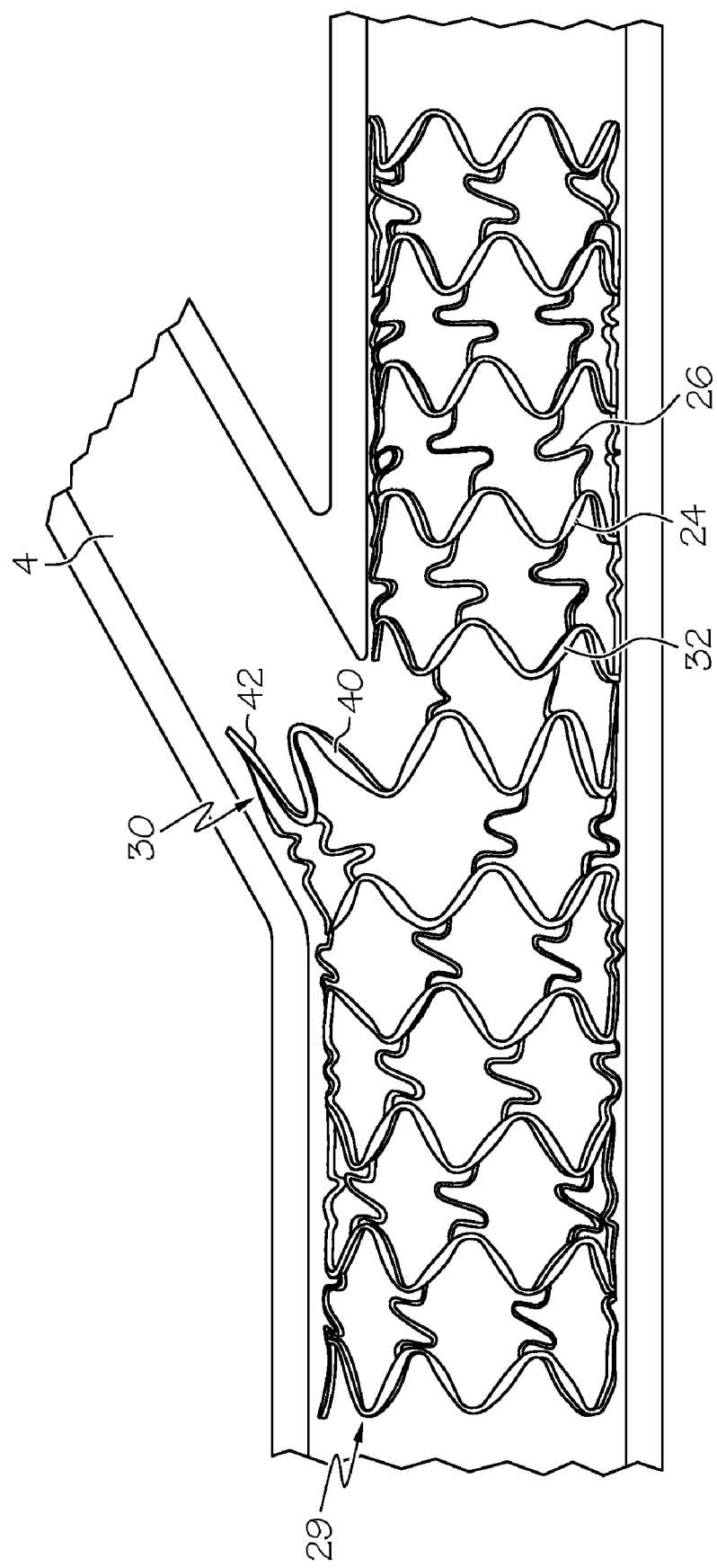
FIG. 10 is a perspective view of the expandable branch portion of the stent of FIG. 9 in the expanded configuration.

Referring to FIG. 10, stent 29 of FIG. 9 is shown in an expanded state with branch portion 30 extended into the branch vessel, causing branch ring 32 to at least partially cover the inner surface of the branch vessel on the proximal side. The distal end of strut 42 of branch ring 32 extends further into the branch vessel than the distal ends of struts 40, 44 because strut 42 is longer in this embodiment than adjacent struts 40, 44. In this regard, a generally tapered, straight or linear profile along the distal perimeter of branch portion 30 is created when branch portion 30 is expanded into the branch vessel.

Figure 11:
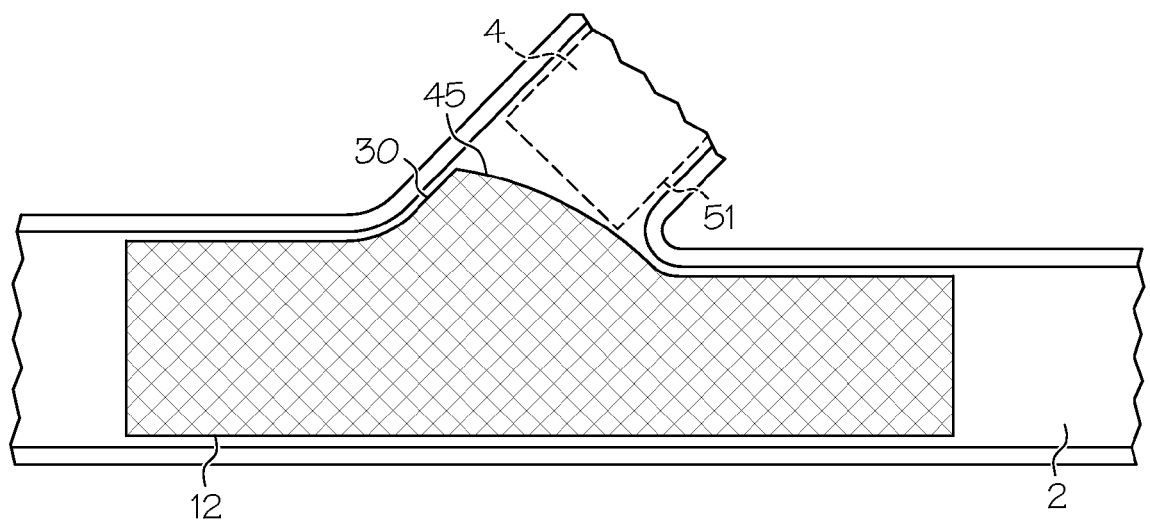
FIG. 11 is a schematic view of the stent of FIG. 5 in the expanded state implemented at a blood vessel bifurcation.
Figure 12:
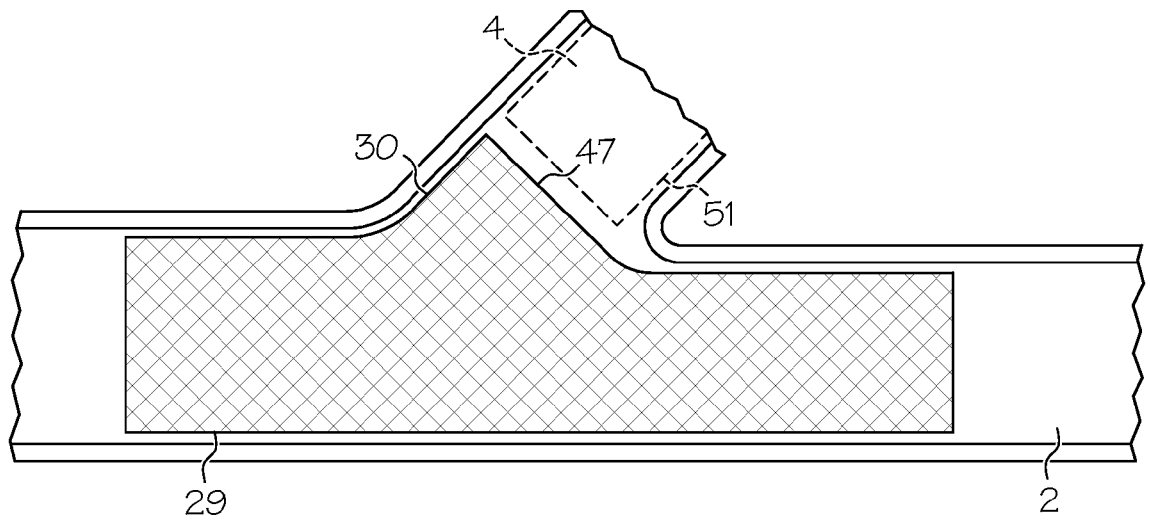
FIG. 12 is a schematic view of the stent of FIG. 9 in the expanded state implemented at a blood vessel bifurcation.

Referring to FIGS. 11 and 12, schematic views are shown of stents 12, 29 of FIGS. 5 and 9, respectively, in the expanded state as implemented at a blood vessel bifurcation. As shown in FIG. 11, stent 19 of the embodiment of FIG. 8 has a generally curved or radial profile along the distal perimeter 45 of branch portion 30 as it extends into branch vessel 4. The generally curved or radial profile is due to the particular geometry of branch portion 30 of stent 19 of the embodiment of FIG. 8. In particular, because all of the branch ring struts 36 of branch ring 32 are of equal length in this embodiment, the distal ends of struts 36 radially expand equidistantly into branch vessel 4, thereby creating a generally curved or radial profile along the distal perimeter 45 of branch portion 30. Referring to FIG. 12, stent 29 of the embodiment of FIG. 9 has a generally tapered, straight or linear profile along the distal perimeter 47 of the branch portion 30 of the stent as it extends into branch vessel 4. The generally straight or linear profile in FIG. 12 is a result of the particular geometry of branch portion 30 of stent 29 of the embodiment of FIG. 9. In particular, because central strut 42 of branch ring 32 is longer in this embodiment than struts 40, 44 adjacent to strut 42, the distal end of strut 42 extends further into branch vessel 4 than the distal ends of struts 40, 44, as best seen in FIG. 10, thus creating a generally tapered, straight or linear profile along the distal perimeter 47 of branch portion 30. In a preferred embodiment, the linear profile is at a right angle with respect to the axis of branch vessel 4. In alternative embodiments, however, the linear profile may be at any angle with respect to the axis of branch vessel 4. One advantageous feature of the linear profile along the distal perimeter 47 of branch portion 30 shown in FIG. 12 is that if a second stent 51 were to be used in branch vessel 4, the linear profile facilitates better alignment with the second stent and permits coverage of a larger surface area of the branch vessel wall. For example, if a second stent 51 were to be used in combination with stent 12 of FIG. 11, gaps may exist between the two stents at the interface between the radial distal perimeter 45 and an abutting straight or linear edge of a second stent, whereas a close abutting interface may be achieved with stent 29 of FIG. 12.

Figure 13:
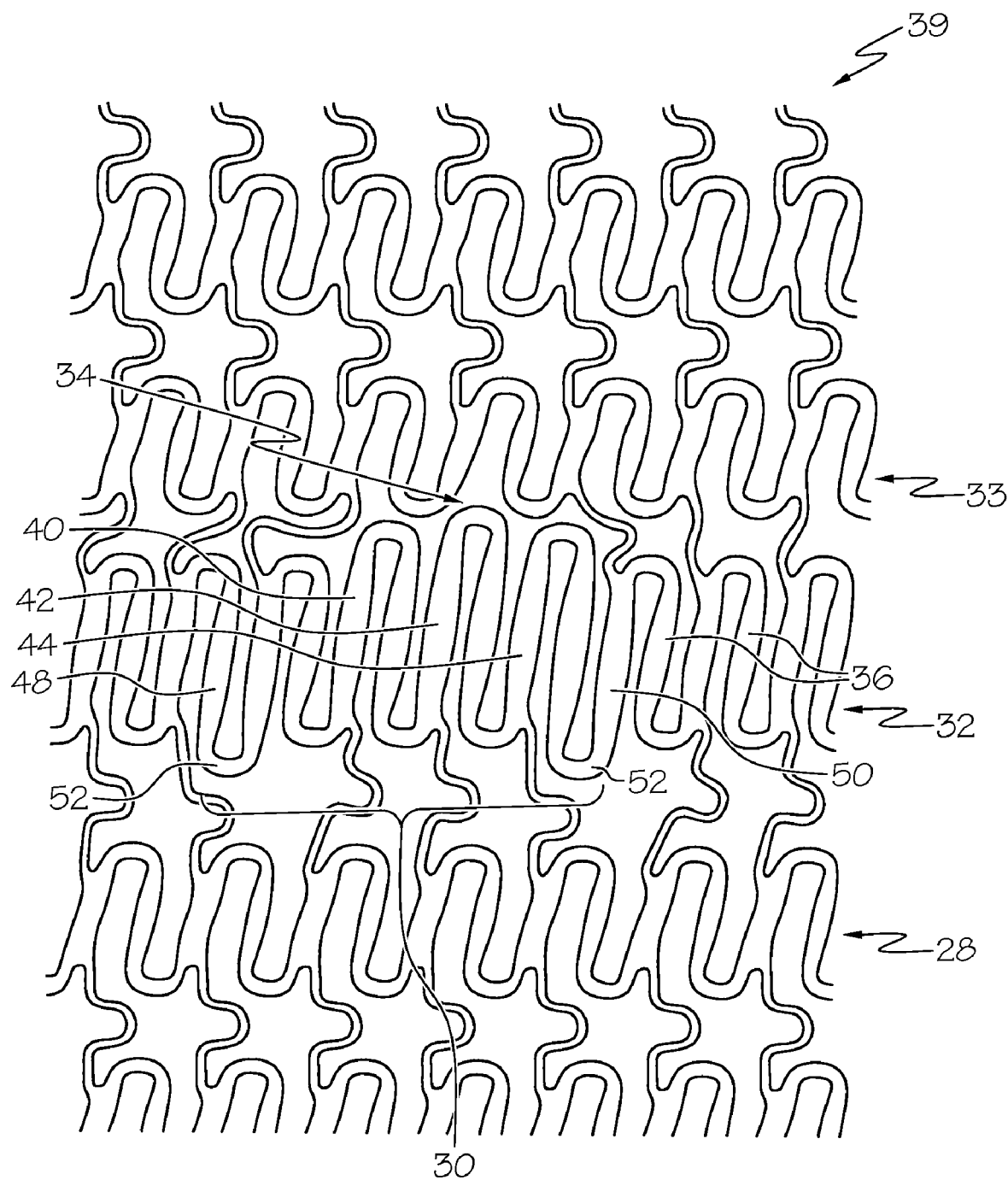
FIG. 13 is an enlarged view of a portion of another embodiment of a stent according to the present invention.

Referring to FIG. 13, another embodiment of stent 39 is shown having an alternative embodiment of a branch portion 30 similar to that of the embodiment of FIG. 9, except lateral branch ring struts 48 and 50 are longer than the other branch ring struts 36, and the proximal ends 52 of branch ring struts 48, 50 extend proximally beyond the other branch ring struts into a space between the branch ring 32 and the adjacent circumferential ring 28. Branch struts 48, 50 have proximal ends 52 free from connectors and provide less resistance to movement of branch ring 32 during outward expansion with respect to stent body 14. In this regard, the longer lateral branch ring struts 48, 50 function similar to a hinge and further facilitate extension of branch ring portion 30 outwardly, which may accommodate a branch vessel disposed at a greater angle 11 (FIG. 1) as compared to stent 29 of the embodiment of FIG. 9. Again, since struts 40, 42, and 44 are longer than branch ring struts 36, they are more flexible and provide more coverage of a vessel wall than the embodiment depicted in FIG. 8.

Figure 14:
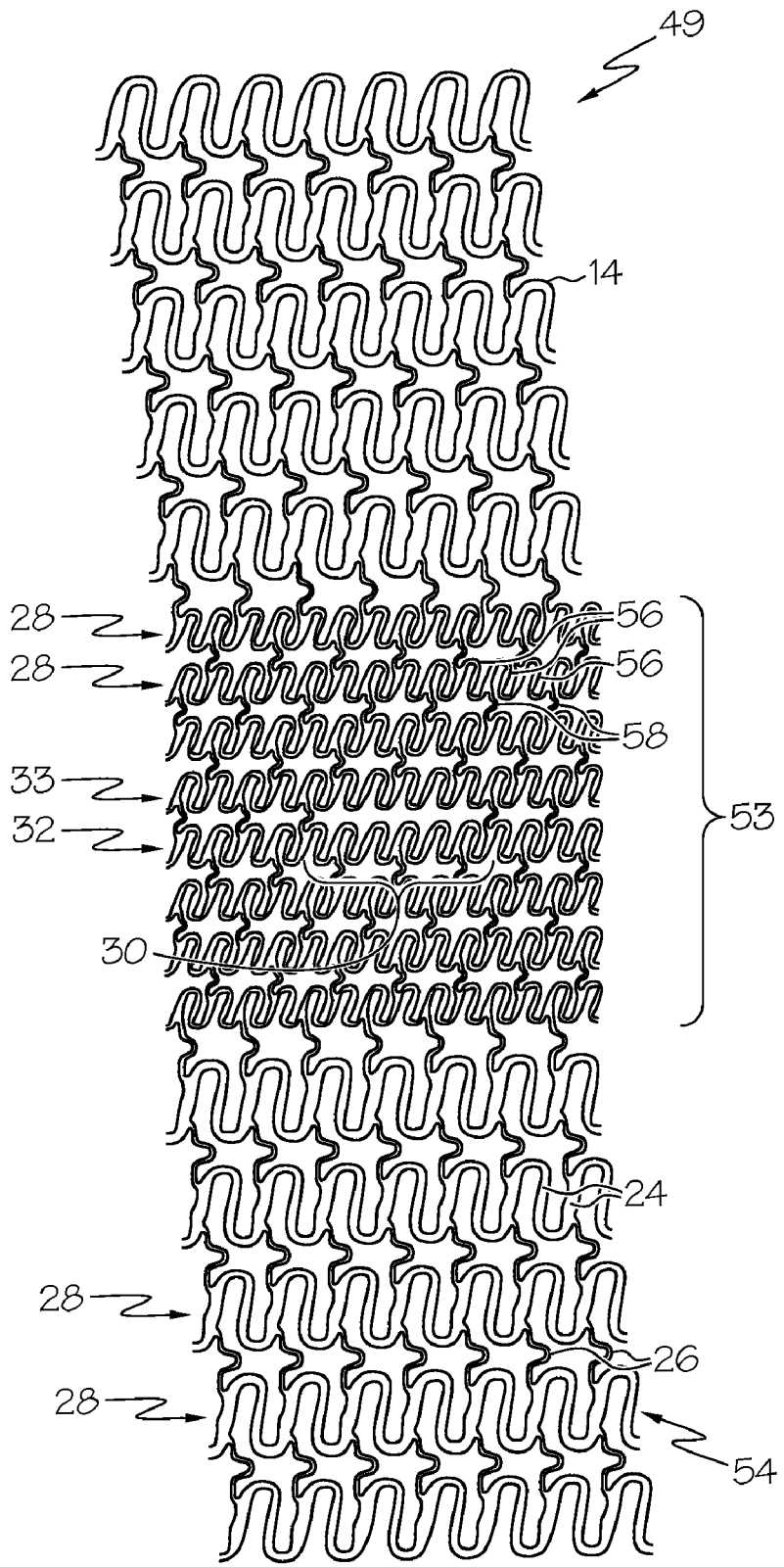
FIG. 14 is a flat view of another embodiment of an unexpanded stent in accordance with the present invention.
Figure 15:
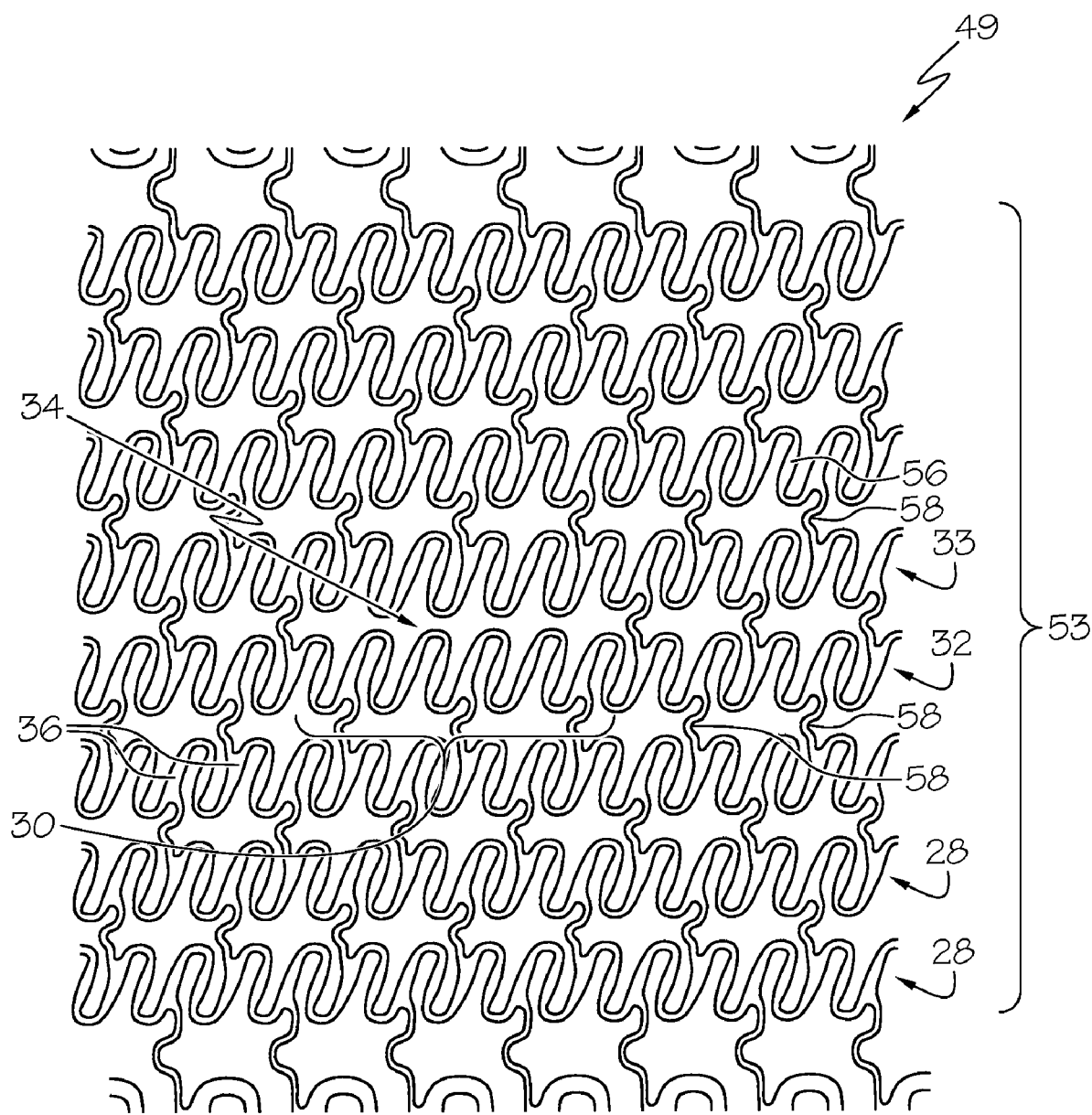
FIG. 15 is an enlarged view of a portion of the unexpanded stent shown in FIG. 14.

Referring now to FIGS. 14 and 15, another embodiment of stent 49 is shown having a stent body 14 that has a longitudinal section 53 that has a different pattern than main pattern 54. Longitudinal section 53 comprises a generally repeatable series of struts 56 and connectors 58 that are smaller in dimension than struts 24 and connectors 26, but are formed into a similar geometrical pattern as main pattern 54. In this regard, the struts 56 are more numerous per area within rings 28, and rings 28 are more numerous per area in section 53 because the length of struts 56 is shorter than the length of struts 24 and the length of connectors 58 is shorter than the length of connectors 26. In a preferred embodiment, the same number of connectors 58 extend between adjacent rings 28; however, because the struts are more numerous in longitudinal section 53, connectors 58 extend longitudinally between every other strut of adjacent rings 28. As shown in FIG. 15, stent 49 further includes a branch portion 30 positioned within section 53. Branch portion 30 comprises a branch ring 32 adjacent an opening 34. Opening 34 is formed by an absence of at least one connector 26 adjoining branch ring 32 with branch opposing ring 33. In a preferred embodiment, two adjacent connectors are absent; however, in alternate embodiments any number of connectors may be absent to create opening 34. In this embodiment, branch ring 32 is substantially similar geometrically to circumferential rings 28 and comprises branch ring struts 36 substantially similar to struts 56; however, a plurality of adjacent struts are free from a connectors 58 adjacent opening 34 and branch ring 32 is at least partially detachable from stent body 14 at opening 34 to facilitate at least a portion of branch ring 32 to extend outwardly with respect to stent body 14. The generally smaller struts and connectors of longitudinal section 53 provide for freer movement of the strut and connector material and facilitate conformance to a vessel wall. The smaller struts and connectors also provide for a relatively more dense surface area coverage of the branch vessel wall, which may be advantageous in achieving a more uniform coverage around the ostium. In particular, this embodiment may provide particularly advantageous coverage of a geometrically complex obstruction in a bifurcation vessel since the relatively small pattern may flex or contour around the obstruction and provide coverage therefor. Also, this embodiment is advantageous for relatively small obstructions as the smaller pattern may cover more surface area of obstruction.

Figure 16:
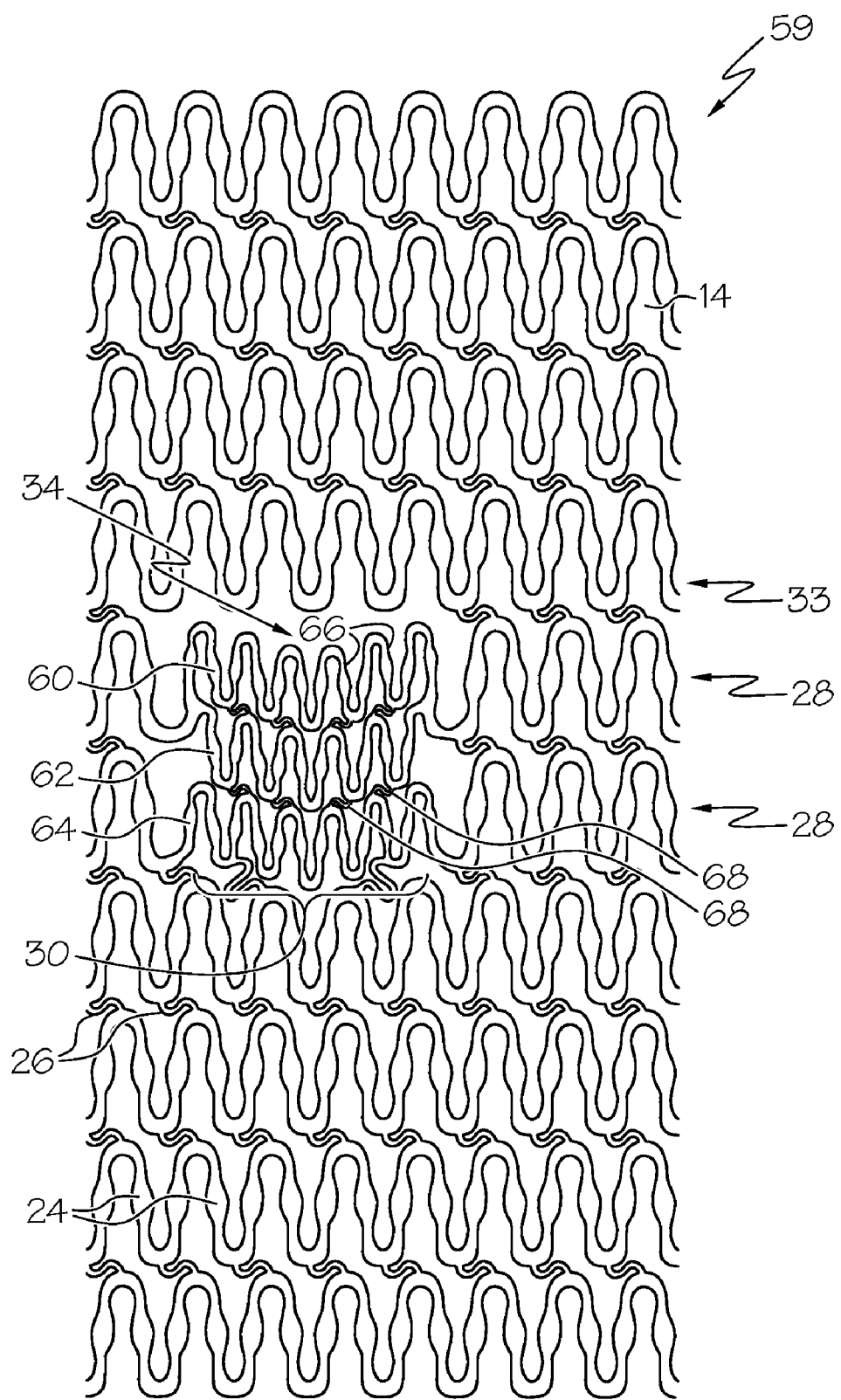
FIG. 16 is a view of a portion of another embodiment of a stent according to the present invention.

Referring to FIG. 16, another embodiment of stent 59 is shown and includes an alternate branch portion 30 comprising a portion of three adjacent branch ring sections 60, 62, 64 connected and extending circumferentially from two adjacent circumferential rings 28. Branch ring sections 60, 62, 64 each includes a plurality of branch struts 66 and are connected in the longitudinal direction by branch connectors 68. Struts 66 are shorter longitudinally than struts 24 of rings 28 and connectors 68 are smaller than connectors 26. The distal ring 60 is adjacent opening 34 and the distal ends of struts 66 of ring 60 are detachable from stent body 14 at opening 34 to permit extension of at least a portion of branch ring sections 60, 62, 64 to expand outwardly with respect to stent body 14. In this embodiment, the three branch ring sections 60, 62, 64 may extend outwardly in a more radial fashion and this branch portion 30 may be particularly advantageous for adapting or conforming to the shape of the proximal side of the ostium. Furthermore, the branch portion of this embodiment may more readily extend or flex around an obstruction in a bifurcation vessel such as the one depicted in FIG. 1 while providing branch wall coverage and better blood flow to the branch vessel.

Figure 17:
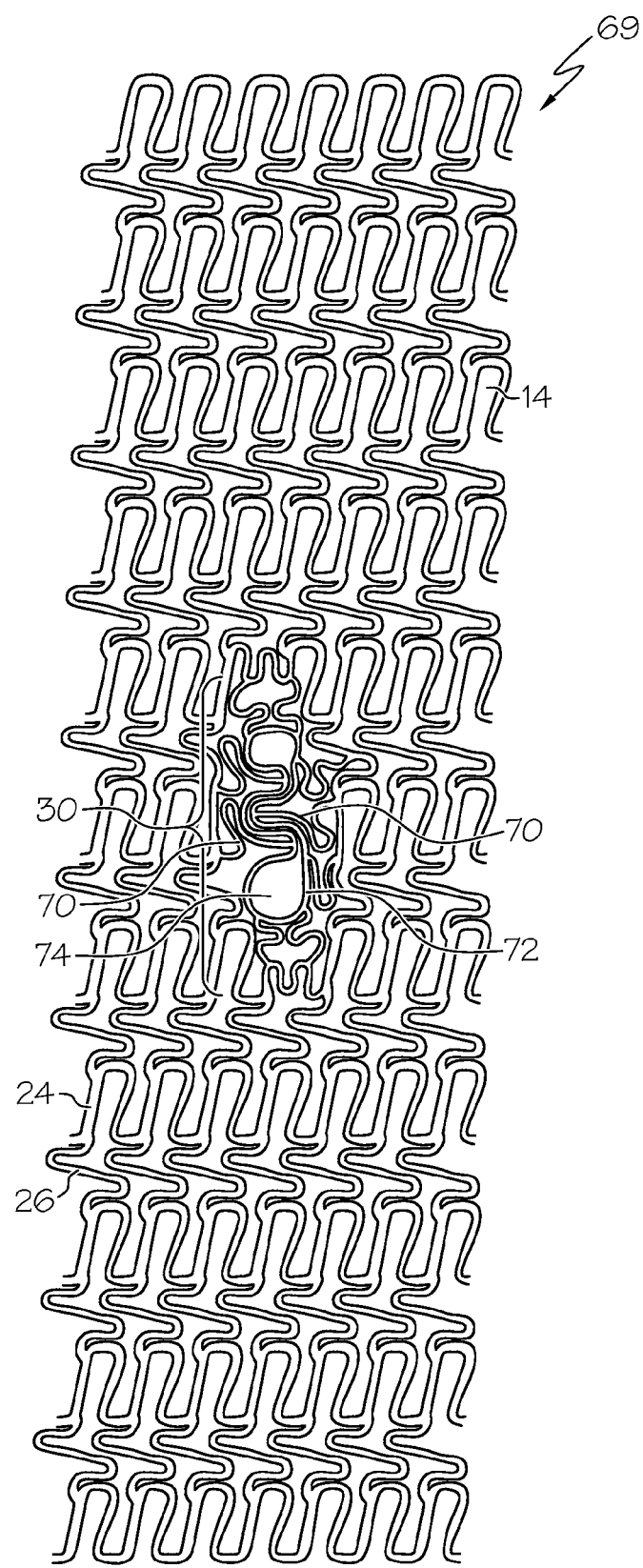
FIG. 17 is a flat view of another embodiment of an unexpanded stent in accordance with the present invention.
Figure 18:
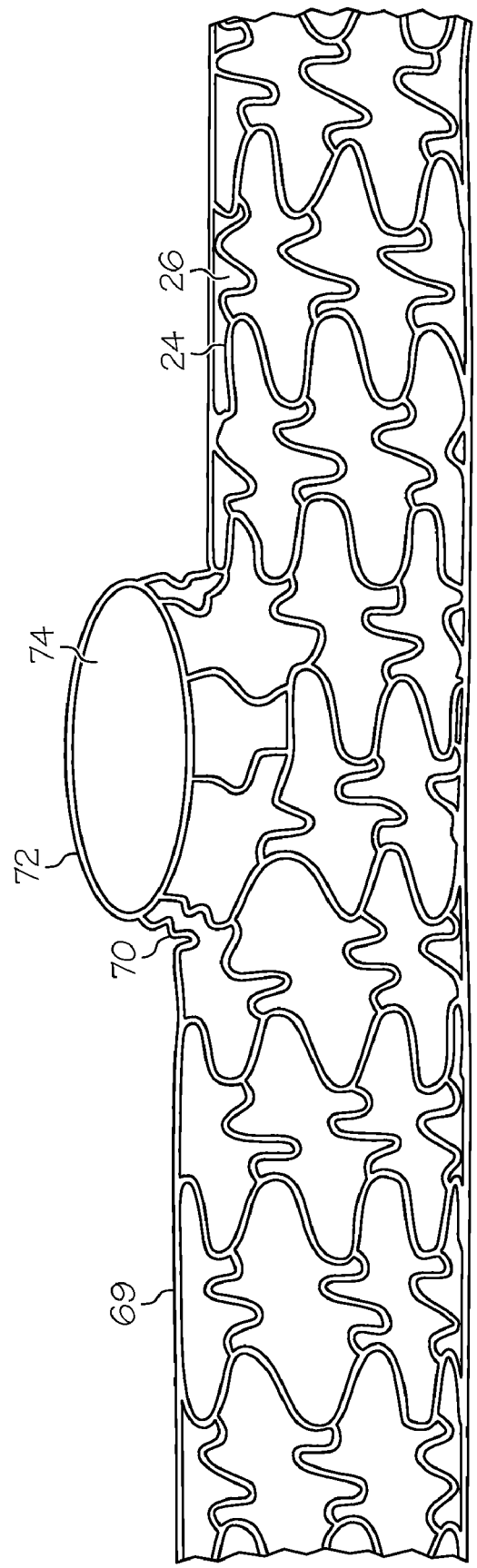
FIG. 18 is a perspective view of the expandable branch portion of the stent of FIG. 17 in the expanded configuration.

Referring to FIGS. 17 and 18, an alternate embodiment of stent 69 is shown and includes an alternate branch portion 30. In this particular embodiment, branch portion 30 comprises support struts 70 and an expandable ring 72. Branch portion 30 defines at least one side opening 74. In one embodiment, the dimensions of the cell defining side opening 74 are such that the side opening 74 (prior to expansion of the stent) is larger than other openings in stent body 14. The presence of side opening 74 is generally configured to accommodate a side sheath therethrough and allow a physician to access a branch vessel during or after a procedure. In a particular embodiment, as shown in FIG. 17, side opening 74 is surrounded by expandable ring 72 of continuous material. In alternative embodiments, expandable ring 72 comprises unattached portions, or one portion that only partially covers side opening 74. A series of support struts 70 connect expandable ring 72 with struts 24 and connectors 26. Support struts 70 preferably comprise patterns in a folded or wrap-around configuration that at least partially straighten out during expansion, allowing expandable ring 72 to protrude into the branch vessel.

In this embodiment, when stent 69 is expanded, as shown in FIG. 18, branch portion 30 is extended into the branch vessel, causing expandable ring 74 to at least partially cover the inner surface of the branch vessel. Thus, in a preferred embodiment, the stent coverage in a portion the branch vessel includes the full circumference of the inner branch vessel wall. In alternative embodiments, partial coverage or several sections of coverage are present.

Figure 19:
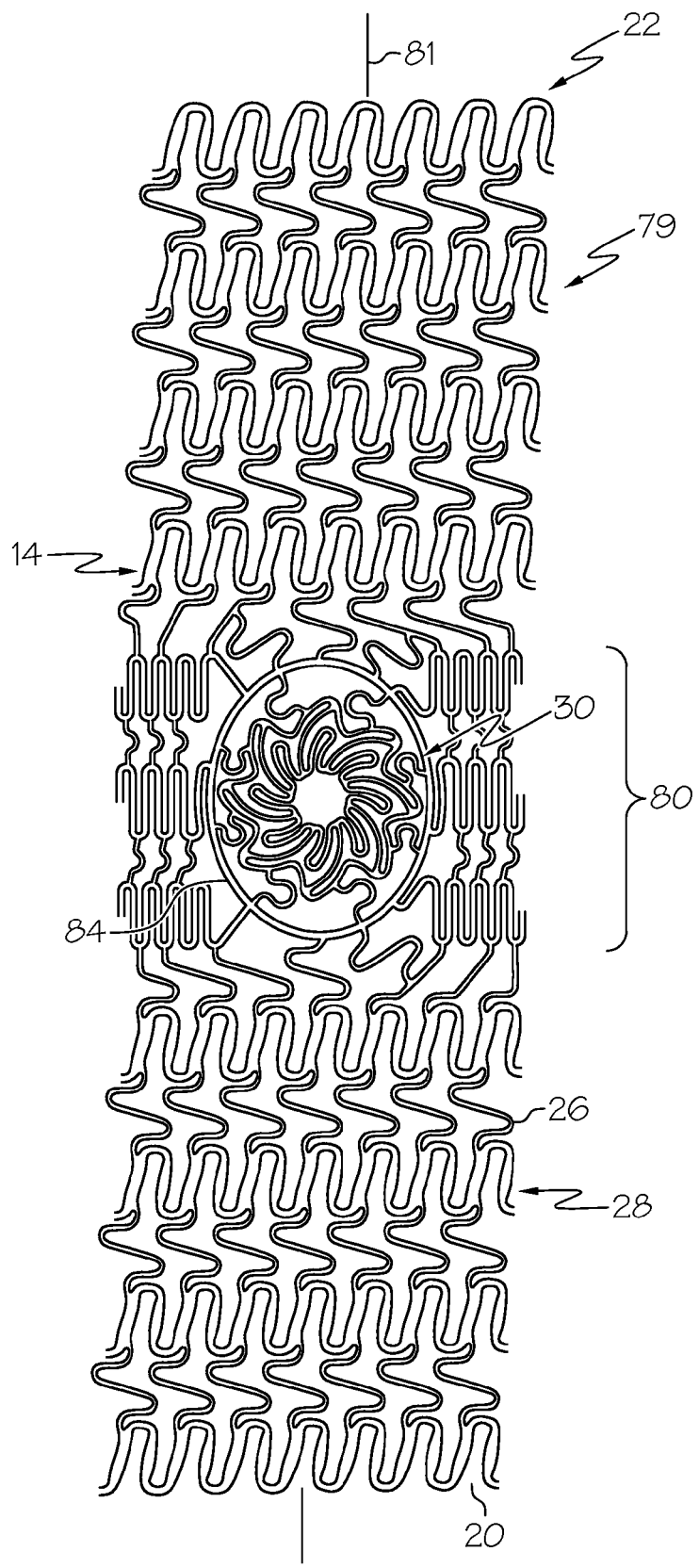
FIG. 19 is a flat view of another embodiment of an unexpanded stent in accordance with the present invention.
Figure 20:
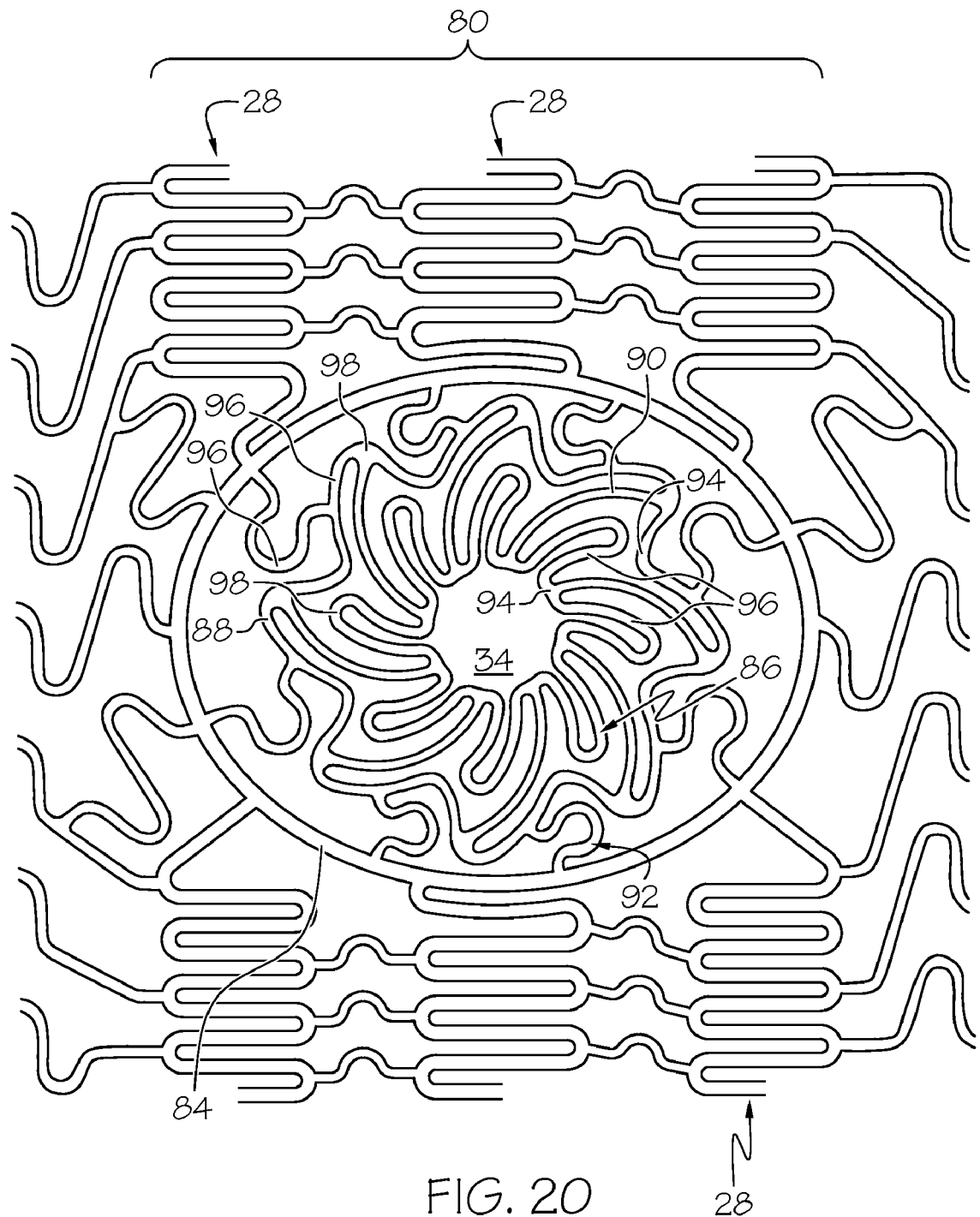
FIG. 20 is an enlarged view of a portion of the stent of FIG. 19.
Figure 21:
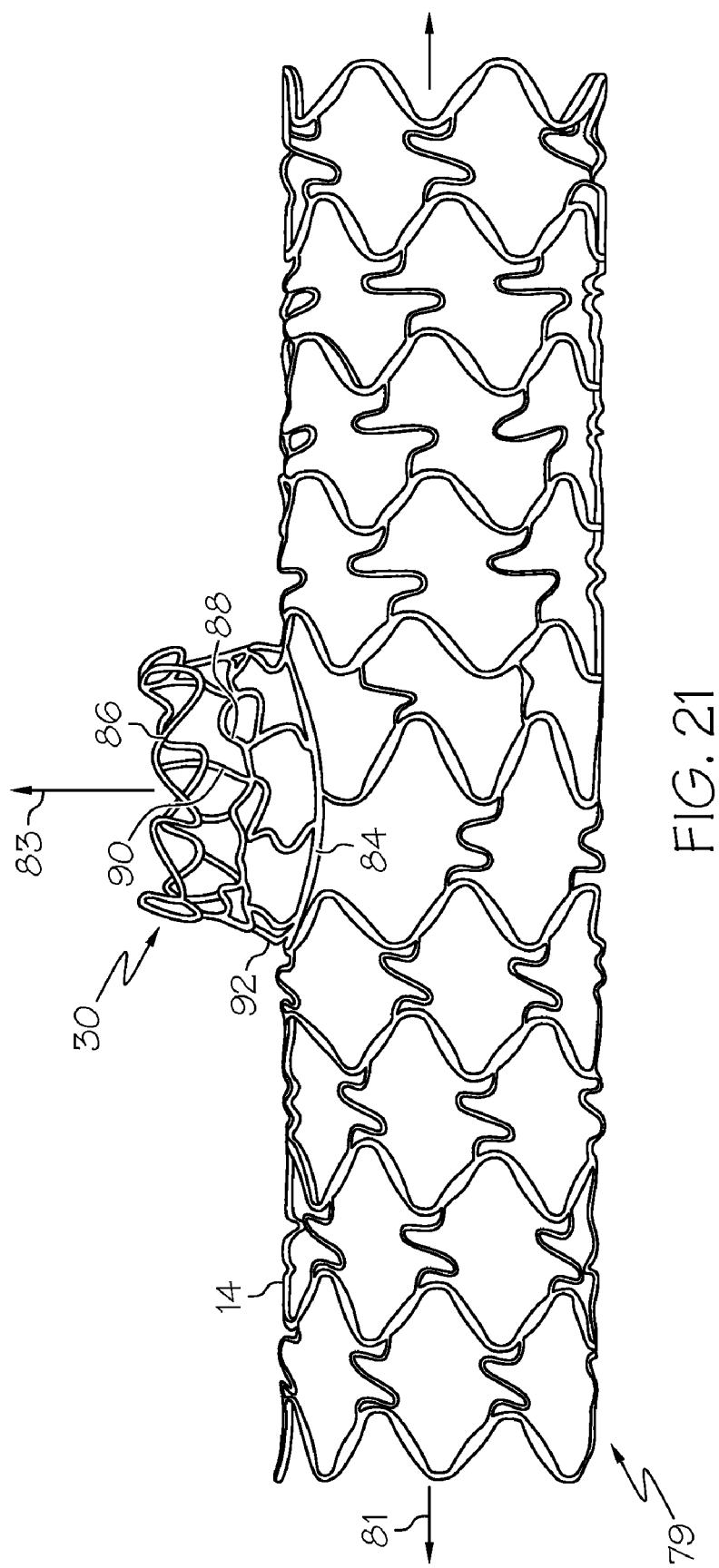
FIG. 21 is a view of the expandable branch portion of the stent of FIG. 19 in the expanded configuration.

Referring to FIGS. 19-21, another embodiment of a stent 79 is shown having a main stent body 14 and another embodiment of a branch portion 30. FIGS. 19 and 20 show stent 79 in the unexpanded condition where branch portion 30 has not been deployed. FIG. 21 shows the stent 79 in the expanded configuration where the branch portion 30 has been expanded. As shown, main stent body 14 includes a main stent pattern having a generally repeatable ring 28 and connector 26 pattern. Branch portion 30 and the surrounding midsection 80 interrupt the repeatable ring 28 and connector 26 pattern of stent 79. In this embodiment, branch portion 30 is configured to be both radially expandable and longitudinally extendable into the branch vessel and relative to the longitudinal branch axis 83 so that, in a preferred embodiment, the branch portion 30 contacts the entire periphery or circumference of the inner wall of the branch vessel in the expanded configuration. In this regard, branch portion 30 preferably provides 360.degree. coverage of the wall of the branch vessel. That is, branch portion 30 can be extended outward with respect to the longitudinal axis 81 of stent 79, and can also be expanded radially about branch axis 83 so as to contact the vessel (thereby allowing it to be adjustable with respect to vessel size).

Referring to FIG. 20, an enlarged view of section 80 of stent 79 is shown. In a preferred embodiment, a structural support member 84 may be provided as a transition between the main stent body 14 and branch portion 30. In one aspect of a preferred embodiment, structural support member 84 may be elliptical to accommodate branch vessels extending at an angle to the main vessel. In alternate embodiment, other shapes of support member 84 can be used to accommodate the vasculature. The structural support member 84 may include a continuous ring. In this embodiment, structural support member 84 is a full, non-expandable ring and it does not expand radially beyond a particular circumference.

As shown in FIGS. 19 and 20, two concentric rings, inner ring 86 and outer ring 88, are positioned within structural support member 84 and surround a generally circular central branch opening 34 to provide access to the side branch vessel when stent 79 is in the unexpanded condition. Rings 86 and 88 are interconnected by a plurality of inner connectors 90. Outer ring 88 is connected to structural support member 84 by a plurality of outer connectors 92. Rings 86 and 88 are generally curvilinear members. For example, rings 86, 88 can be defined by undulation petals, prongs, or peaks 94. In a preferred embodiment, each ring 86, 88 has the same number of undulation peaks 94, but the inner ring 86 may be more closely or tightly arranged, as shown. In another preferred embodiment, each ring 86, 88 has eight petals or undulation peaks 94, although in alternate embodiments each ring can have any number of undulation peaks, and the number of peaks need not be equal for each ring. The undulation peaks 94 generally include a pair of strut portions 96 interconnected by curved portions 98, and the strut portions themselves are connected to adjacent strut portions by another curved portion. In a preferred embodiment, eight outer connectors 92 extend between structural support member 84 and outer ring 88, and each outer connector 92 is attached at one end to approximately the middle of a strut portion 96 of outer ring 88 and the structural support member 84 at the other end. As shown, outer connectors 92 may also have an undulated shape, although in alternate embodiments outer connectors 92 may have differing shapes. In another aspect of the preferred embodiment, outer connectors 92 may be evenly or symmetrically spaced about the structural support member 84. The inner ring 86 is attached to the outer ring 88 by a plurality of inner connectors 90 and, in a preferred embodiment, eight inner connectors 90 connect the rings. Inner connectors 90 extend from curved portion 98 of outer ring 88 to curved portion of inner ring 86. As shown in FIG. 20, in a preferred embodiment, inner connectors 90 have a simple curved shape. Other quantities, configurations, sizes and arrangements of connectors, rings and spacing can be used depending upon the desired results. Varying the connectors can provide for different amounts of flexibility and coverage. The type of configuration of rings and connectors shown addresses the need for radial and longitudinal expansion of branch portion 30, as well as branch vessel coverage. Other configurations and arrangements for the branch portion can be used in accordance with the invention.

Referring again to FIGS. 19 and 20, the stent pattern surrounding branch portion 30 may be modified with a different pattern to accommodate branch portion 30, as can all of the aforementioned embodiments. In particular, the rings 28 in the midsection 80 may be configured and dimensioned to be denser to provide sufficient coverage and flexibility to compensate for the area occupied by branch portion 30.

Referring now to FIG. 21, stent 79 is shown in the expanded configuration, with branch portion 30 deployed. Upon expansion of branch portion 30, the inner and outer rings 86, 88 shift about the longitudinal branch axis 83 and expand laterally away from the main stent body 14 and into the branch vessel to form a branch coverage portion. Upon expansion, the outer connectors 92 can move outwardly and the inner connectors 90 can straighten to a position substantially parallel to longitudinal branch axis 83. In a preferred embodiment, the expanded rings 86, 88 have substantially the same expanded diameter, although in alternate embodiments rings 86, 88 could also have different diameters to accommodate a tapered vessel, if, for example a tapered balloon is used. The branch portion 30 can be extended at different angles to the longitudinal axis 81 of the stent depending upon the geometry of the branch vessel being treated. In this embodiment, the branch portion 30 may preferably extend into the branch vessel about 1.5-3 mm.

Figure 22:
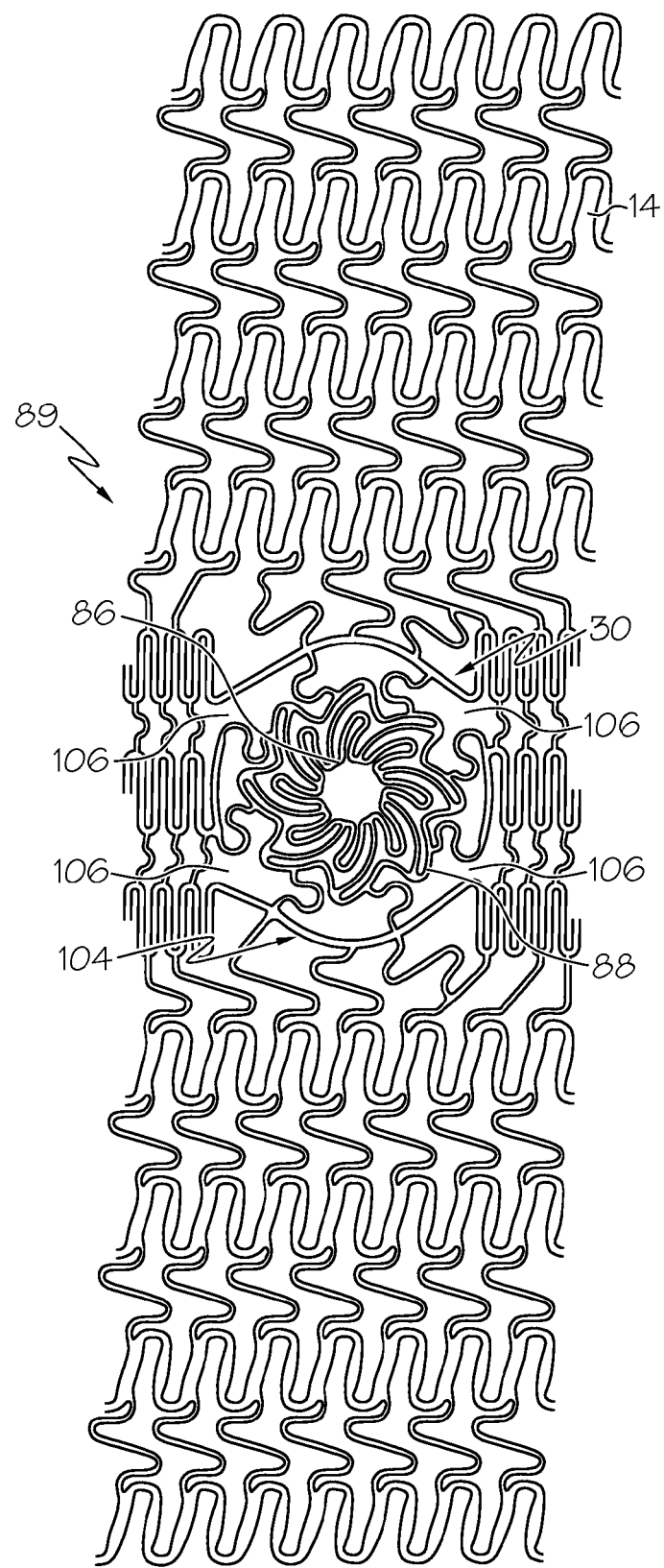
FIG. 22 is a flat view of another embodiment of an unexpanded stent in accordance with the present invention.

Referring now to FIG. 22, another embodiment of a stent 89 is shown having a main stent body 14 and another embodiment of a branch portion 30. Stent 89 is substantially similar to stent 79, except stent 89 has a discontinuous support member 104 surrounding a two concentric ring 86, 88 structure. Support member 104 has a generally elliptical shape and includes a plurality of discontinuities 106 along the perimeter. The configuration of the discontinuous support member facilitates additional flexibility of the branch portion during expansion and generally provides for accommodating a greater range of branch vessel geometries. In one aspect of a preferred embodiment, structural support member 84 may be elliptical to accommodate branch vessels extending at an angle to the main vessel.

Figure 23:
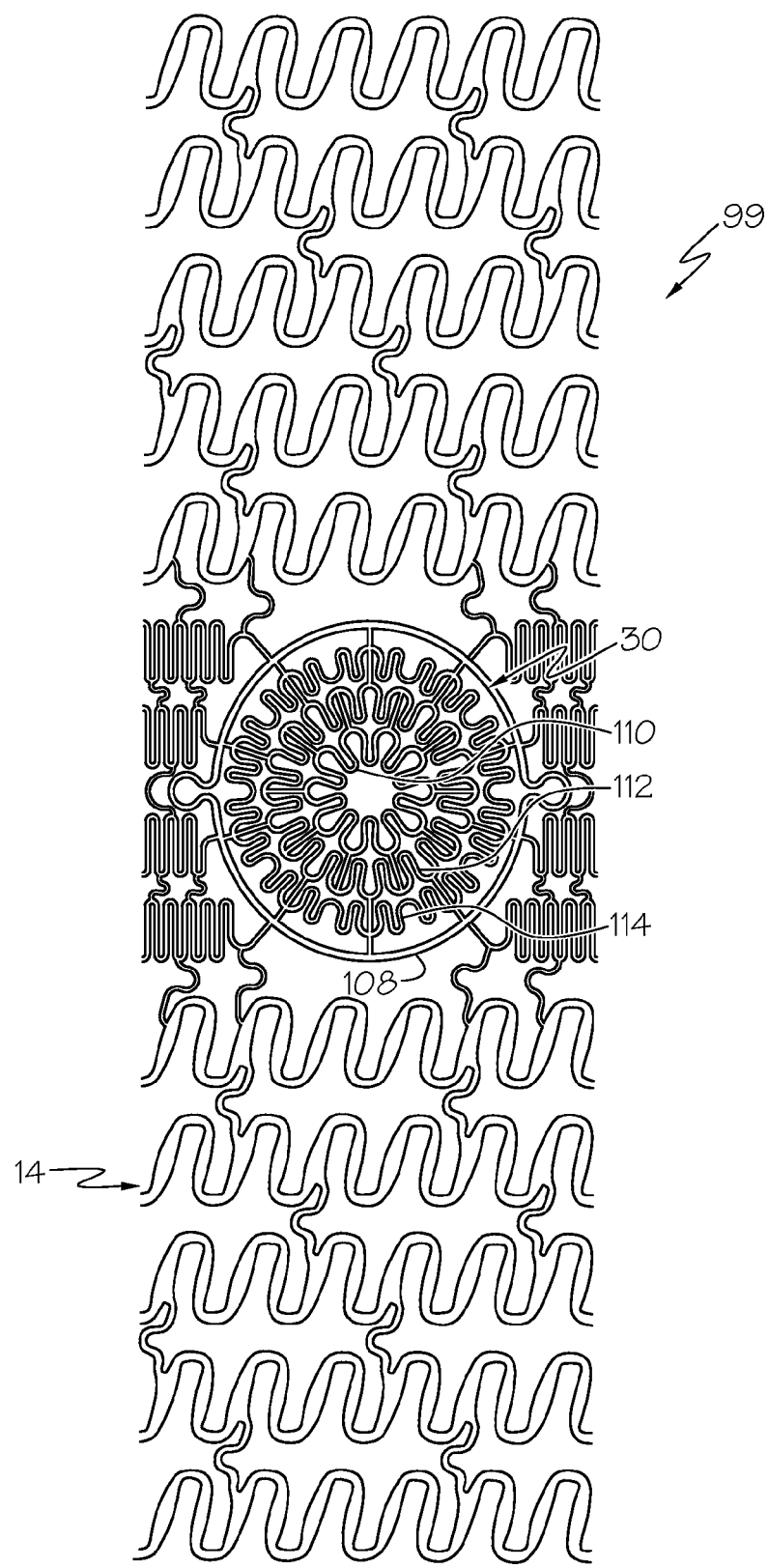
FIG. 23 is a flat view of another embodiment of an unexpanded stent in accordance with the present invention.
Figure 24:
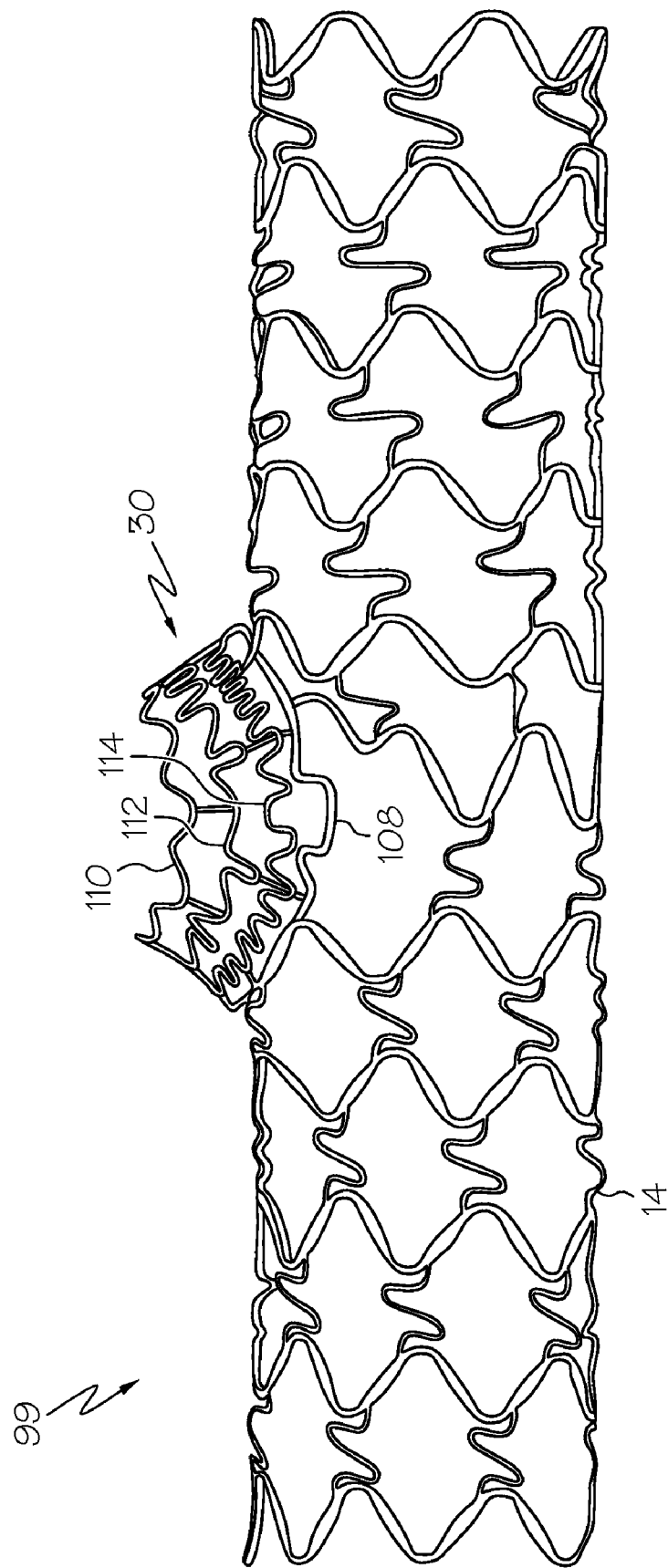
FIG. 24 is a view of an expandable branch portion of the stent of FIG. 23 in the expanded condition.

Referring to FIGS. 23 and 24, another embodiment of a stent 99 is shown in the unexpanded and expanded states, respectively. Stent 99 comprises a main stent body 14 and another embodiment of a branch portion 30. Stent 99 is substantially similar to stent 79, except stent 99 has a branch portion 30 including a support member 108 surrounding three concentric rings 110, 112, 114 instead of two. As can be seen in FIG. 24, when stent 99 is expanded the three concentric ring structure of this embodiment facilitates additional branch wall support because a generally more dense pattern is created in branch portion 30 with the addition of another concentric ring.

Figure 34:
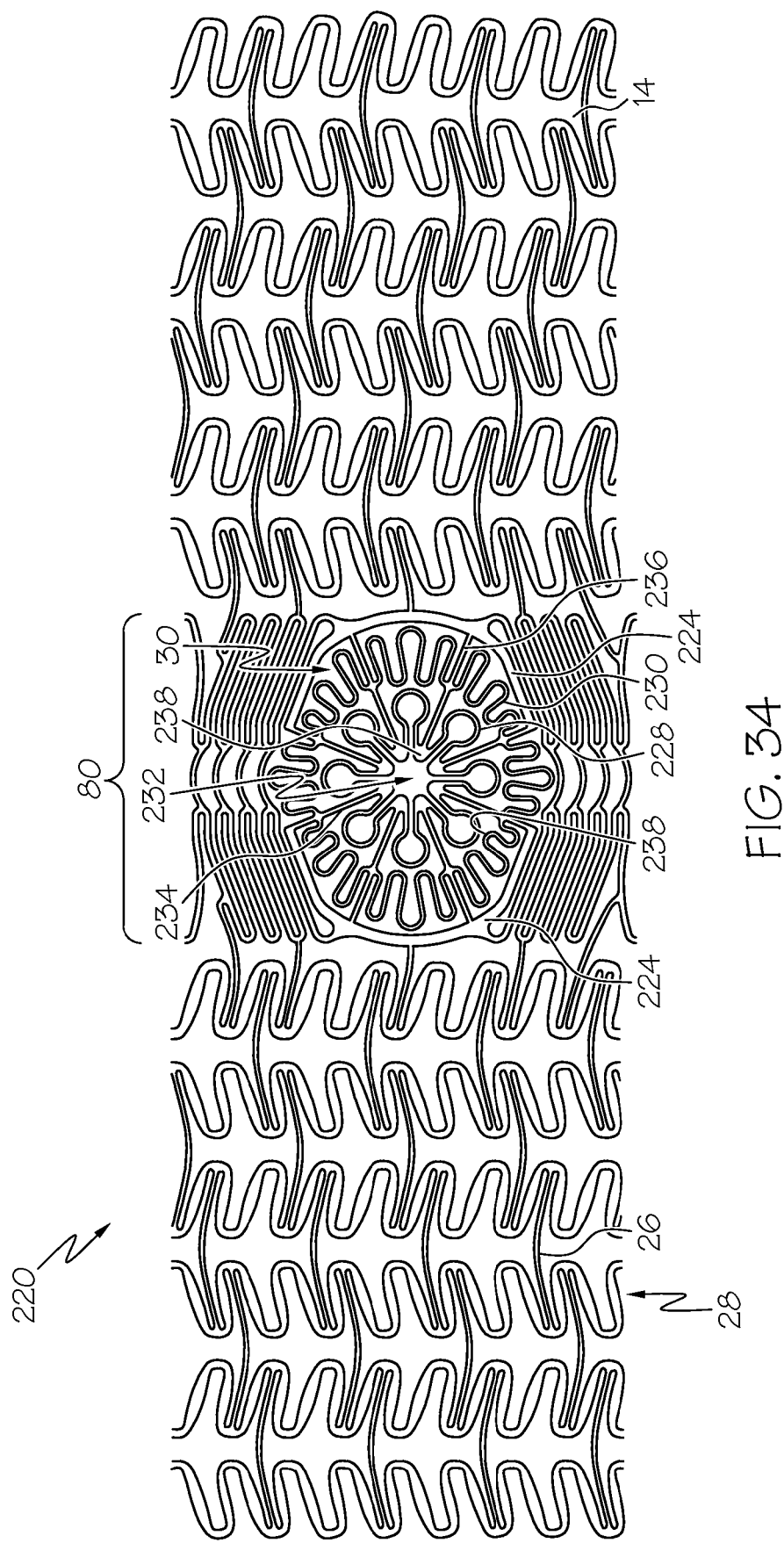
FIG. 34 is a flat view of another embodiment of an unexpanded stent in accordance with the present invention.

Referring to FIG. 34, an alternate embodiment of a stent 220 is shown having a main stent body 14 and another embodiment of branch portion 30. FIG. 34 is a flat view of stent 220 shown in an unexpanded condition where branch 30 has not been deployed. Main stent body 14 includes a main stent pattern having a generally repeatable ring 28 and connector 26 pattern. Branch portion 30 and the surrounding midsection 80 interrupt the repeatable ring 28 and connector pattern of stent 220. Branch portion 30 is configured to be extendable into the branch vessel such that the branch portion 30 contacts the entire periphery or circumference of the inner wall of the branch vessel in the expanded configuration.

In a preferred embodiment, transition members 224 may be provided as a transition between the main stent body 14 and branch portion 30. Transition members 224 comprise generally elliptical half portions positioned in an opposing relation with a space 246 therebetween. Transition members 224 surround a two concentric ring 228, 230 structure and a central branch opening 232. Branch opening 232 provides access to the side branch vessel when stent 220 is in the unexpanded condition and a side sheath may pass through opening 232. Rings 228 and 230 are interconnected by a plurality of inner connectors 234. Outer ring 230 is connected to transition members 224 by a plurality of outer connectors 236. Rings 228, 230 are generally curvilinear members and include undulation petals, prongs, or peaks 238. In this embodiment outer ring 230 includes a greater number of peaks than inner ring 228. Preferably eight outer connectors and eight inner connectors interconnect transition members 224 and rings 228, 230. In this embodiment, inner and outer connectors 234, 236 are generally straight members and are preferably aligned radially to extend toward the center of branch portion 30. In operation, the intersection of outer connectors 236 with transition members 224 form a pivot point about which petals 238 may unfold or pivot outward into the side branch vessel. In a preferred embodiment, the generally straight inner and outer connectors pivot together such that the petals 238 open like a flower.

Figure 35:
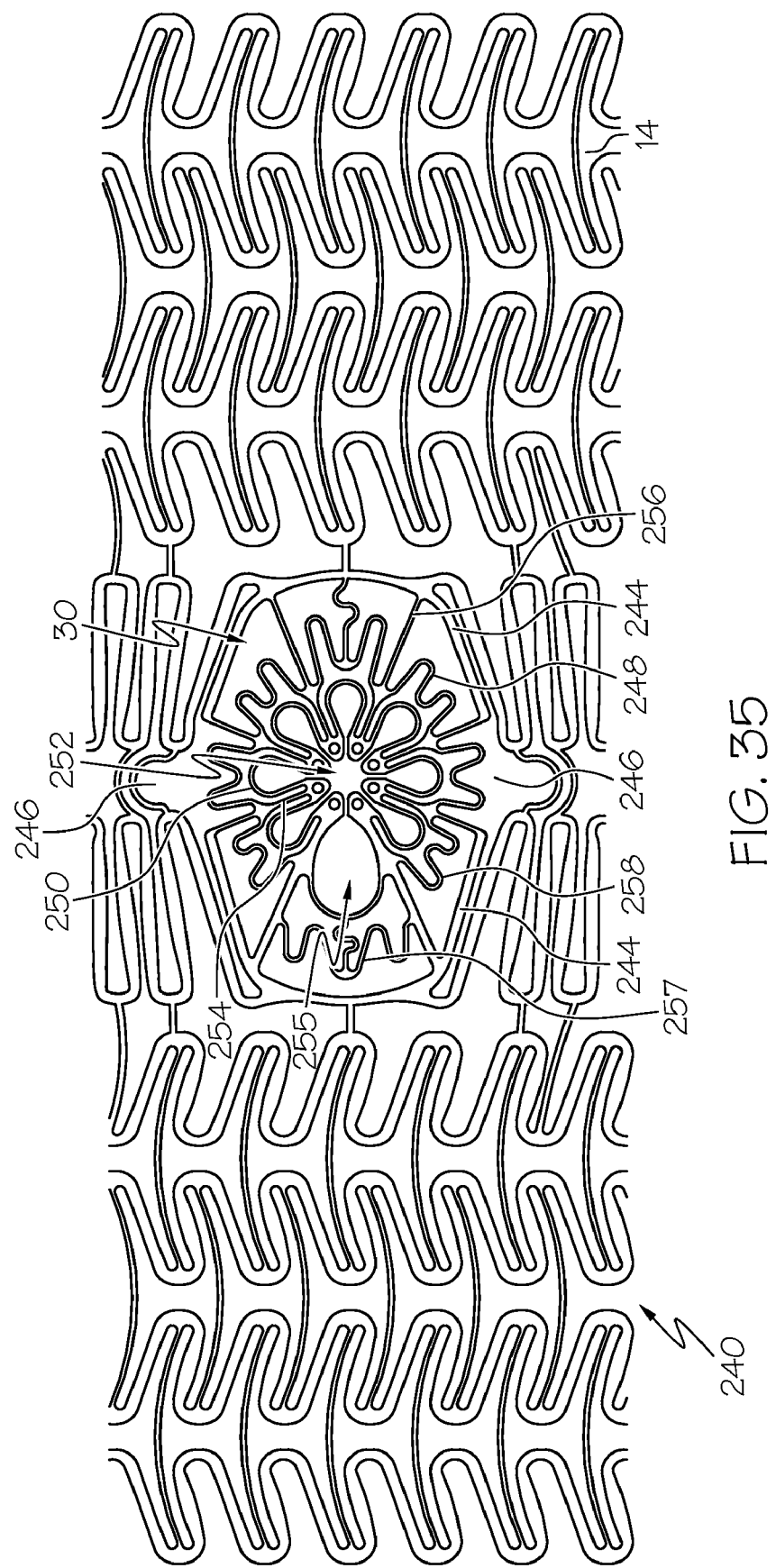
FIG. 35 is a flat view of another embodiment of an unexpanded stent in accordance with the present invention.
Figure 36:
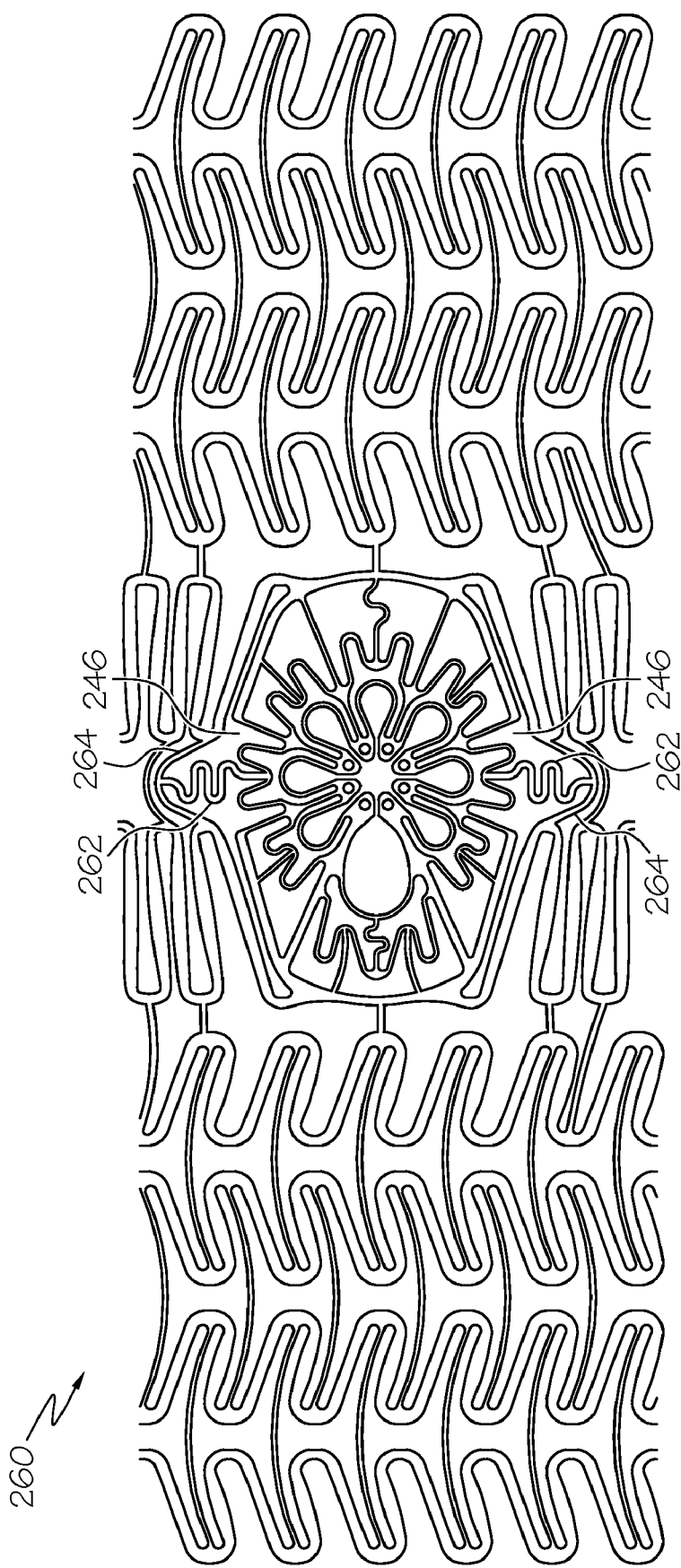
FIG. 36 is a flat view of another embodiment of an unexpanded stent in accordance with the present invention.

Referring to FIG. 35, an alternative embodiment of a stent 240 is shown having an alternate embodiment of a branch portion 30. Stent 240 includes structural support members 244 as a transition between the main stent body 14 and branch portion 30. Support members 244 comprise generally elliptical half portions positioned in an opposing relation with a space 246 therebetween. Support members 244 surround a two concentric ring 248, 250 structure and a central branch opening 252. Rings 248 and 250 are interconnected by a plurality of inner connectors 254. Outer ring 248 is connected to structural support members 244 by a plurality of outer connectors 256. Rings 248, 250 are generally curvilinear members and include undulation petals, prongs, or peaks 258. An auxiliary access opening 255 interrupts rings 248, 250 and provides access to the side branch vessel when stent 240 is in the unexpanded condition. A ring portion 257 extends between outer connectors 256 proximal to auxiliary access opening 255. In this embodiment, auxiliary access opening 255 is generally larger than central branch opening 252 to more readily receive a side sheath therethrough and to allow for greater access to the side branch. Auxiliary access opening 255 is preferably positioned proximal to central branch opening 252 when loaded on a stent delivery system, however auxiliary access opening 255 can have varying positions in alternate embodiments An alternate embodiment of a stent 260 is shown in FIG. 36 that is similar to stent 240 and it additionally includes lateral connecting members 262 that extend through space 246 and connect the outer ring 248 to struts 264 laterally outside branch portion 30. In this regard, when branch portion 30 is extended into the side branch, struts 264 are pulled radially inward to support the circumference of the ostium. This additional structure improves radial strength and provides additional support to the vessel wall.

Figure 37:
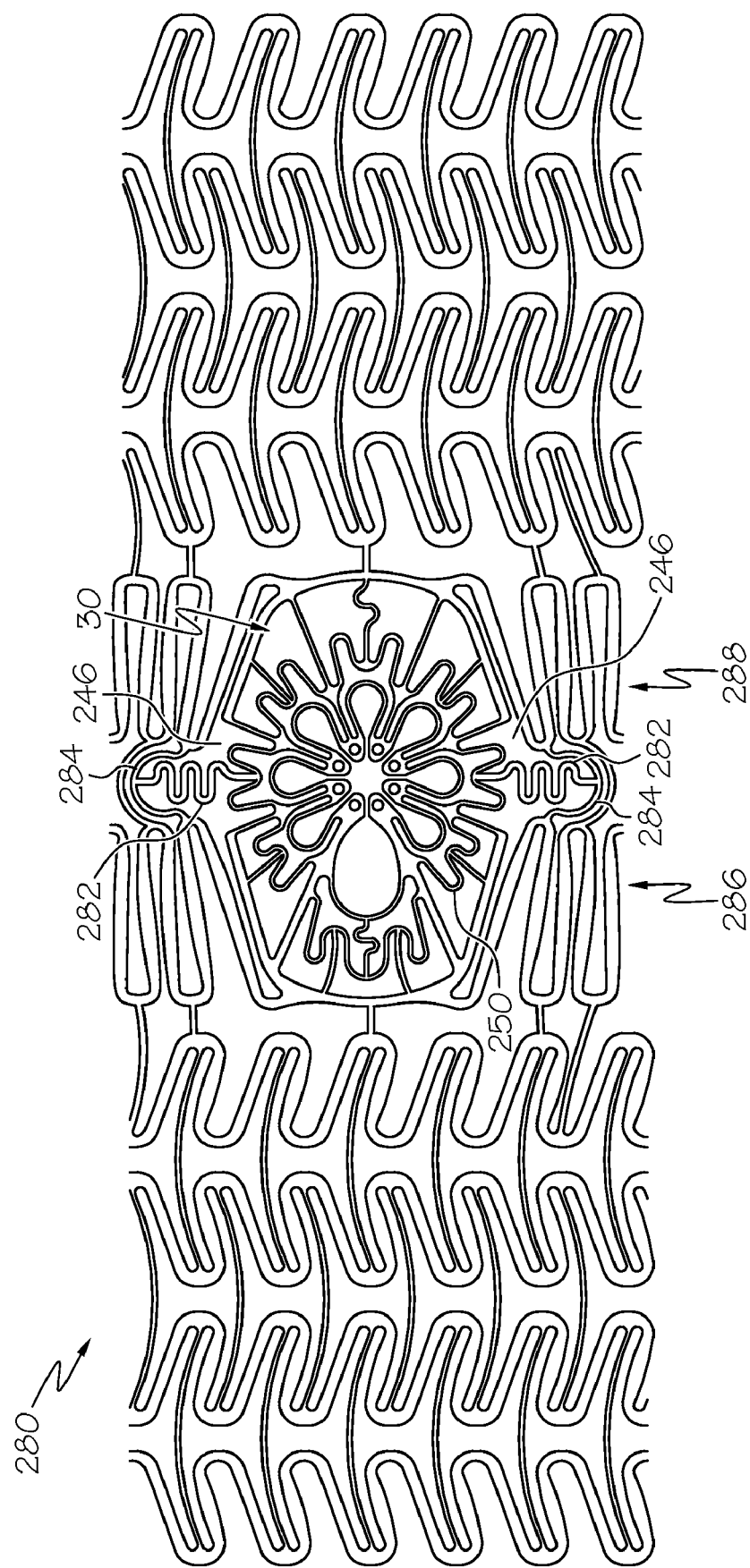
FIG. 37 is a flat view of another embodiment of an unexpanded stent in accordance with the present invention.

Referring to FIG. 37, an alternate embodiment of a stent 280 is shown that is similar to stent 260 and includes lateral connecting members 282 that extend through space 246 and connect the outer ring 248 to struts 284 laterally outside branch portion 30. Struts 284 are generally longitudinal connecting members spanning longitudinally between adjacent strut rings 286, 288. In this embodiment, struts 284 are generally curved members having a general omega shape. Struts 284 have a smaller radius of curvature than struts 264 of stent 240 described above. When branch portion 30 is extended into the side branch, struts 284 are pulled radially inward to support the circumference of the ostium. In addition, the general omega shape and comparatively smaller radius of curvature allow for greater expansion of struts 284 and permits greater movement or expansion of branch portion 30 without affecting deformation of the surrounding midsection 80. In alternate embodiments, other geometries of struts 284 may be used to accomplish the same purpose.

Figure 38:
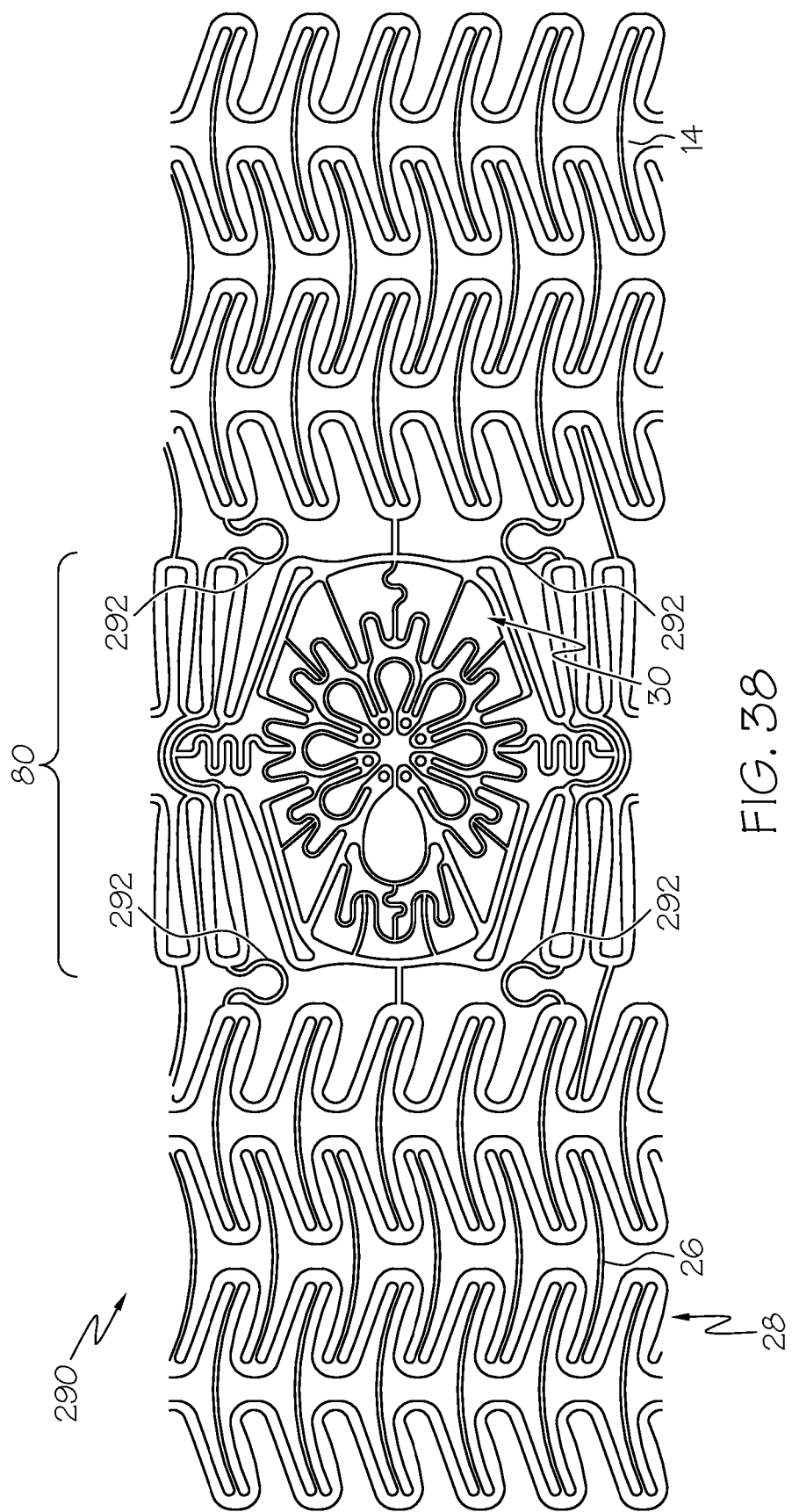
FIG. 38 is a flat view of another embodiment of an unexpanded stent in accordance with the present invention.
Figure 39:
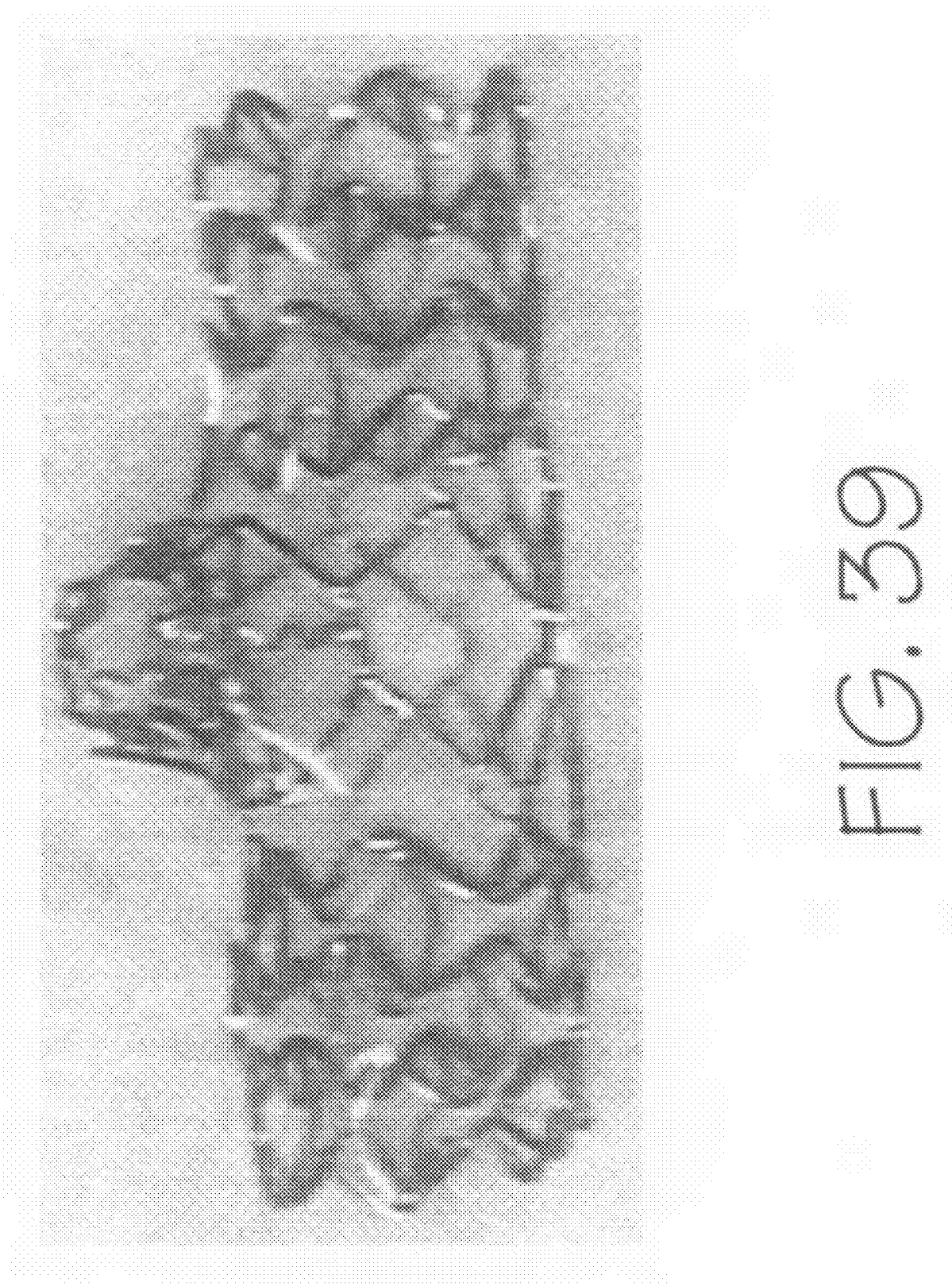
FIG. 39 is a perspective view of the stent of FIG. 38 in the expanded configuration.

Referring to FIGS. 38 and 39, an alternate embodiment of a stent 290 is shown that is similar to stent 280, described above, and generally includes at least one omega shaped connecting member 292 extending longitudinally outside branch portion 30 and connecting the midsection 80 to the repeatable ring 28 and connector 26 pattern of main stent body 14. As with prior embodiments, branch portion 30 is configured to be extendable into the branch vessel such that the branch portion 30 contacts the entire periphery or circumference of the inner wall of the branch vessel in the expanded configuration. Also, because midsection 80 has a different pattern than the main stent body, midsection 80 may expand radially to a different extent than the main stent pattern when branch portion 30 is extended into the side branch vessel. Connecting members 292 are configured to expand or contract accordingly to accommodate differential expansion of midsection 80 with respect to the main stent body. In this regard, connecting members 292 provide a cushion, dampening member, or act as a buffer between the expansion of the main stent body 14 and midsection 80 so that the expansion of main stent body 14 has a limited effect on the midsection 80 in operation and vice versa. In particular, the generally omega shape of connecting members 292 allow for greater expansion of connecting members 292 as compared to straight or substantially straight connector geometries. In alternate embodiments, other geometries of connecting members 292 may be used to accomplish the same purpose, that is to provide a cushion, dampen, or buffer the expansion of the midsection 80 with respect to the main stent body 14.

Figure 40:
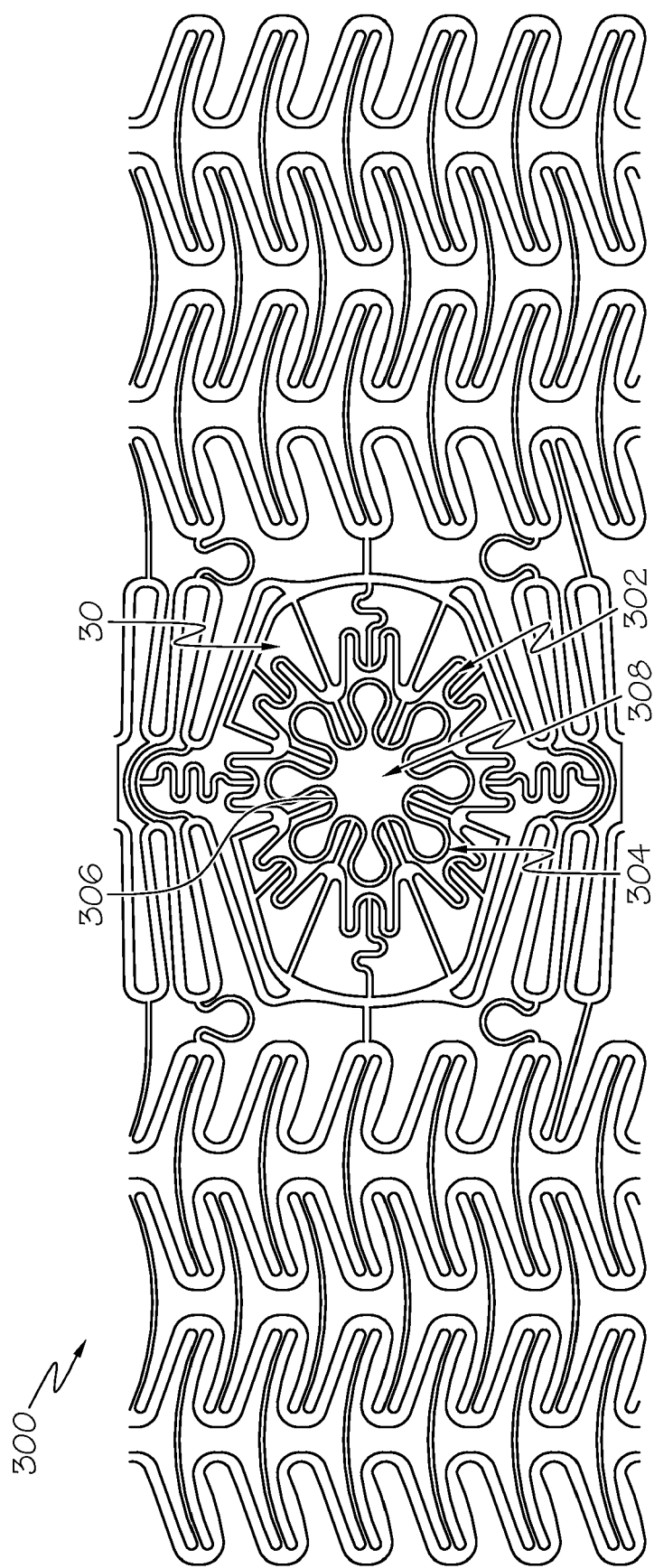
FIG. 40 is a flat view of another embodiment of an unexpanded stent in accordance with the present invention.
Figure 41:
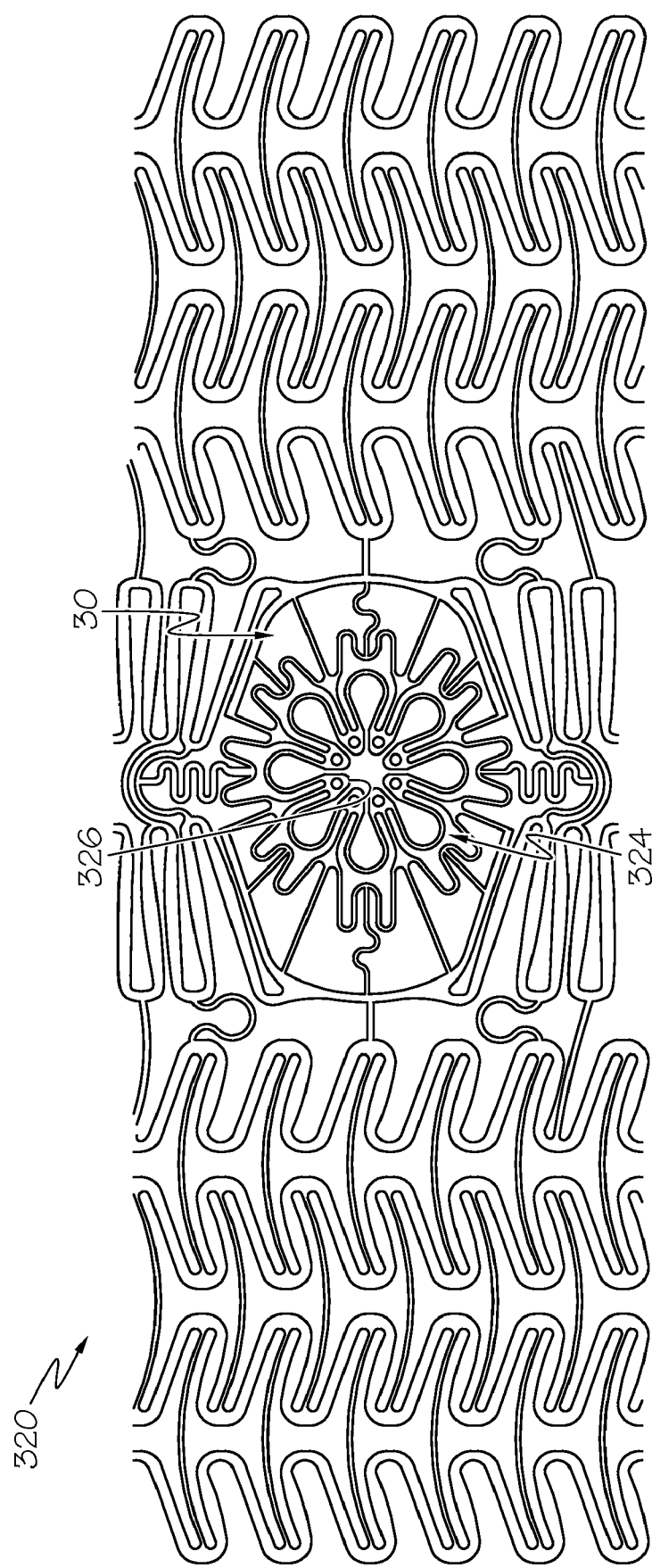
FIG. 41 is a flat view of another embodiment of an unexpanded stent in accordance with the present invention.
Figure 42:
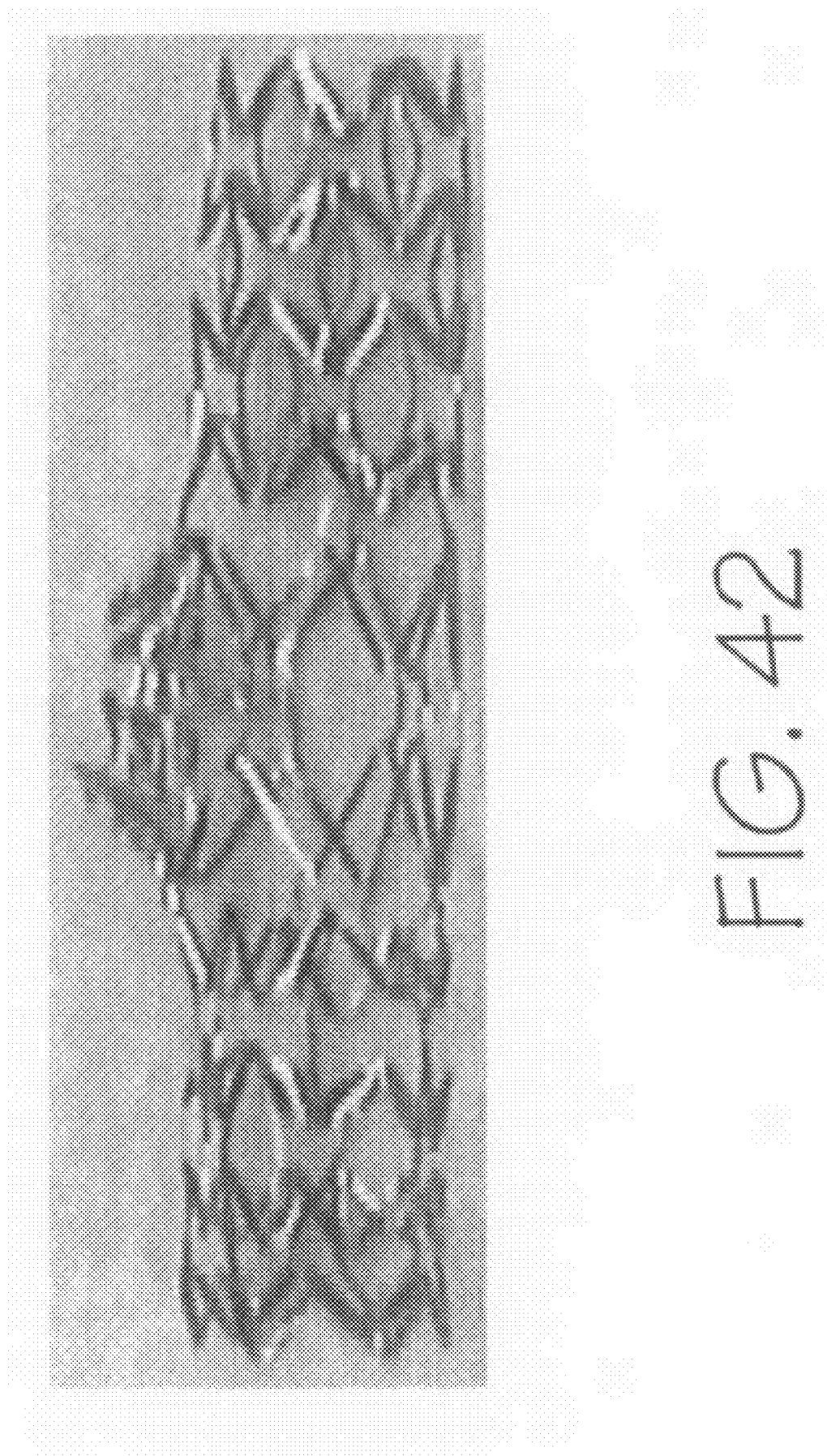
FIG. 42 is a perspective view of the stent of FIG. 41 in the expanded configuration.

Referring to FIG. 40, an alternate embodiment of a stent 300 is shown that is similar to stent 290, described above, and generally includes a branch portion 30 including an outer ring 302, and an inner ring 304. The inner ring defines undulation petals, prongs, or peaks 306 surrounding a central branch opening 308. Branch opening 308 provides access to the side branch vessel when stent 300 is in the unexpanded condition. In this embodiment, undulation peaks 306 of inner ring 304 have a relatively larger radius of curvature, i.e. they are less pointed, than, for example, the corresponding peaks 238 of inner ring 228 of stent 220, described above. For example, in a preferred embodiment peaks 306 may have a radius of curvature in the range of about 0.125 mm to about 0.225 mm, and preferably about 0.170 mm. In comparison, in a preferred embodiment peaks 238 of stent 220 may generally have a radius of curvature between about 0.025 mm to about 0.125 mm. In this regard, the geometry of peaks 306 may permit and/or facilitate the use of particular balloon types and designs. In particular, the design and shape of peaks 306 in this embodiment are less likely to pinch or puncture certain balloon designs. Although, in this embodiment branch portion 30 does not include an auxiliary access opening 255 to provide access to the side branch vessel, as with stents 240, 260, 280, and 290, in alternative embodiments, branch portion 30 may include such an auxiliary access opening. Referring to FIGS. 41 and 42, an alternative embodiment of a stent 320 is shown that is similar to stent 300, described above, except the inner ring 324 has undulation peaks 326 with a smaller radius of curvature than peaks 308 described above. Also, in this embodiment each peak 326 defines a hole configured and dimensioned to accommodate, for example, a marker.

Figure 43:
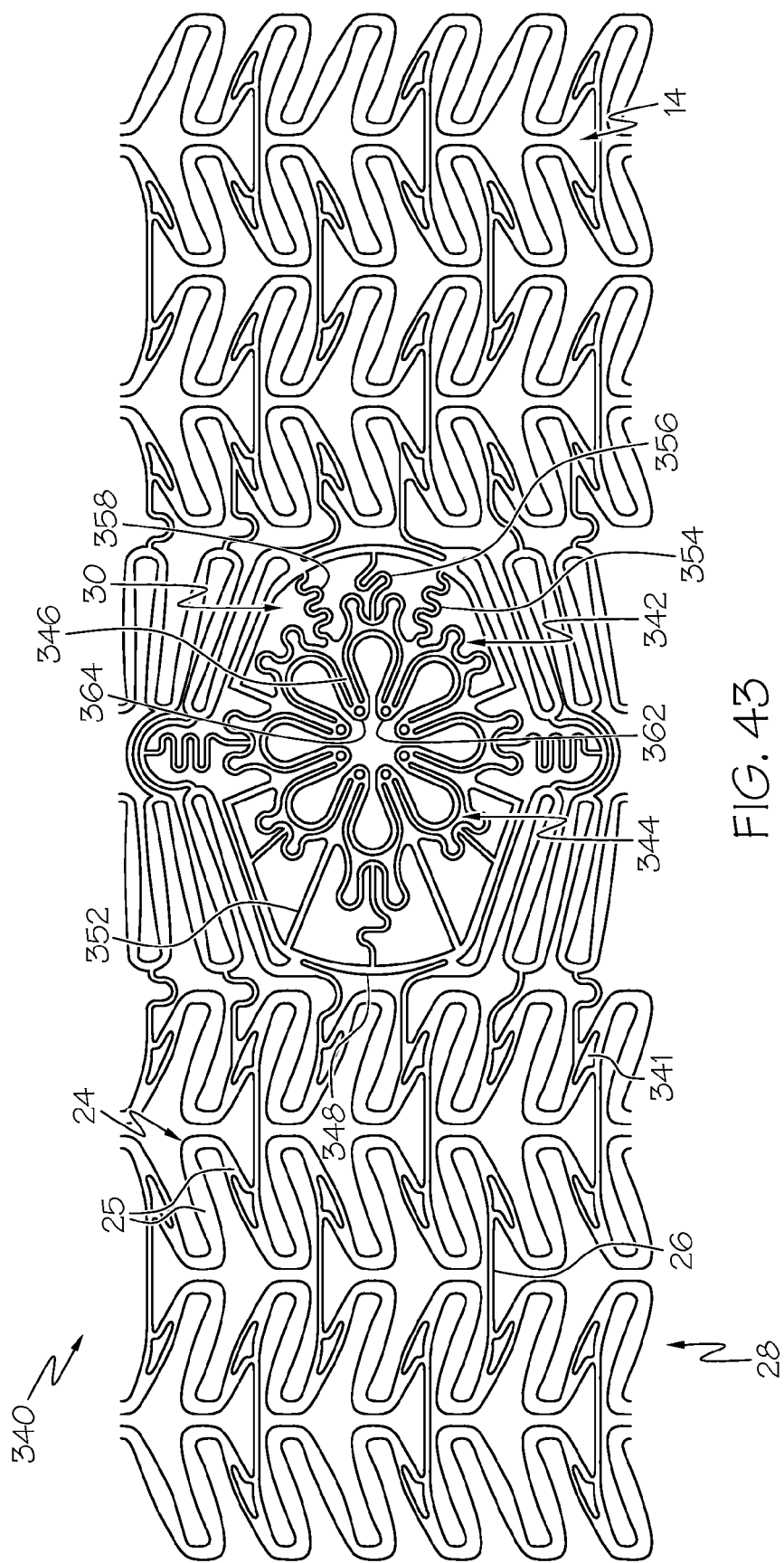
FIG. 43 is a flat view of another embodiment of an unexpanded stent in accordance with the present invention.
Figure 44:
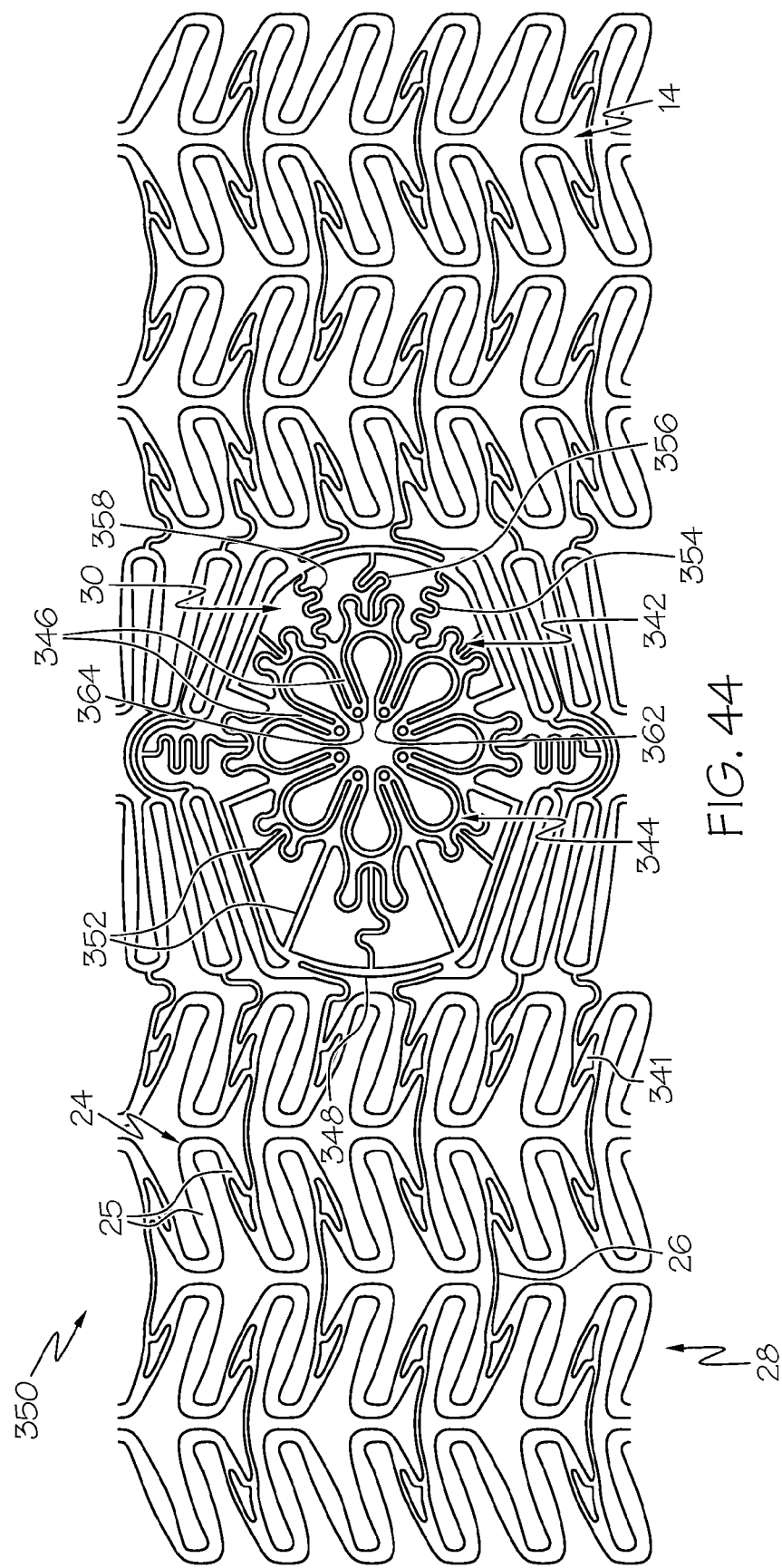
FIG. 44 is a flat view of another embodiment of an unexpanded stent in accordance with the present invention.
Figure 45:
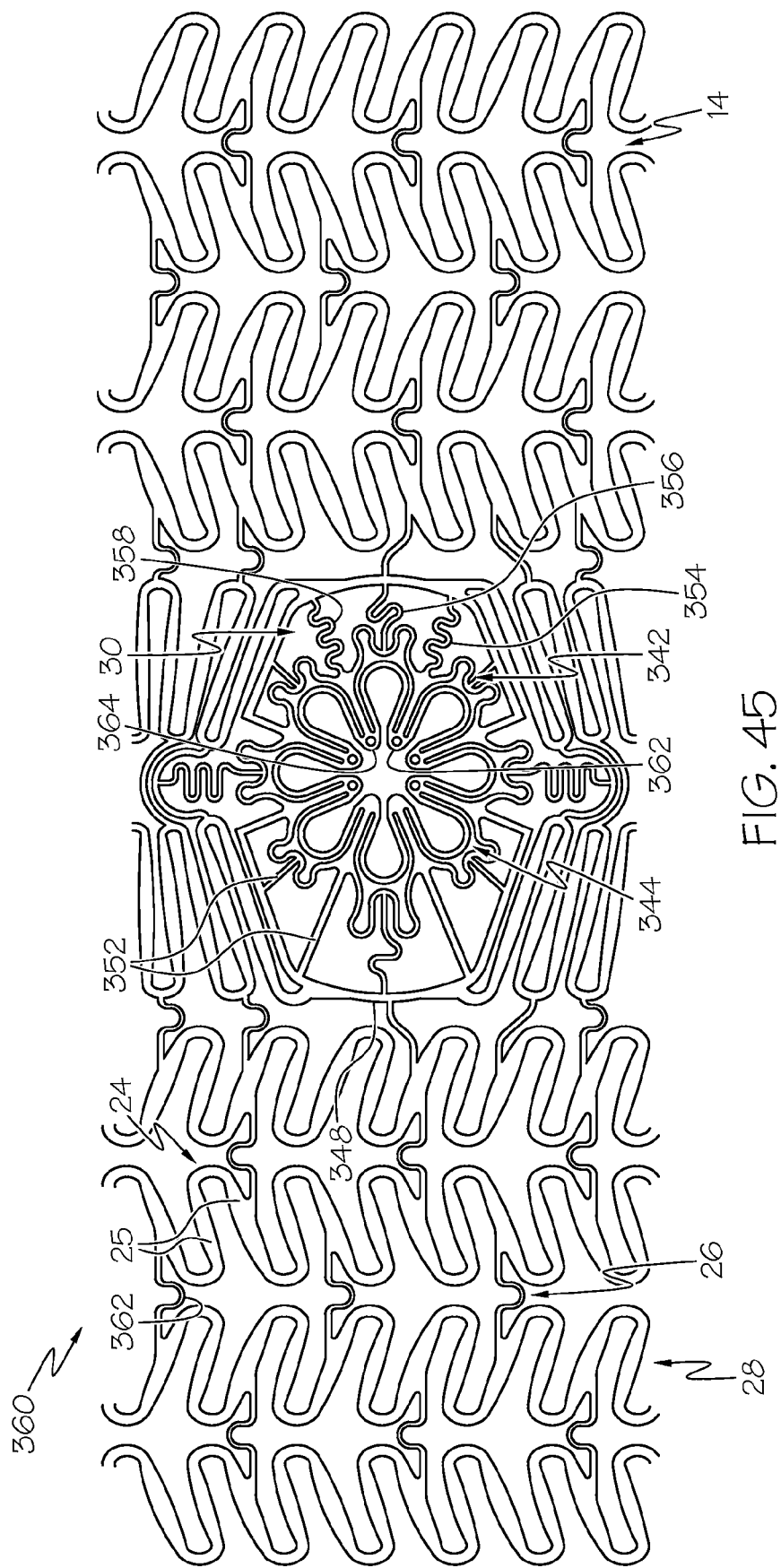
FIG. 45 is a flat view of another embodiment of an unexpanded stent in accordance with the present invention.

Referring to FIGS. 43-45, alternate embodiments of stents are shown having a main stent body 14 with alternative main stent pattern designs. In the embodiments of FIGS. 43-45, the main stent patterns have an open cell structure. For example, stents 340, 350, 360, each have a main stent body 14 having a generally repeatable ring 28 and connector 26 pattern and the connectors 26 are spaced apart and alternate every two or three strut pairs defining a more open cell structure as compared to providing connectors spaced apart or alternating every strut pair. In this regard, stents 340, 350, 360, have less stent material making up the main stent body and can have desirable clinical effects in certain applications. For example, if the stent is made from a metal material, it can be beneficial to have a smaller metal surface area ratio when the stent is installed in a patient. Referring now to FIGS. 43-45, stents 340, 350, 360 each have connectors 26 extending generally longitudinally between adjacent circumferential rings 28 and connecting to respective longitudinal strut portions 25 of longitudinally adjacent struts 24 of adjacent rings 28. Connectors 26 are spaced apart and alternately connect every other pair of longitudinally adjacent struts connectors 26 are spaced apart and alternate every two or three strut pairs defining a more open cell structure. As shown in FIG. 43, one embodiment of a stent 340 may have connectors 26 that are substantially straight and may extend between the midsections of the longitudinal strut portions 25 of longitudinally adjacent struts 24. Also, the midsection of longitudinal strut portions 25 may include a hole, space, or void 341, thus further reducing the amount of material used. In some embodiments, void 341 may be provided adjacent the junction of connector 26 with longitudinal strut portion 25 and in alternate embodiments (e.g. FIG. 46) a void 341 may be provided at the midsection of every longitudinal strut portion. In this regard, the hole, space, or void permits the design of stent patterns utilizing even less material to, for example, further decrease the metal to surface area ratio. As shown in FIG. 44, an alternate embodiment of a stent 350 is shown having connectors 26 that are generally arcuate and extend between the midsections of the longitudinal strut portions 25 of longitudinally adjacent struts 24. Referring to FIG. 45, another embodiment of a stent 360 is shown having connectors 26 that include an omega shaped feature 362 which permits expansion of connectors 26 in the longitudinal direction. In alternate embodiments, other geometries of connectors 26 may be used to accomplish the same purpose.

Stents 340, 350, 360, shown in FIGS. 43-45, generally include a branch portion 30 similar to stent 320 (FIG. 41) including an outer ring 342, and an inner ring 344. Rings 342 and 344 are interconnected by a plurality of inner connectors 346. Outer ring 342 is connected to elliptical transition members 348 by a plurality of outer connectors 352. In these embodiments, outer connectors 352 include a subset of distal outer connectors 354, 356, 358 that extend from the distal side of outer ring 342 to the elliptical transition member on the distal side of branch portion 30. Distal outer connectors 354, 356, 358 are generally S-shaped, zigzag-shaped, or wavelike. In this regard, the wavelike shape of distal outer connectors may be deformed to a greater extent and accommodate more expansion than, for example, a straight outer connector design. In these embodiments, distal outer connectors 354, 356, 358 may generally accommodate large angles of rotation of the distal portion of branch portion 30 into the side branch vessel during implantation. For example, the distal petals 362, 364 may rotate more than 90.degree. during implantation in the side branch vessel.

Figure 46:
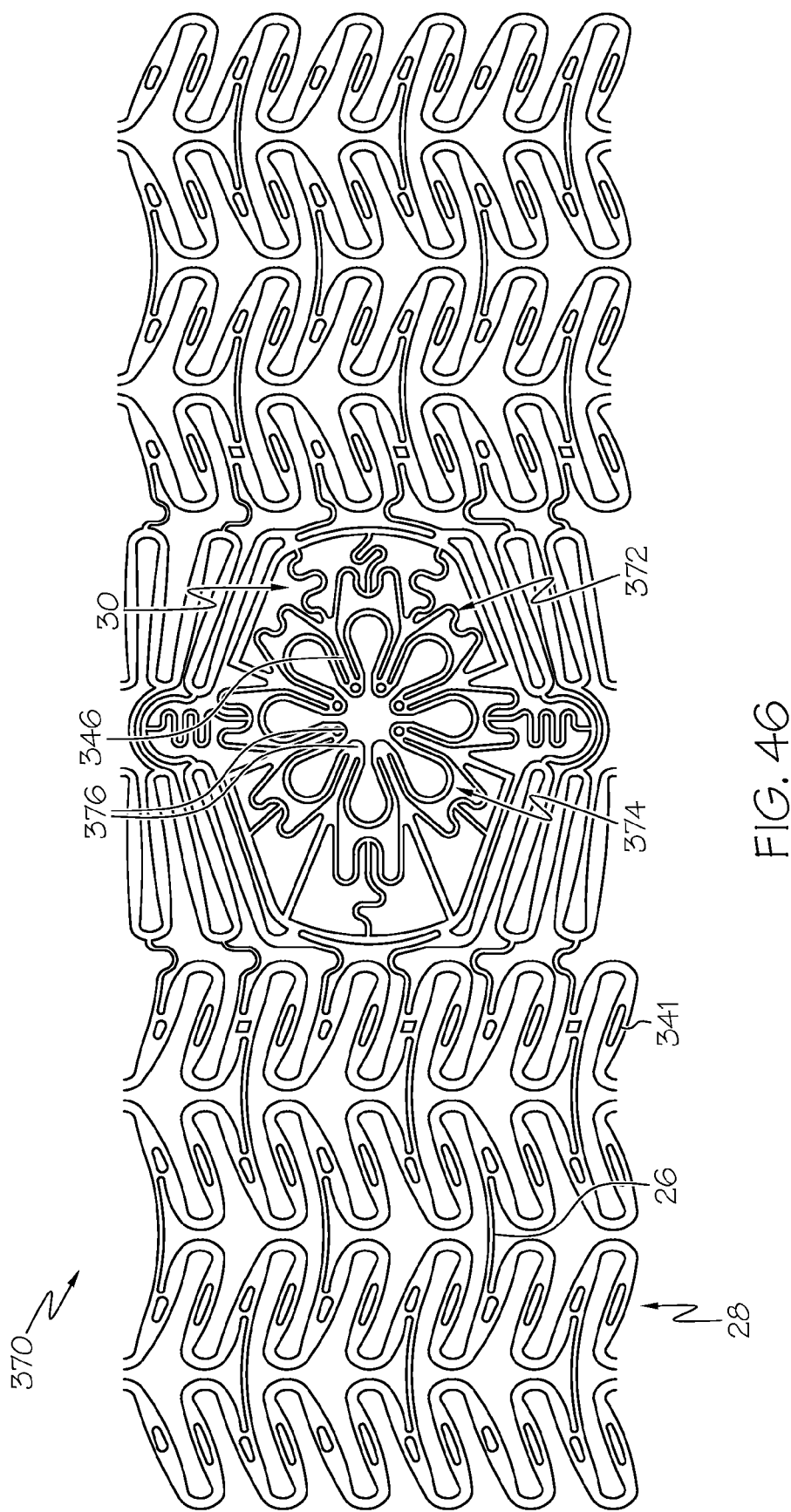
FIG. 46 is a flat view of another embodiment of an unexpanded stent in accordance with the present invention.
Figure 47:
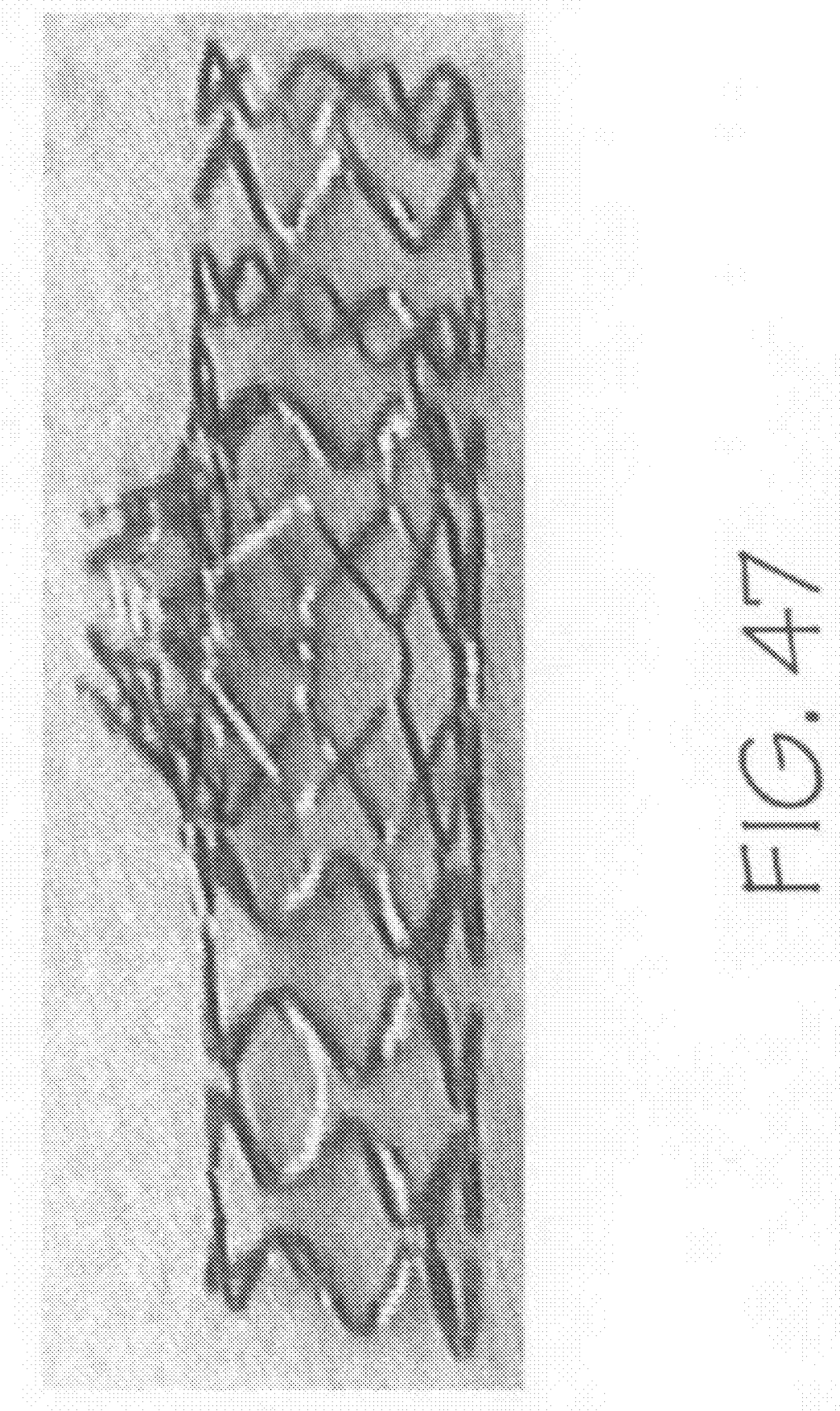
FIG. 47 is a perspective view of the stent of FIG. 46 in the expanded configuration.

Referring to FIGS. 46 and 47, an alternate embodiment of a stent 370 is shown that is similar to stent 360, described above, and generally includes a branch portion 30 including an outer ring 372, and an inner ring 374. Rings 372, 374 are generally curvilinear members and include undulation petals, prongs, or peaks 376. In this embodiment outer ring 372 is generally less curvilinear than outer ring 342 of stents 340, 350, 360 described above. For example as shown in FIG. 46, outer ring 372 can be viewed as a series of interconnected connected W-shaped sections, wherein the legs of the W-shaped sections are straighter than the comparable sections of outer ring 342 described above. In this regard, the geometry of outer ring 372 may permit and/or facilitate different type of expansion characteristics of the branch portion 30 upon installation into a side branch vessel. In alternate embodiments, other geometries of outer ring 372 may be used.

Figure 48:
FIG. 48 is a flat view of another embodiment of an unexpanded stent in accordance with the present invention.

Referring to FIG. 48, an alternate embodiment of a stent 380 is shown that is similar to stent 370, described above, and generally includes a branch portion 30 including an outer ring 382, and an inner ring 384. Rings 382 and 384 are interconnected by a plurality of inner connectors 388. Outer ring 382 is connected to elliptical transition members 390 by a plurality of outer connectors 392. Rings 382, 384 are generally curvilinear members and include undulation petals, prongs, or peaks 394. In this embodiment outer ring 382 generally includes the same number of peaks as inner ring 384. For example, inner ring 384 generally includes eight major petals or peaks 396 extending toward and surrounding a central branch opening 397 and eight minor peaks 398 extending and alternating between major peaks 396. Minor peaks 398 extend to a lesser extent toward central branch opening 397. In operation, the intersection of outer connectors 392 with transition members 390 form a pivot point about which major petals 396 may unfold or pivot outward into the side branch vessel. In a preferred embodiment, the inner and outer connectors pivot together such that the major petals 396 open like a flower. Also, the minor peaks 398 of inner ring 384 may undergo deformation and expand when major petals pivot outward into the side branch vessel. In this regard, the geometry of inner ring 384 may permit and/or facilitate different type of expansion characteristics of the branch portion 30 and may also provide for varying degrees of coverage or radial support of the side branch vessel wall upon installation into a side branch vessel. In alternate embodiments, other geometries of inner ring 384 may be used.

In all of the above embodiments, the branch portion 30 protrudes into the branch vessel when the stent is fully expanded. The branch portion upon expansion can extend into the branch vessel in different lengths depending upon the application. The amount of extension may vary in a range between about 0.1-10.0 mm. In one preferred embodiment, the length of extension is 1-3 mm. In another preferred embodiment, the length of extension is approximately 2 mm. In alternative embodiments, the amount of extension into the branch vessel may be variable for different circumferential segments of branch portion 30. As shown in each of the embodiments, the branch portion is approximately 2.5 mm in width and about 2.5-3.0 mm in length. However, the branch portion can be dimensioned to accommodate varying size branch vessels. The branch portion can be formed of any tubular shape to accommodate the branch vessel, including, oval or circular, for example.

In general, a wide variety of delivery systems and deployment methods may be used with the aforementioned stent embodiments. For example, a catheter system may be used for insertion and the stent may be balloon expandable or self-expandable, or the stent may be balloon expandable and the branch portion self-expandable, or vice versa. Once the stent is in position in the main vessel and the branch portion is aligned with the side branch the stent can be expanded. If the stent is balloon expandable, the stent may be expanded with a single expansion or multiple expansions. In particular, the stent can be deployed on a stent delivery system having a balloon catheter and side sheath as described, for example, in U.S. Pat. Nos. 6,325,826 and 6,210,429, the entire contents of which are incorporated herein by reference. In one preferred embodiment, a kissing balloon technique may be used, whereby one balloon is configured to expand the stent and the other balloon is configured to extend branch portion 30. After the main portion of the stent is expanded in the main vessel, the stent delivery system may be removed and a second balloon may be passed through the side hole in the branch portion and expanded to expand the branch portion of the stent. In an alternate embodiment, the same balloon may be inserted in the main vessel inflated, deflated, retracted and inserted into the branch vessel, and then reinflated to expand branch portion 30 and cause it to protrude into the branch vessel. Alternatively, the stent can be delivered on two balloons and the main portion and the branch portion can be expanded simultaneously. As needed, the branch portion can be further expanded with another balloon or balloons. Yet another alternative is to use a specially shaped balloon that is capable of expanding the main and branch portions simultaneously. The stent can also be deployed with other types of stent delivery systems. Alternatively, the stent, or portions of the stent, can be made of a self-expanding material, and expansion may be accomplished by using self-expanding materials for the stent or at least branch portion 30 thereof, such as Nitinol, Cobalt Chromium, or by using other memory alloys as are well known in the prior art.

The construction and operation of catheters suitable for the purpose of the present invention are further described in U.S. patent application Ser. No. 09/663,111, filed Sep. 15, 2000, which is a continuation-in-part of U.S. patent application Ser. No. 09/614,472, filed Jul. 11, 2000, which is a continuation-in-part of U.S. patent application Ser. No. 09/325,996, filed Jun. 4, 1999, and Ser. No. 09/455,299, filed Dec. 6, 1999, the disclosures of all of which are incorporated herein by reference. It should be noted that the catheters taught in the above applications are exemplary, and that other catheters that are suitable with the stents of the subject application are included within the scope of the present application. In alternative embodiments, catheters without balloons may be used. For example, if the stent is comprised of memory alloy such as Nitinol or Cobalt Chromium, or is a mechanically self-expanding stent, balloons are not necessarily included on the catheters. Furthermore, any other catheter, including ones that are not disclosed herein, may be used to position stents according to the present invention.

Figure 25:
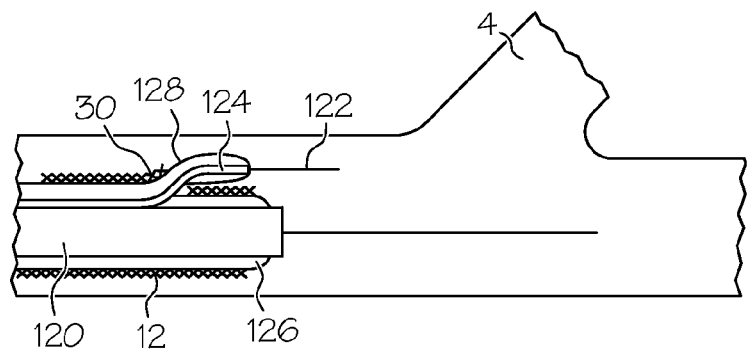
FIGS. 25-28 are illustrations of the steps for a method of inserting a stent of the present invention, according to one embodiment.
Figure 26:
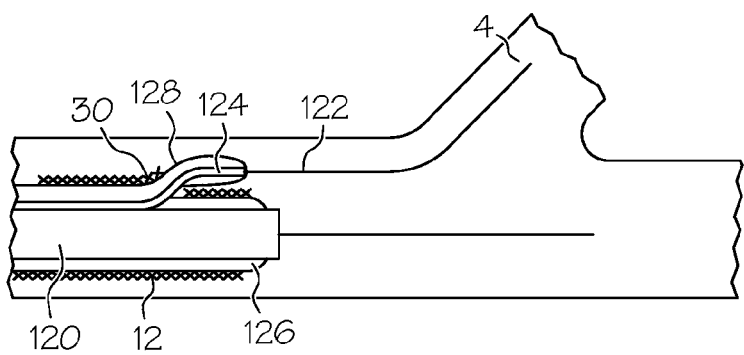
Figure 27:
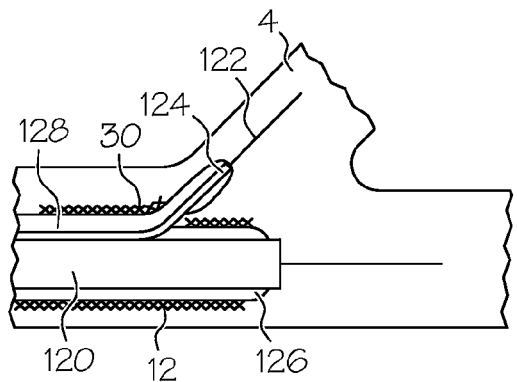
Figure 28:
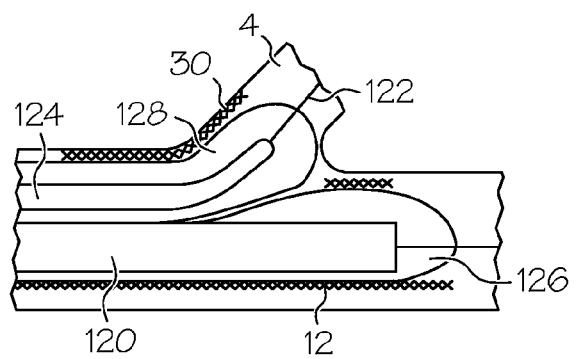

Referring now to FIGS. 25-28, illustrations of the steps of one example of a method for employing a stent according to the invention are shown. By way of example, the method is depicted utilizing stent 12. Methods for positioning such a catheter system within a vessel and positioning such a system at or near a bifurcation are described more fully in U.S. patent application Ser. No. 10/320,719 filed on Dec. 17, 2002, and published as US 2003/0181923 A1, which is incorporated herein by reference in its entirety. As shown in FIG. 25, a catheter system 120 is positioned proximal to a bifurcation, using any known method. A branch guidewire 122 is then advanced through an opening in the stent and into the branch vessel 4, as shown in FIG. 26. In a preferred embodiment, the opening may be a designated side branch opening, such as an opening formed by the absence of some connectors 26, as described above. Branch portion 30 is adjacent the opening. As shown in FIG. 27, if the side sheath 124 is attached to the main catheter 120, the main catheter 120 is advanced along with the side sheath 124. Alternatively, if the side sheath 124 is separate from to the main catheter 120, the second catheter or side sheath 124 is then advanced independently through the opening in the stent and into the branch vessel. Branch portion 30 is positioned over a portion of the lumen of the branch vessel 4 as the side sheath 124 is inserted into branch vessel 4. Referring to FIG. 28, a first balloon 126 located on main catheter 120 is then expanded, causing expansion of the stent body, and a second balloon 128 located on the second catheter or side sheath 124 is also expanded, causing branch portion 30 to be pushed outward with respect to the stent body, thus providing stent coverage of at least a portion of the branch vessel. The balloons are then deflated and the catheter system and guidewires are then removed.

Figure 29:
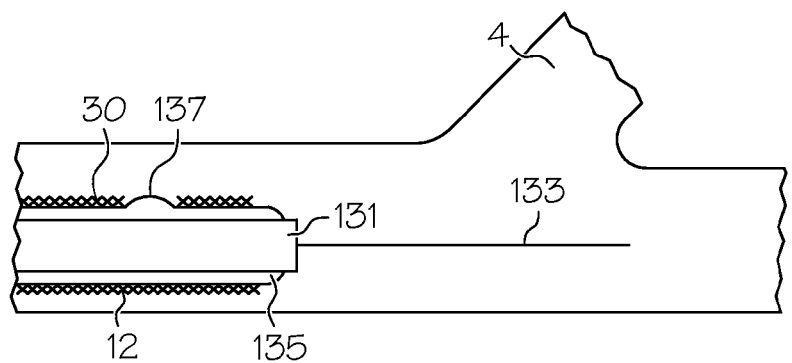
FIGS. 29-31 are illustrations of the steps for another method of inserting a stent of the present invention.
Figure 30:
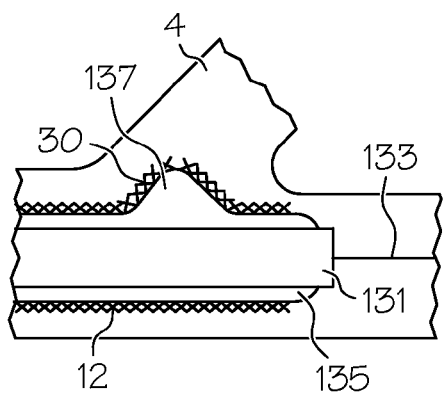
Figure 31:
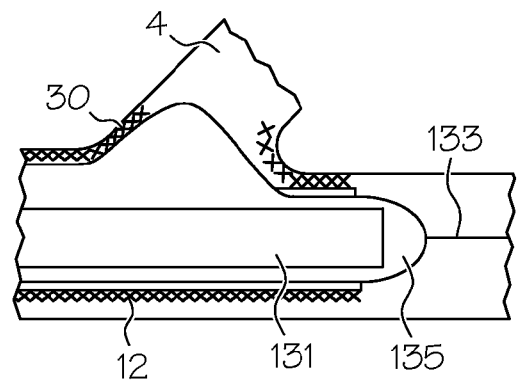
Figure 32:
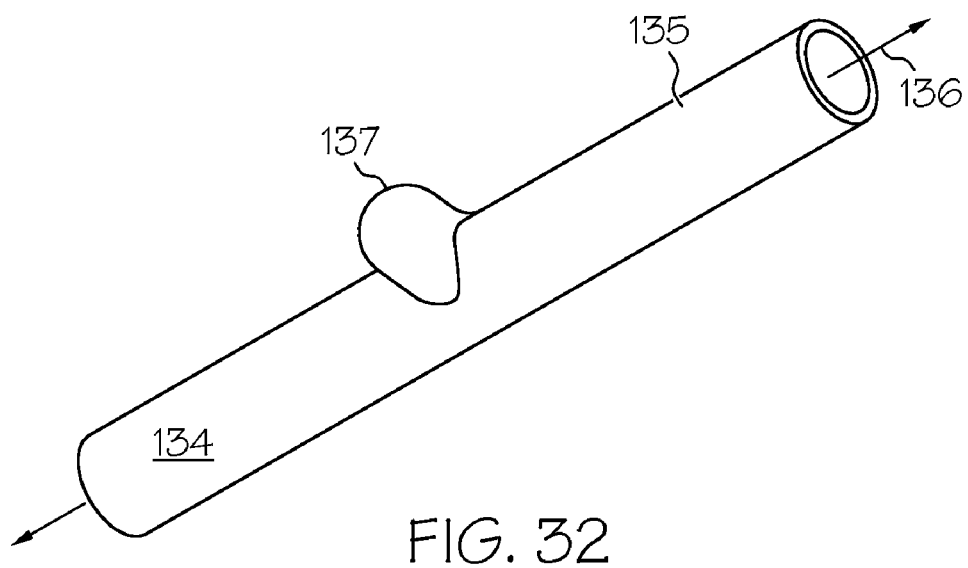
FIG. 32 is a view of a herniated balloon for use with the method of FIGS. 29-31.

Referring now to FIGS. 29-31, illustrations of the steps of another method for employing a stent of the present invention is shown. By way of example, the method is depicted utilizing stent 12. The depicted method may be accomplished using a catheter system having a main catheter 131 including a herniated balloon 135 (FIG. 32). In particular, the stent can be deployed on a stent delivery system having a herniated balloon as described, for example, in U.S. patent application Ser. No. 60/488,006, filed Jul. 18, 2003, the entire contents of which are incorporated herein by reference. As shown in FIG. 29, the catheter 131 includes a balloon 135 that has a protruding portion 137 that protrudes outwardly from the cylindrical outer surface 134 of the balloon.

Referring to FIG. 32, the herniated balloon 135, shown in an expanded state, has a generally cylindrical shape and the protruding portion 137 can be any appendage or integral portion of the balloon that moves outwardly from the outer surface 134 of the balloon upon inflation, in accordance with the principles of the invention. In a preferred embodiment, the protruding portion 137 is a portion of the balloon wall that has greater expandability than other portions of the balloon wall that retain a generally cylindrical shape. In another embodiment, protruding portion 137 may be a solid structure attached to the balloon wall. The protruding portion 137 can have any shape desirable to effect deployment of branch portion 30. In one preferred embodiment, protruding portion 137 has a hemispherical shape. In another preferred embodiment, protruding portion 137 has an ovoid shape. In use, the stent 12 is crimped onto the balloon 135 so that the protruding portion 137 is positioned at the branch portion. As shown, the protruding portion 137 is positioned adjacent or alongside the radially inward side of branch portion 30. The herniated balloon 135 is used to expand the branch portion 30 and/or deploy the outwardly deployable structure of stent 12 by applying a force in the laterally outward direction to the expandable elements by deflecting these elements toward the side branch 4. The protruding portion 137 may be located at any position along the length of the balloon. For example, it can be located on the middle ⅓ of the stent.

In one embodiment, the balloon may be constructed of composite materials. For example, a combination of elastomeric and semi to non compliant materials such as urethane, silicone, and latex, (Elastomeric) polyethylene hytrel pebax polyarylethertherketone, polyoxymethylene, polyamide, polyester thermoplastic polyetheretherketone and polypropylene (semi to non compliant), may be used. The balloon may also be constructed by combining the above-mentioned materials with woven textiles such as Kevlar, silk cotton, wool, etc. In this construction, a textile is wound or woven onto a rod that has the shape of the desired herniated balloon and the polymer is then extruded or dip coated over the rod. The composite is cured, heat set or adhesively fused together. The rod is then removed and the remaining shape is a herniated balloon. The balloon can also be constructed by adding an appendage to a conventional balloon by using a molded collar or adhesively attaching an object to the surface of the balloon or by using a mound of adhesive to create the herniation or protruding portion. In an alternate embodiment, the balloon can be constructed by molding three small balloons and attaching them in tandem with the center balloon being round in shape. The balloon would share a common inflation port. When the balloon is inflated the center balloon becomes the herniation.

Referring again to FIGS. 29-31, protruding portion 137 may be configured to fit directly into an opening in the stent. As shown in FIG. 29, catheter 131 is advanced over a guidewire 133 and positioned proximal to the bifurcation. As shown in FIG. 30, the catheter is advanced until the protruding portion 137 of the balloon is positioned at the bifurcation. In one embodiment, protruding portion 137 protrudes outwardly from catheter 131 enough so that it actually comes into contact with the bifurcation, thus providing a method of alignment with the branch vessel 4. Finally, as shown in FIG. 31, balloon 135 is expanded, which simultaneously causes the stent to expand and branch portion 30 to be pushed toward the branch vessel 4. Upon inflation of the balloon, the herniated portion 137 expands and extends through the branch portion 30 toward the side branch to open the entrance of the occluded side branch artery.

In an alternative method, the stent can be delivered using a herniated balloon and a dual lumen delivery system. This system can include a main catheter defining a first lumen with concentric guidewire lumen and balloon inflation lumen, a herniated balloon, as described above, on the main catheter, a side sheath with a guidewire lumen, and a stent. The stent is crimped over the main catheter, balloon and side sheath with the side sheath exiting the stent through a branch opening or side hole. The distal end of the side sheath is used for aligning the stent branch opening with the branch vessel 4.

Figure 33:
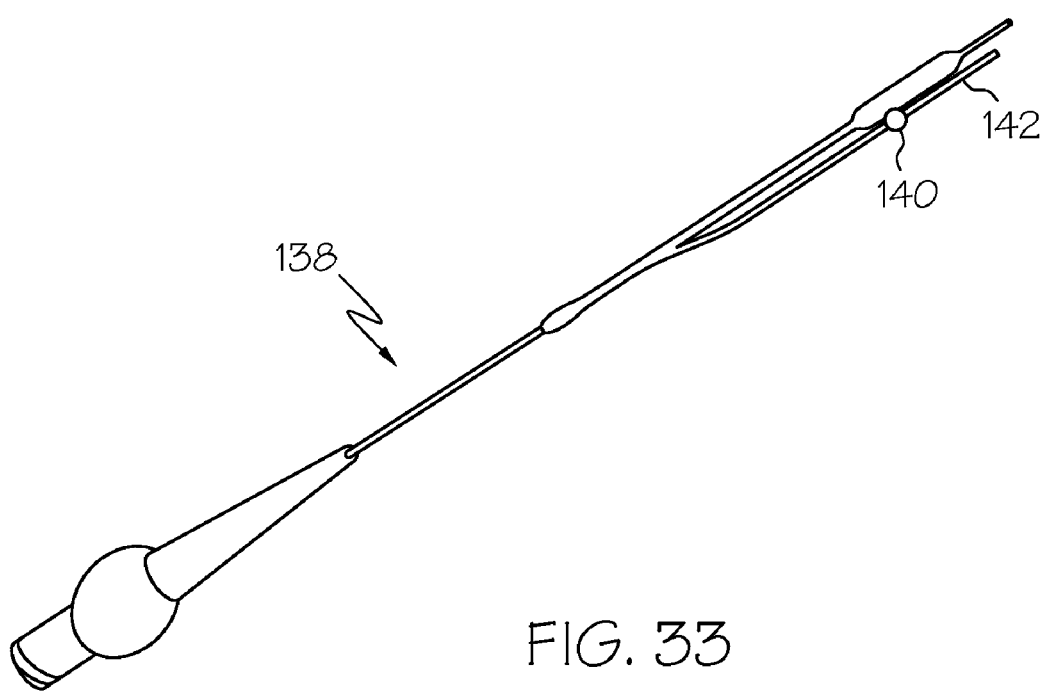
FIG. 33 is a view of another stent delivery system for inserting a stent in accordance with another method of the present invention.

In another embodiment, the appendage or herniation may be located on a second catheter or side sheath of the delivery system, such as the system 138 depicted in FIG. 33. In this case, the system is a two-balloon system. The smaller balloon 140 can be positioned in the stent in a similar manner as the herniation. The appendage or herniation may have an inflation lumen 141 and a lumen for receiving a guidewire 142 for locating the branch vessel 4.

One particular application for the use of a stent with a branch portion 30 such as the one described above is for localized drug delivery. As was discussed hereinabove, restenosis, including in-stent restenosis, is a common problem associated with medical procedures involving the vasculature. Pharmaceutical agents have been found to be helpful in treating and/or preventing restenosis, and these are best delivered locally to the site of potential or actual restenosis, rather than systemically.

As used herein, the term "preventing" includes stopping or reducing the occurrence or severity of a disease or condition or the symptoms of the disease or condition.

As used herein, the term "treating" includes substantially reducing the severity of a disease or condition or the symptoms of the disease or condition, or substantially reducing the appearance of a disease or condition or the symptoms of the disease or condition. The term "treating" includes substantially completely abolishing a disease or condition or the symptoms of the disease or condition. The term "treating" also encompasses preventing, stopping, or reducing the occurrence or severity of a disease or condition or the symptoms of the disease or condition.

When as with anti-restenosis drugs, for example a drug is useful primarily at a particular body site, systemic administration is not necessary and is often undesirable. For instance, systemic administration of drugs often results in undesirable side effects. Also, it is difficult to achieve constant drug delivery to a site needing treatment using systemic delivery methods. Drugs administered systemically often cycle through concentration peaks and valleys, resulting in time periods of toxicity and ineffectiveness. In contrast, drugs delivered in a localized manner can be delivered at a high concentration at the site(s) where treatment is needed, while minimizing the systemic concentration of the drug, thus minimizing or eliminating side effects. Additionally, localized delivery facilitates the maintenance of appropriate drug levels at the treatment site, with minimal undesired fluctuation.

Stents according to the present invention may have one or more drug depots on and/or in the stent wall. As used herein, the term "depot" describes a store of at least one drug designed to retain and thereafter release the drug(s). According to current technology, materials incorporating drug(s) are often associated with stents by coating the drug-containing material(s) onto the walls of the stents. Thus, "coating" is referred to and used herein in describing the depot(s), but this use is solely for convenience of explanation and is in no way limiting, and other methods of associating drug(s) with stents that are currently available or that may become available are specifically contemplated. As another non-limiting example, as is discussed further hereinbelow, stents may be "seeded" with genetically engineered cells that secrete or otherwise release drug(s). As yet another non-limiting example, biocompatible polymers incorporating drug(s) may be molded into a solid mass of a desired size and shape and attached to the stent using pharmaceutically acceptable methods.

The term "depot" refers generally to an area of a stent that is coated or otherwise associated with drug(s) or a material incorporating drug(s). Any given depot is generally discrete from other depots. For example, in certain embodiments, a depot may consist of a discrete mass of material incorporating drug(s). As another example, because the walls of stents according to the present invention comprise open spaces, a depot may also include spaces. A depot may include open spaces, for example, in embodiments where drug(s) or a material incorporating drug(s) is coated or seeded onto a stent to form the depot. One depot may abut, or be adjacent to a second depot, but the second depot will generally have different drug(s) and/or different concentration(s) of drug(s), as is discussed in further depth hereinbelow.

It will be understood that depot(s) of stents according to the present invention can be "on" or "in" the stent walls. For example, where it is desired to release drugs(s) primarily to the cells of the vessel walls at the site of placement of a stent, it may be desirable to coat, attach a drug-containing mass, or otherwise associate drug(s) with only the outer side of the stent wall. As another example, when it is desired to deliver drug(s) to an organ, tissue, or region of the body downstream from a stent, it may be desirable to coat, attach a drug-containing mass, or otherwise associate drug(s) with only the inner side of the stent wall. In still other embodiments, it may be desirable to coat, attach a drug-containing mass, or otherwise associate drug(s) with the inner side of the stent wall, the outer side of the stent wall, and/or the portions of the stent wall that face inward to the open spaces within the wall.

The terms "drug," "drug compound," and "pharmaceutical agents" are used interchangeably herein, unless stated otherwise. These terms are meant to be construed broadly, to mean pharmaceutically acceptable substances (i.e., substances that are safe for use in the body of a mammal such as a human) and that have some biological effect on cells of the body. The terms also include substances that are being tested for safety for use in the body of a mammal such as a human and/or to determine whether (or what) biological effect they have on cells of the body. Examples of types of molecules that may be drugs as the term is defined herein include, but are not limited to, proteins and peptides, small molecules, antibodies, multicyclical molecules, macrolides, and nucleic acids. The general and specific examples provided herein, as well as similar substances, are included in the term "drugs" according to the present invention.

Depots of stents according to the present invention are capable releasing, or eluting, the stored drug(s). Hence, the depots of the present invention can be made of any material that can entrap, encapsulate, adhere, or otherwise retain and thereafter release the stored drug(s). Depots of stents according to the present invention are preferably capable of controllably releasing drug(s). Hence, the depots of the present invention are preferably made of any material that can entrap, encapsulate, adhere or otherwise retain and controllably release the stored drug(s).

The phrases "controllably release", "controllable release," and "controllably releasing" are used herein to describe a release of drug(s) at a predetermined rate and duration under selected conditions. Slow release is one form of controllable release.

In certain preferable embodiments, depots of the present invention comprise one or more biocompatible polymer(s) loaded with drug(s). In certain embodiments, the biocompatible polymer utilized minimizes irritation to the wall of the lumen where the stent is implanted. Methods for incorporating biocompatible polymers loaded with drug(s) into or onto stents generally involve coating the stent with the polymer(s) and are well known in the art. See, e.g., U.S. Pat. No. 5,679, 400.

Several configurations for loading drug(s) into biocompatible polymers are envisaged by the present invention. The drug(s) may be, for example, molded into the polymer, entrapped or encapsulated within the polymer, covalently attached to the polymer, physically adhered to the polymer, or otherwise incorporated into the biocompatible polymer.

The biocompatible polymer may be, for example, either a biostable polymer or a biodegradable polymer, depending on factors such as the desired rate of release or the desired degree of polymer stability under physiological conditions.

Biodegradable polymers that are usable in the context of the present invention include, without limitation, poly(L-lactic add), polycaprolactone, poly(lactide-co-glycolide), poly (hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid.

Biostable polymers that are usable in the context of the present invention include, without limitation, polyurethanes, silicones, polyesters, polyolefins, polyisobutylene, ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

In certain other embodiments, depot(s) on or in stents according to the present invention comprise liposomes into which drug(s) have been encapsulated or entrapped. Methods for incorporating liposomes loaded with drug(s) into or onto stents generally involve coating the stent with the polymer(s) and are known in the art. See, e.g., Kallinteri P. et al. "Dexamethasone incorporating liposomes: an in vitro study of their applicability as a slow releasing delivery system of dexamethasone from covered metallic stents," Biomaterials 23(24):4819-26 (2002). In yet other embodiments, depot(s) depot(s) on or in stents according to the present invention comprise genetically engineered cells that secrete or otherwise release desired drug(s), e.g., therapeutic protein(s). Methods for incorporating genetically engineered cells into or onto stents generally involve seeding the cells onto the stent and are known in the art. See, e.g., Dichek, D. A. et al., "Seeding of Intravascular Stents With Genetically Engineered Endothelial Cells", Circulation, 80:1347-1353 (1989); Flugelman M. Y. et al., "Genetically engineered endothelial cells remain adherent and viable after stent deployment and exposure to flow in vitro," Circ Res., 70:348-54 (1992).

One or more depots may be present at any location in or on the walls of stents according to the present invention. Depot(s) may be utilized with any and all stents according to the present invention. Depot(s) may be present in or on the wall of the main vessel portion of stents according to the present invention. Similarly, depot(s) may be present in or on the wall of the branch portion of stents according to the present invention. The position of depot(s) depends on desired site(s) of highest concentration of drug delivery.

The size of depot(s) on or in stents of the present invention depends on various parameters, such as the material of which the stent body is fabricated, the permeability of the stent body and the depot, the efficacy of the depot in retaining the drug(s), the concentration of the drug(s), and the desired rate and duration of release of the drug(s). Depot(s) may extend around the entire, or only a portion of, the circumference of main vessel portions of stents according to the present invention. Likewise, depot(s) may extend longitudinally for all or only a portion of the length of main vessel portions of stents according to the present invention. With regard to branch portions of stents according to the present invention, depot(s) may cover all or only a portion of the walls, or may be in all or only a portion of the walls.

When it is desired to increase the overall volume of a depot, it may often be preferable to increase the length and/or width of the depot, rather than its thickness, or depth. In other words, it may often be preferable to increase the size of a depot along or within the wall of a stent, rather than extending the depot farther into the lumen of the stent. Depot(s) that extend too far into the lumen of a stent may impede fluid flow through the stent, and depots that are too thick on the outside wall may deform the stent into the vessel, also impeding fluid flow. However, it may be desirable to concentrate a large volume of depot in a small surface area, to maximize drug concentration to a small section of vessel. Contrariwise, it may in other instances be desirable to have drug(s) released along a large section of vessel, in which cases it may be desirable to use a depot that has a large surface area along or within a wall of the stent.

Thus, the length, width, and thickness of a depot are variables that can be tailored according to the desired drug distribution and the size of the main and branch vessels to be treated. For example, a depot that is thick enough to impede fluid flow in a narrow vessel may be an optimal thickness for a larger vessel.

Additionally, the concentration of drug(s) in a depot can be varied according to the desired rate of elution of the drug from the depot and the desired concentration of the drug in the local area of the depot. Thus, the parameters of depot length, width, and thickness and drug concentration can be varied to tailor depots to elute the desired concentration of drug(s) to the desired area(s) in vessels of varying sizes.

Non-limiting examples of anti-restenosis drugs that may be incorporated into depot(s) in or on stents according to the present invention include anticoagulant agents, antiproliferative agents, antimigratory agents, antimetabolic agents, anti-inflammatory agents, and immunosuppressive substances, and combinations thereof Particularly useful anti-restenosis drugs include paclitaxel, rapamycin, and HDAC inhibitors. Examples of histone deacetylase (HDAC) inhibitors, which are efficient inhibitors of smooth muscle cell (SMC) proliferation, include, without limitation, hydroxamic acids such as trichostatin A (TSA), suberoyl anilide hydroxamic acid (SAHA), oxamflatin, m-carboxycinnamic acid bishydroxamide (CBHA), cyclic hydroxamic acid-containing peptide 1 (CHAP 1), cyclic hydroxamic acid-containing peptide 31 (CHAP31), suberic bishydroxamate (SBHA), pyroxamide, and scriptaid. Further details pertaining to an HDAC inhibitors, their use, and stents incorporating same are disclosed in a U.S. Provisional Patent Application assigned to a common assignee of the present invention, filed Jul. 24, 2002, entitled "STENTS CAPABLE OF CONTROLLABLY RELEASING HISTONE DEACETYLASE INHIBITORS," incorporated by reference herein in its entirety.

In addition to anti-restenosis drugs, stents according to the present invention can also be used as vehicles for localized delivery of other drugs. As a non-limiting example, stents of the present invention are particularly useful in for localized delivery of anti-thrombotic drugs. Thrombosis (the formation of a thrombus, or blot clot) sometimes occurs in association with medical procedures involving the vasculature. For example, thrombosis may result from physical injury of an arterial wall by a vascular interventional procedure such as percutaneous transluminal coronary angioplasty ("PTCA"; a type of balloon angioplasty) or coronary bypass surgery. Although thrombosis can result in death, the procedures which may have thrombosis as a side effect are themselves are life-saving and widely used. Additionally, thrombosis may also result from progression of a natural disease, such as atherosclerosis. Accordingly, administration of anti-thrombotic drugs to patients who have undergone vascular procedures is often desirable.

Many anti-thrombotic drugs are known in the art. Non-limiting examples include aspirin (acetylsalicylic acid), prostaglandin $E_1$, selective thromboxane $A_2$ inhibitors, selective thrombin inhibitors, platelet receptor GPIIb/IIIa blockers, tissue plasminogen activator, streptokinase, heparin, hirudin, bivalirudin, and kistrin and other platelet and/or thrombin inhibitors. As with anti-restenosis drugs, administration of anti-thrombotics locally to the site of potential thrombosis is usually vastly preferable to systemic administration.

Additional, non-limiting examples of types of drugs that may be incorporated into depot(s) in or on stents according to the present invention include antineoplastic, antimitotic, anti-platelet, antifibrin, antithrombiin, antibiotic, antioxidant, and antiallergic substances as well as combinations thereof.

Depots for use in accordance with the present invention may include one or more different drug(s). For example, it will often be desirable to include two or more drugs that have additive, or even synergistic effects. Where more than one drug is incorporated into a single depot, it will be generally preferred to incorporate drugs that will not interfere with, degrade, destabilize, or otherwise interfere with one another. However, in some cases in may be desirable to include a first drug along with a second drug that reduces or alters the activity of the first drug in a desired manner. In the same manner, different depots may include different drugs, or different concentrations of the same drug. The many possible permutations allow for great flexibility in treatment.

Stents according to the present invention can be used as vehicles for localized delivery of drugs to cells of the walls of both the main and branch vessels at the location of the stent. Drugs that are particularly suitable for treatment of cells in the immediate area of the stent include anti-restenosis and anti-thrombotic drugs. If desired, different concentrations of drugs, or different drugs, may be included in depot(s) located in or on different areas of the stent walls. For example, it may be desirable to treat the cells of the main vessel with a first drug, combination of drugs, and/or concentration of drug(s) and to treat the cells of the branch vessel with a second, different, drug, combination of drugs, and/or concentration of drug(s). As another example, it may be desirable to maintain a high concentration of anti-restenosis drug(s) near the bifurcation of the vessels. As yet another non-limiting example, it may be desirable to maintain a high concentration of anti-restenosis drug(s) at the three open ends (two on the main portion and one on the branch portion) of the stent. It will be appreciated by one skilled in the art upon reading the present disclosure that many combinations of two or more depots are possible within the spirit and scope of the present invention.

Stents according to the present invention can be used as vehicles to deliver drug(s) to an organ, tissue, or region of the body downstream from the stent. For example, stents according to the present invention may be positioned in an artery that supplies blood to an organ, such as the heart, in a location close to that organ. Drug(s) that elute from the depot(s) in or on the stent may be carried by the blood flow to the organ. In this way, localized delivery to tissues, organs, and body regions can be achieved. Using stents according to the present invention, a first drug, combination of drugs, and/or concentration of drug(s), may be delivered to an organ, tissue, or region downstream from the main portion of the stent while a second, different, drug, combination of drugs, and/or concentration of drug(s) is delivered to an organ, tissue, or region downstream from the branch portion of the stent. This differential delivery can be accomplished by locating a depot having a first drug, combination of drugs, and/or concentration of drug(s) in or on an area of the main portion of the stent that is not contacted by blood flowing through the branch vessel, and locating a second depot having a second, different, drug, combination of drugs, and/or concentration of drug(s) in or on the branch portion of the stent. It will be appreciated by one skilled in the art upon reading the present disclosure that many combinations of two or more depots are possible within the spirit and scope of the present invention.

Specific, and non-limiting, examples of drugs that may be incorporated into depot(s) in or on stents according to the present invention include the following drugs. Examples of antineoplastic and/or antimitotic drugs include docetaxel (e.g., Taxotere® from Aventis S. A., Frankfurt, Germany) methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of antiplatelet, anticoagulant, antifibrin, and antithrombin drugs include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of cytostatic or antiproliferative drugs include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.); calcium channel blockers (such as nifedipine), colchicine, fibroblast growth factor (FGF) antagonists, histamine antagonists, lovastatin (an HMG-CoA reductase inhibitor, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alpha-interferon and dexamethasone. The preventative and treatment properties of the foregoing therapeutic substances or agents are well-known to those of ordinary skill in the art.

The present invention also provides kits comprising a stent or stents according to the present invention. In addition to a stent or stents, a kit according to the present invention may include, for example, delivery catheter(s), balloon(s), and/or instructions for use. In kits according to the present invention, the stent(s) may be mounted in or on a balloon or catheter. Alternatively, the stent(s) may be separate from the balloon or catheter and may be mounted therein or thereon prior to use.

While the invention has been described in conjunction with specific embodiments and examples thereof, it is evident that many alternatives, modifications and variations will be apparent to those skilled in the art upon reading the present disclosure. Accordingly, it is intended to embrace all such alternatives, modifications and variations that fall within the spirit and broad scope of the appended claims.

What is claimed is:

1. A stent comprising:
a tubular member defining a stent longitudinal axis, the tubular member having a first end section, a midsection and a second end section the tubular member comprising a framework having a plurality of openings;
the midsection comprising an expandable branch structure, a first partial serpentine ring and a first transition member, the expandable branch structure comprising a side branch ring comprising a plurality of outwardly expandable petals, the side branch ring defining a central branch opening having a unique shape, the first transition member comprising a first straight portion oriented non-parallel to the stent longitudinal axis, the first partial serpentine ring comprising alternating struts and turns, wherein a first plurality of adjacent struts each comprise a straight portion that is parallel to the first straight portion of the first transition member.

2. The stent of claim 1, wherein each strut of the first plurality of adjacent struts further comprises a second straight portion that is parallel to the stent longitudinal axis.

3. The stent of claim 1, wherein the first plurality of adjacent struts comprises at least four struts.

4. The stent of claim 1, wherein at least a portion of the first transition member is positioned between the expandable branch structure and the first partial serpentine ring.

5. A stent comprising:
a tubular member defining a stent longitudinal axis, the tubular member having a first end section, a midsection and a second end section;
the midsection comprising an expandable branch structure, a first partial serpentine ring and a first transition member, the expandable branch structure comprising a side branch ring comprising a plurality of outwardly expandable petals, the first transition member comprising a first straight portion oriented non-parallel to the stent longitudinal axis, the first partial serpentine ring comprising alternating struts and turns, wherein a first plurality of adjacent struts each comprise a straight portion that is parallel to the first straight portion of the first transition member;
wherein the first transition member comprises a curved portion, and the first partial serpentine ring is attached at one end to a first portion of the curved portion and is attached at the other end to a second portion of the curved portion.

6. A stent comprising:
a tubular member defining a stent longitudinal axis, the tubular member having a first end section, a midsection and a second end section;
the midsection comprising an expandable branch structure, a first partial serpentine ring and a first transition member, the expandable branch structure comprising a side branch ring comprising a plurality of outwardly expandable petals, the first transition member comprising a first straight portion oriented non-parallel to the stent longitudinal axis, the first partial serpentine ring comprising alternating struts and turns, wherein a first plurality of adjacent struts each comprise a straight portion that is parallel to the first straight portion of the first transition member;
the first transition member comprising a second straight portion oriented non-parallel to the first straight portion, wherein a second plurality of adjacent struts of the first partial serpentine ring each comprise a straight portion that is parallel to the second straight portion of the first transition member.

7. The stent of claim 6, wherein each strut of the second plurality of adjacent struts further comprises a second straight portion that is parallel to the stent longitudinal axis.

8. The stent of claim 6, wherein the second plurality of adjacent struts comprises at least four struts.

9. The stent of claim 6, wherein the first straight portion of the first transition member is positioned between the expandable branch structure and the first plurality of adjacent struts, and the second straight portion of the first transition member is positioned between the expandable branch structure and the second plurality of adjacent struts.

10. The stent of claim 6, wherein the second straight portion of the first transition member comprises a mirror image of the first straight portion.

11. The stent of claim 10, wherein the mirror image is taken across a line parallel to the stent longitudinal axis.

12. The stent of claim 6, the midsection further comprising a second transition member and a second partial serpentine ring.

13. The stent of claim 12, wherein the second transition member comprises a mirror image of the first transition member.

14. The stent of claim 13, wherein the second partial serpentine ring comprises a mirror image of the first partial serpentine ring.

15. The stent of claim 12, the second transition member comprising a first straight portion oriented non-parallel to the stent longitudinal axis, the second partial serpentine ring comprising a first plurality of adjacent struts that each comprise a straight portion that is parallel to the first straight portion of the second transition member.

16. The stent of claim 15, wherein each strut of the first plurality of adjacent struts of the second partial serpentine ring further comprises a second straight portion that is parallel to the stent longitudinal axis.

17. The stent of claim 15, the second transition member comprising a second straight portion oriented non-parallel to the first straight portion of the second transition member, wherein a second plurality of adjacent struts of the second partial serpentine ring each comprise a straight portion that is parallel to the second straight portion of the second transition member.

18. The stent of claim 17, wherein each strut of the second plurality of adjacent struts of the second partial serpentine ring further comprises a second straight portion that is parallel to the stent longitudinal axis.

19. The stent of claim 17, wherein the first straight portion of the second transition member is positioned between the expandable branch structure and the first plurality of adjacent struts of the second partial serpentine ring, and the second straight portion of the second transition member is positioned between the expandable branch structure and the second plurality of adjacent struts of the second partial serpentine ring.

20. The stent of claim 12, wherein the second transition member comprises a curved portion, and the second partial serpentine ring is attached at one end to a first portion of the curved portion and is attached at the other end to a second portion of the curved portion.

* * * * *